(12) United States Patent
Takaishi et al.

(10) Patent No.: US 9,175,013 B2
(45) Date of Patent: Nov. 3, 2015

(54) FUSED AMINODIHYDROTHIAZINE DERIVATIVES

(75) Inventors: Mamoru Takaishi, Tsukuba (JP); Tasuku Ishida, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/979,961

(22) PCT Filed: Jan. 19, 2012

(86) PCT No.: PCT/IB2012/000082
§ 371 (c)(1),
(2), (4) Date: Sep. 18, 2013

(87) PCT Pub. No.: WO2012/098461
PCT Pub. Date: Jul. 26, 2012

(65) Prior Publication Data
US 2014/0179690 A1 Jun. 26, 2014

(30) Foreign Application Priority Data
Jan. 21, 2011 (GB) .................................. 1101139.2

(51) Int. Cl.
*C07D 513/04* (2006.01)
*A61K 31/542* (2006.01)
*A61K 45/06* (2006.01)

(52) U.S. Cl.
CPC ............ *C07D 513/04* (2013.01); *A61K 31/542* (2013.01); *A61K 45/06* (2013.01)

(58) Field of Classification Search
CPC ..................................................... C07D 513/04
USPC ........................................ 544/48; 514/224.2
See application file for complete search history.

(56) References Cited

U.S. PATENT DOCUMENTS

| | | | |
|---|---|---|---|
| 3,227,713 A | 1/1966 | Behner et al. |
| 3,235,551 A | 2/1966 | Schubert et al. |
| 6,642,237 B1 | 11/2003 | Tata et al. |
| 7,189,715 B2 | 3/2007 | Jerussi et al. |
| 7,648,983 B2 | 1/2010 | Audia et al. |
| 8,158,620 B2 | 4/2012 | Suzuki et al. |
| 8,198,269 B2 | 6/2012 | Motoki et al. |
| 8,278,441 B2 | 10/2012 | Mergott et al. |
| 8,338,407 B2 | 12/2012 | Hall et al. |
| 8,426,584 B2 | 4/2013 | Mitasev et al. |
| 8,501,733 B2 | 8/2013 | Motoki et al. |
| 8,592,408 B2 | 11/2013 | Hall et al. |
| 2004/0110743 A1 | 6/2004 | Miyamato et al. |
| 2006/0052406 A1 | 3/2006 | Fisher et al. |
| 2006/0111370 A1 | 5/2006 | Zhu et al. |
| 2007/0021454 A1 | 1/2007 | Coburn et al. |
| 2007/0287692 A1 | 12/2007 | Wu et al. |
| 2008/0139538 A1 | 6/2008 | McGaughey et al. |
| 2008/0200445 A1 | 8/2008 | Zhu et al. |
| 2009/0082560 A1 | 3/2009 | Kobayashi et al. |
| 2009/0209755 A1 | 8/2009 | Suzuki et al. |
| 2010/0075957 A1 | 3/2010 | Tamura et al. |
| 2010/0093999 A1 | 4/2010 | Motoki et al. |
| 2010/0160290 A1 | 6/2010 | Kobayashi et al. |
| 2010/0317850 A1 | 12/2010 | Suzuki et al. |
| 2011/0009395 A1 | 1/2011 | Audia et al. |
| 2011/0152253 A1 | 6/2011 | Motoki et al. |
| 2011/0207723 A1 | 8/2011 | Motoki et al. |
| 2012/0094984 A1 | 4/2012 | Suzuki et al. |
| 2012/0190672 A1 | 7/2012 | Hall et al. |

(Continued)

FOREIGN PATENT DOCUMENTS

| EP | 1 942 105 | 7/2008 |
|---|---|---|
| EP | 2 233 474 | 9/2010 |

(Continued)

OTHER PUBLICATIONS

International Search Report and Written Opinion in International Application No. PCT/IB2012/000082, mailed Apr. 4, 2012, 6 pages.
International Preliminary Report on Patentability in International Application No. PCT/IB2012/000082, issued Jul. 23, 2013, 4 pages.
Abdel-Magid et al., "Reductive Amination of Aldehydes and Ketones with Sodium Triacetoxyborohydride. Studies on Direct and Indirect Reductive Amination Procedures," *J. Org. Chem.*, 61(11):3849-3862 (1996).
Agarwal et al., "Pyridinium chlorochromate. An improved method for its synthesis and use of anhydrous acetic acid as catalyst for oxidation reactions," Tetrahedron, 1990, 46:4417-4420.
Ames et al., "Methods for detecting carcinogens and mutagens with the Salmonella/mammalian-microsome mutagenicity test," *Mutat. Res.*, 31:347-364 (1975).

(Continued)

*Primary Examiner* — Bruck Kifle
(74) *Attorney, Agent, or Firm* — Fish & Richardson P.C.

(57) ABSTRACT

The present invention relates to a fused aminodihydrothiazine derivative of formula (I): wherein X is hydrogen or fluorine; R is monofluoromethyl or difluoromethyl; and pharmaceutically acceptable salts thereof; which compound has an Aβ production inhibitory effect or a BACE1 inhibitory effect and is useful as a prophylactic or therapeutic agent for a neurodegenerative disease caused by Aβ and typified by Alzheimer-type dementia.

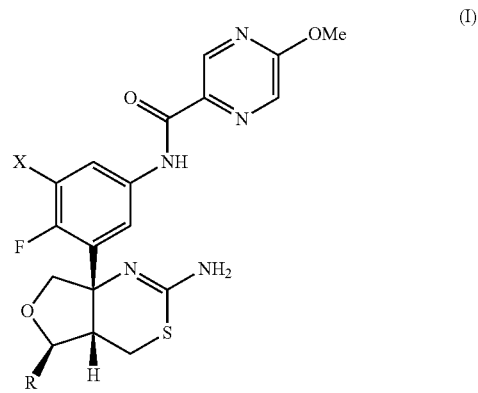

8 Claims, 1 Drawing Sheet

(56) References Cited

U.S. PATENT DOCUMENTS

| | | |
|---|---|---|
| 2012/0190848 A1 | 7/2012 | Mitasev et al. |
| 2012/0202804 A1 | 8/2012 | Ellard et al. |
| 2012/0202828 A1 | 8/2012 | Castro Pineiro et al. |
| 2013/0197244 A1 | 8/2013 | Mitasev et al. |
| 2013/0203740 A1 | 8/2013 | Hall et al. |
| 2013/0203741 A1 | 8/2013 | Suzuki et al. |

FOREIGN PATENT DOCUMENTS

| | | |
|---|---|---|
| JP | 09-067355 | 3/1997 |
| JP | 2004-149429 | 5/2004 |
| WO | WO 01/87293 | 11/2001 |
| WO | WO 02/096897 | 12/2002 |
| WO | WO 2004/014843 | 2/2004 |
| WO | WO 2004/043916 | 5/2004 |
| WO | WO 2005/058311 | 6/2005 |
| WO | WO 2005/097767 | 10/2005 |
| WO | WO 2006/041404 | 4/2006 |
| WO | WO 2006/041405 | 4/2006 |
| WO | WO 2006/059234 | 6/2006 |
| WO | WO 2006/138264 | 12/2006 |
| WO | WO 2007/011810 | 1/2007 |
| WO | WO 2007/049532 | 5/2007 |
| WO | WO 2007/114771 | 10/2007 |
| WO | WO 2007/139230 | 12/2007 |
| WO | WO 2008/073365 | 6/2008 |
| WO | WO 2008/133273 | 11/2008 |
| WO | WO 2008/133274 | 11/2008 |
| WO | WO 2009/067081 | 5/2009 |
| WO | WO 2009/091016 | 7/2009 |
| WO | WO 2009/131974 | 10/2009 |
| WO | WO 2009/134617 | 11/2009 |
| WO | WO 2009/151098 | 12/2009 |
| WO | WO 2010/013302 | 2/2010 |
| WO | WO 2010/013794 | 2/2010 |
| WO | WO 2010/021680 | 2/2010 |
| WO | WO 2010/038686 | 4/2010 |
| WO | WO 2010/105179 | 9/2010 |
| WO | WO 2011/005738 | 1/2011 |
| WO | WO 2011/009897 | 1/2011 |
| WO | WO 2011/009898 | 1/2011 |
| WO | WO 2012/003274 | 1/2012 |
| WO | WO 2012/093148 | 7/2012 |
| WO | WO 2012/098461 | 7/2012 |
| WO | WO 2012/100179 | 7/2012 |

OTHER PUBLICATIONS

Aranyos et al., "Novel Electron-Rich Bulky Phosphine Ligands Facilitate the Palladium-Catalyzed Preparation of Diaryl Ethers," *J Am Chem Soc.*, 121(18):4369-4378 (1999).

Arnone et al., An Enantiospecific Entry to Fluoro Substituted Aminocyclopentanols through Intramolecular Nitrile Oxide, Nitrone, and Oxime Cycloaddition Reactions, *Tetrahedron: Asymmetry* 5(6):1019-1028 (1994).

Aschwanden et al., "Reduction of 2,3-dihydroisoxazoles to beta-amino ketones and beta-amino alcohols," *Org. Lett.*, 7(25):5741-5742 (2005).

Barange et al., "A Remarkable Accelerating Effect of Ag-Salt on Intramolecular Cyclization of o-(1-Alkynyl)benzenesulfonamides," *J. Org. Chem.*, 72(22):8547-8550 (2007).

Barlow et al., "Intervalence Transitions in the Mixed-Valence Monocations of Bis(triarylamines) Linked with Vinylene and Phenylene—Vinylene Bridges," *J. Am. Chem. Soc.*, 127(48):16900-16911 (2005).

Bennua-Shalmowski and Vorbruggen, "A facile conversion of primary or secondary alcohols with n-perfluorobutane-sulfonyl fluoride/1,8-diazabicyclo[5.4.0]undec-7-ene into their corresponding fluorides," Tetrahedron Lett., 1995, 36:2611-2614.

Berge et al., "Pharmaceutical salts," *J. Pharm. Sci.*, 66:1-19 (1977).

Bobrov et al., "Interaction of Quinone Oxide with Thiourea" *Chemistry and Chemical Technology*, 33(10):15-18 (1990) (original and English language translation).

Boeckman et al., "The Dess-Martin Periodinane: 1,1,1-Triacetoxy-1,1-Dihydro-1,2-Benziodoxol-3(1H)-One," Org. Synth. Coll., 2004, 10:696, 6 pages.

Brzostwska et al., "Chiral Prodyes: Synthesis and Full Characterization of (S)-1-Phenylethylamides of the Optically Active Q-Methyldihydrofluoresceins," *Heterocycles*, 32(10):1968-1972 (1991).

Butler et al., "A Facile Synthesis of New 5H-Indazolo[3,2-b]benzo[d]-1,3-oxazines via One-Pot Intramolecular Bis-heterocyclizations," *J. Org. Chem.*, 73(1):234-240 (2008).

Chakrabarty et al., "DBU, a highly efficient reagent for the facile regeneration of (hetero)arylamines from their acetamides and benzamides: influence of solvent, temperature, and microwave irradiation," *Synth. Commun.*, 32(2):265-272 (2002).

Coates et al., "Annelative ring expansion via intramolecular [2+2] photocycloaddition of .alpha.,.beta.-unsaturated .gamma.-lactones and reductive cleavage: synthesis of hydrocyclopentacyclooctene-5-carboxylates," *J. Org. Chem.*, 47(19):3597-3607 (1982).

Cohen et al., "Synthesis of 2-Amino-5,6-dihydro-4H-1,3-thiazines and Related Compounds by Acid Catalyzed Cyclization of Allylic Isothiuronium Salts," *Journal of Heterocyclic Chemistry*, 14:717-723 (1977).

Corey and Kim, "New and highly effective method for the oxidation of primary and secondary alcohols to carbonyl compounds," J. Am. Chem. Soc., 1972, 94(21):7586-7587.

Corey and Suggs, "Pyridinium Chlorochromate. An efficient reagent for oxidation of primary and secondary alcohols to carbonyl compounds," Tetrahedron Lett., 1975, 16, 2647-2650.

Crisp and Meyer, "Palladium-catalyzed, carbonylative, intramolecular coupling of hydroxyvinyl triflates. Synthesis of substituted .alpha.,.beta.-butenolides," *J. Org. Chem.*, 57(25):6972-6975 (1992).

Cross et al., International Union of Pure and Applied Chemistry (IUPAC) Rules for the Nomenclature of Organic Chemistry, Section E, Stereochemistry, *Pure & Applied Chemistry*, 45:11-30 (1976).

Danheiser et al., "An annulation method for the synthesis of highly substituted polycyclic aromatic and heteroaromatic compounds," *J. Am. Chem. Soc.*, 112(8):3093-3100 (1990).

Darses et al., "Palladium-catalyzed cross-coupling reactions of arenediazonium tetrafluoroborates with aryl- and alkenylboronic acids," Bulletin de la Societe Chimique de France 1996, 133(11), 1095-1102.

De Lucca et al., "Discovery and Structure—Activity Relationship of N-(Ureidoalkyl)-Benzyl-Piperidines as Potent Small Molecule CC Chemokine Receptor-3 (CCR3) Antagonists," *J. Med. Chem.*, 45(17)3794-3804 (2002).

Dess and Martin, "Readily accessible 12-I-5 oxidant for the conversion of primary and secondary alcohols to aldehydes and ketones," J. Org. Chem. 1983, 48:4155-4156.

Dorwald, F.A., Side Reactions in Organic Synthesis, 2005, Wiley: VCH, Weinheim, p. IX, 15 pages.

Edwards et al., "Application of Fragment-Based Lead Generation to the Discovery of Novel, Cyclic Amidine β-Secretase Inhibitors with Nanomolar Potency, Cellular Activity, and High Ligand Efficiency," *J. Med. Chem.*, 50(24):5912-5925 (2007).

Fang et al., "Synthesis, Antibacterial, and Cytotoxic Evaluation of Certain 7-Substituted Norfloxacin Derivatives," *J. Med. Chem.*, 43(20):3809-3812 (2000).

Farina and Krishnamurthy, "The Stille Reaction," J. Org. React. 1998, 50, 1-652.

Forman et al., "Differential Effects of the Swedish Mutant Amyloid Precursor Protein on β-Amyloid Accumulation and Secretion in Neurons and Nonneuronal Cells," *The Journal of Biological Chemistry*, 272(51):32247-32253 (1997).

Fuller et al., "Succinct Synthesis of β-Amino Acids via Chiral Isoxazolin," *J. Am. Chem. Soc.*, 127(15):5376-5383 (2005).

Fuller et al., "Synthesis and Structural Characteristics of Geminally Disubstituted β-Amino Acids," *Synlett.*, 8:1409-1413 (2004).

Fulop et al., "Synthesis of Stereoisomers 2-Phenylimino-3, 1-Perhydro-Benzoxazines and 3, 1-Perhydrobenzothiazines," *Org Prep Proced Int'l*, 20:73-82 (1988).

(56) References Cited

OTHER PUBLICATIONS

Glenner et al., "Alzheimer's Disease: Initial report of the purification and characterization of a novel cerebrovascular amyloid protein," *Biochemical and Biophysical Research Communications*, 120(3):885-890 (1984).
Gloor et al., "Molecular and cellular permeability control at the blood-brain barrier," *Brain Res. Rev.*, 36:258-264 (2001).
Gong et al., "Alzheimer's disease-affected brain: Presence of oligomeric Aβ ligands (ADDLs) suggests a molecular basis for reversible memory loss," *Proceeding National Academy of Science USA*, 100(18):10417-10422 (2003).
Gouras et al., "Intraneuronal Aβ42 Accumulation in Human Brain," *American Journal of Pathology*, 156(1):15-20 (2000).
Green et al., "Mutagen testing using TRP+ reversion in *Escherichia coli*," *Mutat. Res.*, 38:3-32 (1976).
Greene and Wuts "Protective Groups in Organic Chemistry, Third Edition", *John Wiley & Sons* p. 102-104 (1999).
Greene and Wuts, "Protective Groups in Organic Chemistry, Second Edition", *John Wiley & Sons* p. 327-330 (1991).
Greene and Wuts, "Protective Groups in Organic Chemistry, Third Edition", *John Wiley & Sons*, p. 17-245 (1999).
Greene and Wuts, "Protective Groups in Organic Chemistry, Third Edition", *John Wiley & Sons*, p. 293-329 (1999).
Greene and Wuts, "Protective Groups in Organic Chemistry, Third Edition", *John Wiley & Sons*, p. 494-572 (1999).
Greene and Wuts, "Protective Groups in Organic Chemistry, Third Edition", *John Wiley & Sons*, p. 506-507 (1999).
Greene and Wuts, "Protective Groups in Organic Chemistry, Third Edition", *John Wiley & Sons*, p. 531-537 (1999).
Greene and Wuts, "Protective Groups in Organic Chemistry, Third Edition", *John Wiley & Sons*, p. 642-643 (1999).
Greene et al., "Protective Groups in Organic Chemistry, Third Edition," *John Wiley & Sons*, 404-408 (1999).
Greene et al., "Protective Groups in Organic Chemistry, Third Edition," *John Wiley & Sons*, 518-525 (1999).
Gu et al., "Facile One-Pot Synthesis of 6-Monosubstituted and 6,12-Disubstituted 5,11-Dihydroindolo[3,2-b]carbazoles and Preparation of Various Functionalized Derivatives," *J. Org. Chem.*, 72(19):7207-7213 (2007).
Hall et al., "Comparative pharmacokinetic-pharmacodynamic responses in rat and cynomolgus monkey for a novel BACE inhibitor ER-901356," 11th *Int'l Conf on Alzheimer's & Parkinson's Diseases (AD/PD 2013)*, 4 pages, (Mar. 6-10, 2013).
Han et al., "Diverse Synthesis of Novel Bisterpyridines via Suzuki-Type Cross-Coupling," *Org. Lett.*, 9(4):559-562 (2007).
Hassner et al. "Stereochemistry. 82. Conformation of fused five-membered heterocyclic rings derived from the intramolecular oxime olefin cycloaddition reaction," *J. Org. Chem.*, 58(17):4539-4546 (1993).
Hassner, "Interamolecular Oxime Olefin Cycloadditions. Stereospecific Formation of Functionalized Pyrrolidines," *Tetrahedron Letters*, 29(41):5313-5316 (1988).
He et al., "Utility of unbound plasma drug levels and P-glycoprotein transport data in prediction of central nervous system exposure," *Xenobiotica*, 39:687-693 (2009).
Heany et al., "The influence of oxime stereochemistry in the generation of nitrones from omega-alkenyloximes by cyclization or 1,2-prototropy," *J. Chem. Soc., Perkin Trans.*, 1:341-349 (Jan. 1, 1998).
Hitchcock et al., "Structure-brain exposure relationships," *J. Med. Chem.*, 49:7559-7583 (2006).
Hock et al., "Antibodies against β-Amyloid Slow Cognitive Decline in Alzheimer's Disease," *Neuron*, 38:547-554 (2003).
Howbert et al., "Novel agents effective against solid tumors: the diarylsulfonylureas. Synthesis, activities, and analysis of quantitative structure-activity relationships," *J. Med. Chem.*, 33:2393-2407 (1990).
Hussain et al., "Oral administration of a potent and selective non-peptidic BACE-1 inhibitor decreases beta-cleavage of amyloid precursor protein and amyloid-beta production in vivo," *J. Neurochem.*, 100:802-809 (2007).

Iserloh et al., "Discovery of an orally efficaceous 4-phenoxypyrrolidine-based BACE-1 inhibitor," *Bioorg. Med. Chem. Lett.*, 18:418-422 (2008).
Ishikawa et al., "Synthesis of A-Ring Fragments of 1α,25-Dihydroxyvitamin $D_3$ and Taxane Diterpenoids: Effective Construction of Conjugated Formylcyclohexene Frameworks from Isoxazolines," *Tetrahedron*, 54(22):5869-5882 (1998).
Ishiyama et al., "Palladium(0)-Catalyzed Cross-Coupling Reaction of Alkoxydiboron with Haloarenes: A Direct Procedure for Arylboronic Esters," *J. Org. Chem.* 1995, 60(23):7508-7510.
Iwata et al., "Radiosynthesis of O-[$^{11}$C]methyl-L-tyrosine and O-[$^{18}$F]Fluoromethyl-L-tyrosine as potential PET tracers for imaging amino acid transport," *J Labelled Compounds & Radiopharmaceuticals*, 46(6):555-566 (2003).
Jarrett et al., "The Carboxy Terminus of the β Amyloid Protein is Critical for the Seeding of Amyloid Formation: Implications for the Pathogenesis of Alzheimer's Disease," *Biochemistry*, 32(18):4693-4697 (1993).
Ji et al., "Synthesis and Structure—Activity Relationship Studies of 3,6-Diazabicyclo[3.2.0]heptanes as Novel α4β2 Nicotinic Acetylcholine Receptor Selective Agonists," *J. Med. Chem.*, 50(22):5493-5508 (2007).
Kalvass et al., "Influence of nonspecific brain and plasma binding on CNS exposure: implications for rational drug discovery," *Biopharm. Drug Dispos.*, 23:327-338 (2002).
Katagiri et al., "Synthesis of Chiral Spiro 3-Oxazolin-5-one 3-Oxides (Chiral Nitrones) via a Nitrosoketene Intermediate and Their Asymmetric 1,3-Dipolar Cycloaddition Reactions Leading to the EPC Synthesis of Modified Amino Acids," *Tetrahedron*, 53(16):5725-5746 (1997).
Kearney et al., "Solid-Phase Synthesis of 2-Aminothiazoles," *J. Org. Chem.*, 63(1):196-200 (1998).
King et al., "Highly general stereo-, regio-, and chemo-selective synthesis of terminal and internal conjugated enynes by the Pd-catalysed reaction of alkynylzinc reagents with alkenyl halides," *J. Chem. Soc., Chem. Commun.*, 1977, 683-684.
Knauer and Kunz, "Palladium-catalysed C-C coupling reactions in the enantioselective synthesis of 2,4-disubstituted 4,5-dehydropiperidines using galactosylamine as a stereodifferentiating auxiliary," *Tetrahedron: Asymmetry*, 16(2):529-539 (2005).
Kuo et al., "A Synthesis of Estrone via Novel Intermediates, Mechanism of the Coupling Reaction of a Vinyl Carbinol with a β Diketone," *Journal of Organic Chemistry*, 33(8):3126-3132 (1968).
Kusuhara et al., "Efflux transport systems for drugs at the blood-brain barrier and blood-cerebrospinal fluid barrier (Part 1)," *Drug Discov. Today*, 6:150-156 (2001).
Kwong et al., "Copper-Catalyzed Coupling of Alkylamines and Aryl Iodides: An Efficient System Even in an Air Atmosphere," *Org. Lett.*, 4(4):581-584 (2002).
L'Heureux et al., "Aminodifluorosulfinium Salts: Selective Fluorination Reagents with Enhanced Thermal Stability and Ease of Handling," J. Org. Chem., 2010, 75:3401-3411.
Lal et al., "Bis(2-methoxyethyl)aminosulfur trifluoride: a new broad-spectrum deoxofluorinating agent with enhanced thermal stability," Chem. Commun. 1999, 215-216.
Lal et al., "Bis(2-methoxyethyl)aminosulfur Trifluoride: A New Broad-Spectrum Deoxofluorinating Agent with Enhanced Thermal Stability," J. Org. Chem. 1999, 64:7048-7054.
Leroux et al., "Trifluoromethoxy Substituted Anilines: Metalation as the Key Step for Structural Elaboration," *J. Org. Chem.*, 68(12):4693-4699 (2003).
Ley et al., "Tetrapropylammonium Perruthenate, Pr4N+RuO4-, TPAP: A Catalytic Oxidant for Organic Synthesis," Synthesis, 1994, 639-666.
Lin et al., "Role of P-glycoprotein in pharmacokinetics: clinical implications," *Clin. Pharmacokinet.*, 42:59-98 (2003).
Lin, "How significant is the role of P-glycoprotein in drug absorption and brain uptake?," *Drugs of Today*, 40:5-22 (2004).
Littke et al., "Versatile Catalysts for the Suzuki Cross-Coupling of Arylboronic Acids with Aryl and Vinyl Halides and Triflates under Mild Conditions," *J. Am. Chem. Soc.*, 122(17):4020-4028 (2000).

(56) References Cited

OTHER PUBLICATIONS

Liu et al., "A practical and chemoselective reduction of nitroarenes to anilines using activated iron," *Adv. Synth. Caral.*, 347:217-219 (2005).

Mahar et al., "Passive permeability and P-glycoprotein-mediated efflux differentiate central nervous system (CNS) and non-CNS marketed drugs," *J. Pharmacol. Exp. Ther.*, 303:1029-1037 (2002).

Malamas et al., "Design and synthesis of aminohydantoins as potent and selective human β-secretase (BACE1) inhibitors with enhanced brain permeability," *Bioorg. Med. Chem. Lett.*, 20:6597-6605 (2010).

Mancuso and Swern, "Activated dimethyl sulfoxide: Useful reagents for synthesis," Synthesis, 1981, 3:165-185.

Martin et al., "Simple and Efficient Preparation of Ketones from Morpholine Amides," Synlett, 1997, 12:1414-1416.

Masters et al., "Amyloid plaque core protein in Alzheimer disease and Down syndrome," *Proceeding National Academy of Science USA*, 82:4245-4249 (1985).

Matassa et al., "Synthesis and in vitro LTD4 antagonist activity of bicyclic and monocyclic cyclopentylurethane and cyclopentylacetamide N-arylsulfonyl amides," *J. Med. Chem.*, 33(9):2621-2629 (1990).

Maurer, "Relationship between exposure and nonspecific binding of thirty-three central nervous system drugs in mice," *Drug Metab. Dispos.*, 33:175-181 (2005).

McCann et al., "Detection of carcinogens as mutagens in the Salmonella/microsome test: assay of 300 chemicals," *Proc. Natl. Acad. Sci. USA.*, 72:5135-5139 (1975).

McCann et al., "Detection of carcinogens as mutagens in the Salmonella/microsome test: assay of 300 chemicals: discussion," *Proc. Natl. Acad. Sci. USA*, 73:950-954 (1976).

Meredith et al., "P-Glycoprotein Efflux and Other Factors Limit Brain Amyloid β Reduction by β-Site Amyloid Precursor Protein-Cleaving Enzyme 1 Inhibitors in Mice," *J. Pharmacol. Exp. Ther*, 326(2):502-513 (2008).

Middleton, "New fluorinating reagents. Dialkylaminosulfur fluorides," J. Org. Chem. 1975, 40:574-578.

Milstein and Stille, "A general, selective, and facile method for ketone synthesis from acid chlorides and organotin compounds catalyzed by palladium," J. Am. Chem. Soc. 1978, 100:3636-3638.

Miyaura and Suzuki, "Palladium-Catalyzed Cross-Coupling Reactions of Organoboron Compounds," Chem. Rev., 1995, 95(7):2457-2483.

Murata et al., "Novel Palladium(0)-Catalyzed Coupling Reaction of Dialkoxyborane with Aryl Halides: Convenient Synthetic Route to Arylboronates," J. Org. Chem. 1997, 62(19):6458-6459.

Nahm et al., N-Methoxy-N-Methylamides as Effective Acylating Agents, *Tetrahedron Lett.*, 22(39):3815-3818 (1981).

Nerdinger et al., "Combined Directed ortho Metalation/Suzuki—Miyaura Cross-Coupling Strategies. Regiospecific Synthesis of Chlorodihydroxybiphenyls and Polychlorinated Biphenyls," *J. Org. Chem.*, 72(16):5960-5967 (2007).

Nussbaumer et al., "Highly selective TFAA-cleavage of tertiary 2,4-dimethoxybenzylamines and its use in the synthesis of secondary amines," *Tetrahedron*, 47(26):4591-4602 (1991).

Parikh and Doering, "Sulfur trioxide in the oxidation of alcohols by dimethyl sulfoxide," J. Am. Chem. Soc., 1967, 89(21):5505-5507.

Patani and LaVoie, Bioisosterism: A Rational Approach in Drug Design, Chem. Rev. 1996, 96, pp. 3147-3176.

Pfitzner and Moffat, "A New and Selective Oxidation of Alcohols," J. Am. Chem. Soc., 1963, 85(19):3027-3028.

Prakash et al., "Perfluoroalkylation with Organosilicon Reagents," *Chem. Rev.*, 97:757-786 (1997).

Quach and Batey, "Ligand- and Base-Free Copper(II)-Catalyzed C-N Bond Formation: Cross-Coupling Reactions of Organoboron Compounds with Aliphatic Amines and Anilines," *Org. Lett.*, 5(23):4397-4400 (2003).

Rao et al., "Improved Synthesis of Mirtazapine," *Org. Prep. Proced. Int.*, 39(4):399-402 (2007).

Rolandsgard et al., "Stereoselective preparation of spirane bridged, sandwiched bisarenes," *Tetrahedron*, 61(16):4128-4140 (2005).

Romero et al., "Discovery, synthesis, and bioactivity of bis(heteroaryl)piperazines. 1. A novel class of non-nucleoside HIV-1 reverse transcriptase inhibitors," *J. Med. Chem.*, 37(7):999-1014 (1994).

Rosowsky et al., "Synthesis and biological activity of the 2-desamino and 2-desamino-2-methyl analogues of aminopterin and methotrexate," *J. Med. Chem.*, 34(1):227-234 (1991).

Sankaranarayanan et al., "First demonstration of cerebrospinal fluid and plasma A beta lowering with oral administration of a beta-site amyloid precursor protein-cleaving enzyme 1 inhibitor in nonhuman primates," *J. Pharmacol. Exp. Ther.*, 328:131-140 (2009).

Sankaranarayanan et al., "In Vivo β-Secretase 1 Inhibition Leads to Brain Aβ Lowering and Increased α-Secretase Processing of Amyloid Precursor Protein without Effect on Neuregulin-1," *J. Pharmacol. Exp. Ther*, 324(3):957-969 (2008).

Sapountzis et al., "Synthesis of Functionalized Nitroarylmagnesium Halides via an Iodine—Magnesium Exchange," *J. Org. Chem.*, 70(7):2445-2454 (2005).

Sase et al., "One-Pot Negishi Cross-Coupling Reactions of In Situ Generated Zinc Reagents with Aryl Chlorides, Bromides, and Triflates," J. Org. Chem., 2008, 73(18):7380-7382.

Satoh et al., "Synthesis of 4-substituted phenylalanine derivatives by cross-coupling reaction of p-boronophenylalanines," Tet. Lett. 1997, 38(44):7645-7648.

Scheuner et al., "Secreted amyloid β-protein similar to that in the senile plaques of Alzheimer's disease is increased in vivo by the presenilin 1 and 2 and APP mutations linked to familial Alzheimer's disease," *Nature Medicine*, 2(8):864-870 (1996).

Schinkel, "P-Glycoprotein, a gatekeeper in the blood-brain barrier," *Adv. Drug Deliv. Rev.*, 36:179-194 (1999).

Schwizer et al., "Antagonists of the myelin-associated glycoprotein: A new class of tetrasaccharide mimics," *Bioorg. Med. Chem.*, 14:4944-4957 (2006).

Selles and Mueller, "Expedient Synthesis of Highly Substituted Fused Heterocoumarins," *Org. Lett.*, 6(2):277-279 (2004).

Shao et al., "4-(2-Pyridyl)piperazine-1-benzimidazoles as potent TRPV1 antagonists," *Bioorg. Med. Chem. Lett.*, 15(3):719-723 (2005).

Shing et al., "Intramolecular nitrile oxide-alkene cycloaddition of sugar derivatives with unmasked hydroxyl group(s)," *Org. Lett.*, 9(5):753-756 (2007).

Singh et al., "Recent Advances in Nucleophilic Fluorination Reactions of Organic Compounds Using Deoxofluor and DAST," Synthesis, 2002, 17:2561-2578.

Soderberg, Section 13.1: Tautomers—Chemwiki, retrieved on Oct. 30, 2013 http://chemwiki.ucdavis.edu/Organic_Chemistry/Organic_Chemistry_With_a_Biological_Emphasis/Chapter_13%03A_Reactions_with_stabilized_carbanion_intermediates_1/Section_13.1%3A_Tautomers, 5 pages.

Stille et al., "4-Methoxy-4'-Nitrobiphenyl," Org. Synth., 1998, Coll. vol. 9:553.

Stille, "The Palladium-Catalyzed Cross-Coupling Reactions of Organotin Reagents with Organic Electrophiles [New Synthetic Methods (58)]," Angew. Chem. Int. Ed. Engl. 1986, 25:508-524.

Summerfield et al., "Central nervous system drug disposition: the relationship between in situ brain permeability and brain free fraction," *J. Pharmacol. Exp. Ther.*, 322:205-213 (2007).

Suzuki, "Recent advances in the cross-coupling reactions of organoboron derivatives with organic electrophiles, 1995-1998," J Organometallic Chem. 1999, 576, 147-168.

Suzuki, "Synthetic studies via the cross-coupling reaction of organoboron derivatives with organic halides," Pure Appl. Chem. 1991, 63, 419-422.

Suzuki, "Cross-coupling Reactions of Organoboron Compounds with Organice Halides," Metal-Catalyzed Cross-Coupling Reactions 1998, 49-97.

Tamao et al., "Selective carbon-carbon bond formation by cross-coupling of Grignard reagents with organic halides. Catalysis by nickel-phosphine complexes," J. Am. Chem. Soc. 1972, 94 (12):4374-4376.

(56) References Cited

OTHER PUBLICATIONS

Tamayo et al., Design and synthesis of potent pyridazine inhibitors of p38 MAP kinase, *Bioorg. Med. Chem. Lett*.,15(9):2409-2413 (2005).

Tao et al., "Copper-catalyzed synthesis of aryl azides and 1-aryl-1,2,3-triazoles from boronic acids," *Tetrahedron Lett*., 48:3525-3529 (2007).

Tidewell, "Oxidation of Alcohols by Activated Dimethyl Sulfoxide and Related Reactions: An Update," Synthesis, 1990, 857-870.

Tidwell, "Oxidation of Alcohols to Carbonyl Compounds via Alkoxysulfonium Ylides: The Moffatt, Swern, and Related Oxidations," Org. React. 1990, 39:297-572.

Trainor, "The importance of plasma protein binding in drug discovery," *Expert Opin. Drug Discov*., 2:51-64 (2007).

Tzschucke et al., "Arenes to Anilines and Aryl Ethers by Sequential Iridium-Catalyzed Borylation and Copper-Catalyzed Coupling," *Org. Lett*., 9(5):761-764 (2007).

Tzvetkov et al., Synthesis and photoinitiated radical cyclization of allyl- and propynyloxymethyl substituted cyclopentanones to tetrahydrocyclopenta[c]furanols, *Tetrahedron Lett*., 46(45):7751-7755 (2005).

Ueno, "Molecular anatomy of the brain endothelial barrier: an overview of the distributional features," *Curr. Med. Chem*., 14:1199-1206 (2007).

Uno et al., "Reaction of 2-Isoxazolines with Organolithiums in the Presence of Boron Trifluoride," *Bull. Chem. Soc. Jpn*., 66:2730-2737 (1993).

Vedejs et al., "Enantiocontrolled Synthesis of (1S,2S)-6-Desmethyl-(methylaziridino)mitosene," *J. Am. Chem. Soc*., 122(22):5401-5402 (2000).

Vedejs et al., "Synthetic Enantiopure Aziridinomitosenes: Preparation, Reactivity, and DNA Alkylation Studies," *J. Am. Chem. Soc*., 125(51):15796-15806 (2003).

Watanabe et al., "A convenient method for the synthesis of $\Delta$1,6-bicyclo[4.n.0]alken-2-ones," *Tetrahedron Lett*., 40(46):8133-8136 (1999).

Whisler et al., "Synthetic applications of lithiated N-Boc allylic amines as asymmetric homoenolate equivalents," *J. Org. Chem*., 68:1207-1215 (2003).

Willis and Strongin, "Palladium-catalyzed cross-coupling of aryldiazonium tetrafluoroborate salts with arylboronic esters," Tet. Lett. 2000, 41(33):6271-6274.

Zhou and Fu, "Palladium-Catalyzed Negishi Cross-Coupling Reactions of Unactivated Alkyl Iodides, Bromides, Chlorides, and Tosylates," J. Am. Chem. Soc., 2003, 125(41):12527-12530.

A Typical Chromatogram from a Chiral HPLC Isolation of Compound 4-(9)
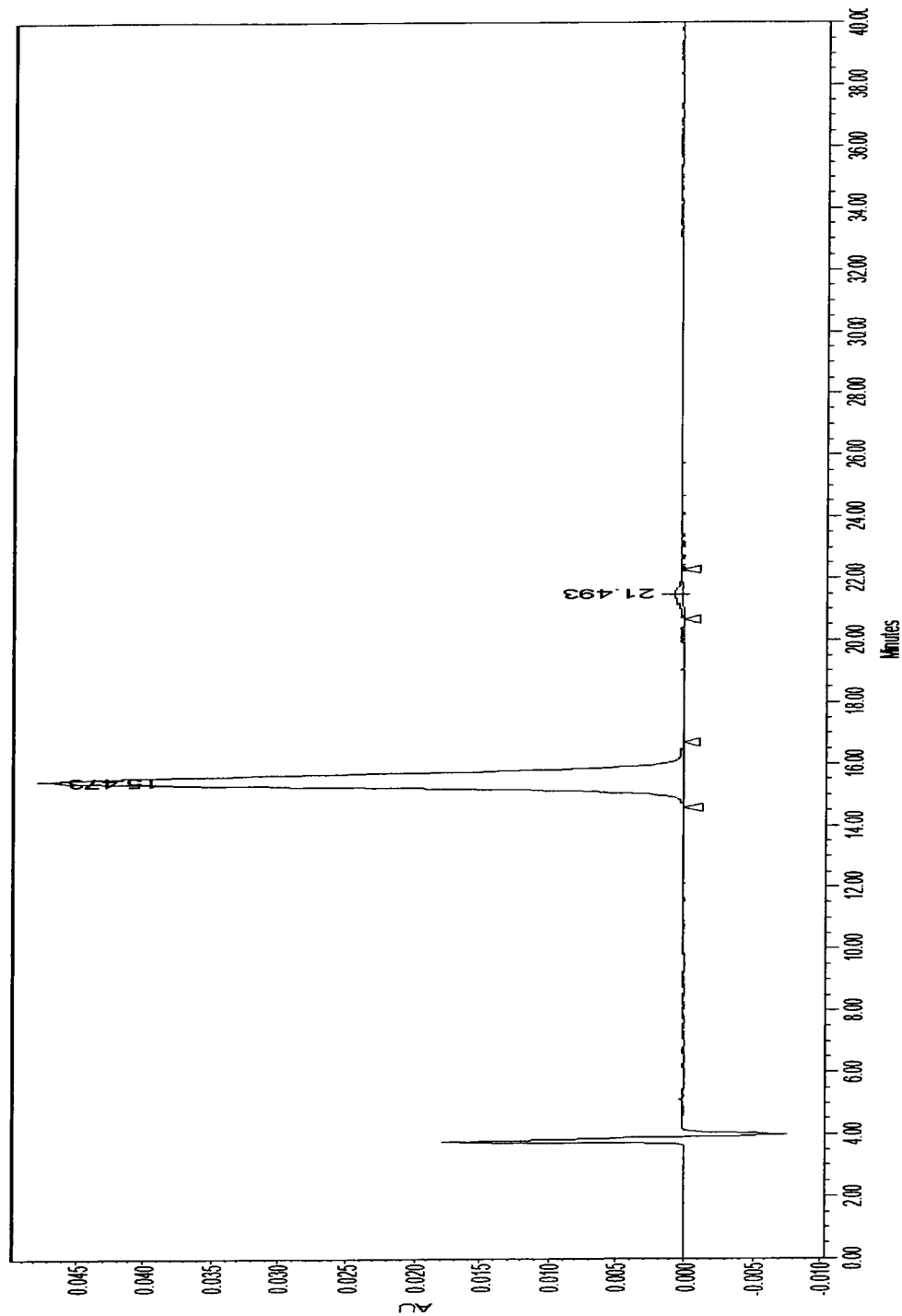

FUSED AMINODIHYDROTHIAZINE DERIVATIVES

The present invention relates to a fused aminodihydrothiazine derivative and pharmaceutical use thereof. More particularly, the present invention relates to a fused aminodihydrothiazine derivative which has an amyloid-β (hereinafter referred to as Aβ) protein production inhibitory effect or a beta-site amyloid-β precursor protein cleavage enzyme 1 (hereinafter referred to as BACE1 or beta-secretase) inhibitory effect and is effective for treating a neurodegenerative disease caused by Aβ protein, in particular, Alzheimer-type dementia, Down's syndrome or the like, and to a pharmaceutical composition comprising the fused aminodihydrothiazine derivative as an active ingredient.

Alzheimer's disease is a disease characterized by degeneration and loss of neurons as well as formation of senile plaques and neurofibrillary tangles. Currently, only the symptoms of Alzheimer's disease are treated using a symptom-improving agent typified by an acetylcholinesterase inhibitor, and a fundamental remedy to inhibit progression of the disease has not yet been developed. It is necessary to develop a method for controlling the cause of the onset of pathology in order to create a fundamental remedy for Alzheimer's disease.

It is assumed that Aβ-proteins as breakdown products of amyloid precursor proteins (hereinafter referred to as APP) are highly involved in degeneration and loss of neurons and onset of symptoms of dementia. AP-proteins have, as main components, Aβ40 consisting of 40 amino acids and Aβ42 with two amino acids added at the C-terminal. The Aβ40 and Aβ42 are known to be highly prone to aggregation and to be the main components of senile plaques. Further, it is known that the Aβ40 and Aβ42 are increased by mutations in APP and presenilin genes which is observed in familial Alzheimer's disease. Accordingly, a compound that reduces production of Aβ40 and Aβ42 is expected to be a disease progression inhibitor or prophylactic agent for Alzheimer's disease.

Aβ is produced by the cleavage of APP by beta-secretase (BACE1) and subsequently by gamma-secretase. For this reason, attempts have been made to create gamma-secretase and beta-secretase inhibitors in order to inhibit Aβ production.

Published International patent application WO2011/005738 (Eli Lilly and Company) describes compounds of formula (A) and their use as BACE inhibitors:

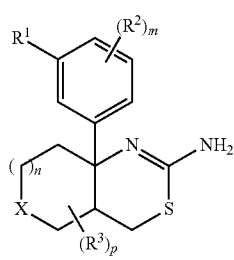

(A)

where $R^1$, $R^2$, $R^3$, X, m, n and p are defined therein.

Fused aminodihydrothiazine compounds of formula (B) have already been disclosed in published International patent application WO2009/091016 (Eisai R&D Management Co., Ltd.):

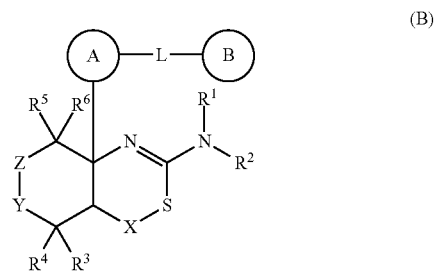

(B)

wherein ring A represents a $C_{6-14}$aryl group or the like; L represents —NR$^e$CO— [wherein R$^e$ represents a hydrogen atom or the like] or the like; ring B represents a $C_{6-14}$aryl group or the like; X represents a $C_{1-3}$alkylene group or the like; Y represents a single bond or the like; Z represents a $C_{1-3}$alkylene group or the like; $R^1$ and $R^2$ independently represent a hydrogen atom or the like; and $R^3$, $R^4$, $R^5$ and $R^6$ independently represent a hydrogen atom, a halogen atom or the like.

Further fused aminodihydrothiazine compounds of formula (C) have been disclosed in published International patent application WO2010/038686 (Eisai R&D Management Co., Ltd.):

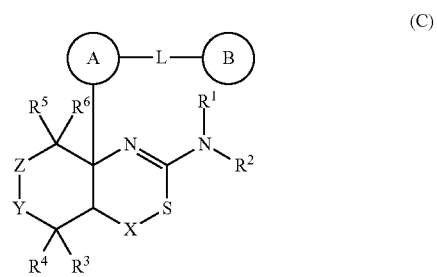

(C)

wherein ring A represents a $C_{6-14}$aryl group or the like; L represents —NR$^e$CO— [wherein R$^e$ represents a hydrogen atom or the like] or the like; the ring B represents a $C_{6-14}$aryl group or the like; X represents a $C_{1-3}$alkylene group or the like; Y represents a single bond or the like; Z represents an oxygen atom or the like; $R^1$ and $R^2$ each independently represents a hydrogen atom or the like; and $R^3$, $R^4$, $R^5$ and $R^6$ each independently represents a hydrogen atom, a halogen atom or the like.

The present invention represents a selection from the genus of compounds disclosed in WO2009/091016.

An object of the present invention is to provide further compounds that have an Aβ production inhibitory effect or a BACE1 inhibitory effect and are useful as prophylactic or therapeutic agents for a neurodegenerative disease caused by Aβ and typified by Alzheimer-type dementia, which compounds are fused aminodihydrothiazine derivatives.

Thus, the present invention provides a compound of formula (I):

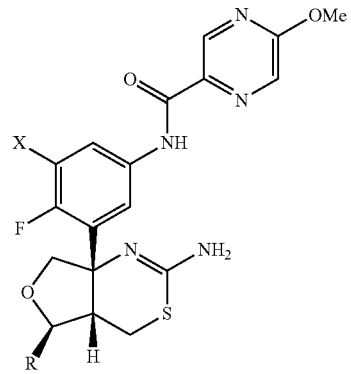

wherein
X is hydrogen or fluorine;
R is monofluoromethyl or difluoromethyl;
and pharmaceutically acceptable salts thereof.
In one embodiment of the present invention, X is hydrogen.
In another embodiment of the present invention, R is monofluoromethyl.
Specific compounds of the present invention are:
N-(3-((4aS,5S,7aS)-2-amino-5-(difluoromethyl)-4a,5,7,7a-tetrahydro-4H-furo[3,4-d][1,3]thiazin-7a-yl)-4,5-difluorophenyl)-5-methoxypyrazine-2-carboxamide:

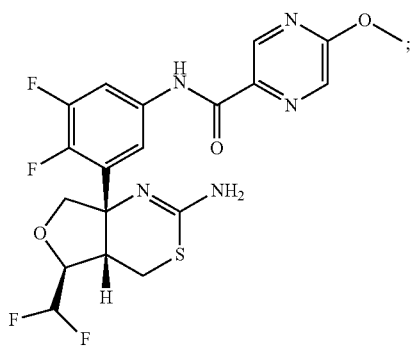 [SMILES: COc1cnc(C(=O)Nc2cc(F)c(F)c([C@]34CO[C@H](C(F)F)[C@H]3CSC(N)=N4)c2)cn1]

N-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-5-methoxypyrazine-2-carboxamide:

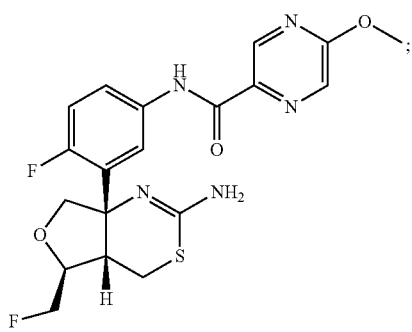 [SMILES: COc1cnc(C(=O)Nc2ccc(F)c([C@]34CO[C@H](CF)[C@H]3CSC(N)=N4)c2)cn1]

N-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-5-methoxypyrazine-2-carboxamide:

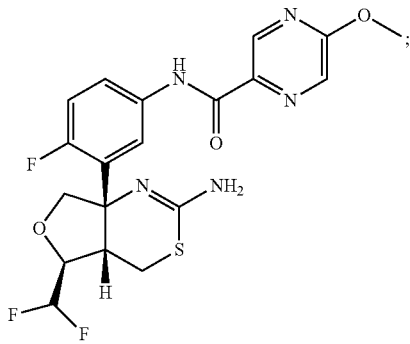 [SMILES: COc1cnc(C(=O)Nc2ccc(F)c([C@]34CO[C@H](C(F)F)[C@H]3CSC(N)=N4)c2)cn1]

N-(3-((4aS,5S,7aS)-2-amino-5-(fluoromethyl)-4a,5,7,7a-tetrahydro-4H-furo[3,4-d][1,3]thiazin-7a-yl)-4,5-difluorophenyl)-5-methoxypyrazine-2-carboxamide:

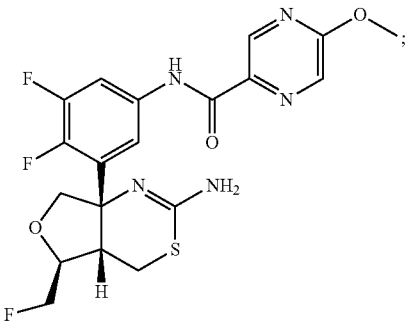 [SMILES: COc1cnc(C(=O)Nc2cc(F)c(F)c([C@]34CO[C@H](CF)[C@H]3CSC(N)=N4)c2)cn1]

and pharmaceutically acceptable salts thereof.

In one embodiment, the present invention provides a compound which is N-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-5-methoxypyrazine-2-carboxamide, or a pharmaceutically acceptable salt thereof In one embodiment, the present invention provides a compound which N-(3-((4aS,5S,7aS)-2-amino-5-(fluoromethyl)-4a,5,7,7a-tetrahydro-4H-furo[3,4-d][1,3]thiazin-7a-yl)-4,5-difluorophenyl)-5-methoxypyrazine-2-carboxamide, or a pharmaceutically acceptable salt thereof.

The compound of formula (I) is not limited to a specific isomer and includes all possible isomers (such as a keto-enol isomer, an imine-enamine isomer, a diastereoisomer and a rotamer) and mixtures thereof. For example, the compound of formula (I) includes the following tautomers:

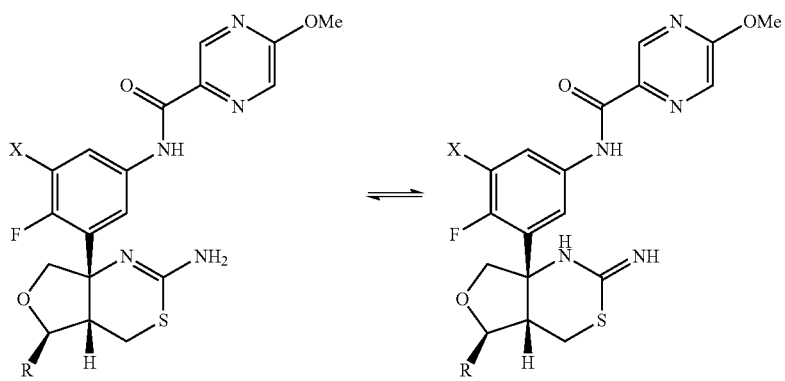

The compounds of the present invention contain three chiral centers located on the tetrahydrofuro-thiazinyl ring within formula (I). The stereochemical configuration at each of these chiral centers is preferably S, i.e. they are (4aS,5S,7aS) stereoisomers. For the avoidance of doubt the (4aS,5S,7aS) stereoisomers of the present invention may be present as a mixture with one or more of the other possible stereoisomers, for example in a racemic mixture.

In one embodiment, the present invention provides a compound of formula (I) which is stereochemically pure at the (4aS,5S,7aS) chiral centers. In the context of the present specification, the term stereochemically pure denotes a compound which has 80% or greater by weight of the (4aS,5S,7aS) stereoisomer and 20% or less by weight of other stereoisomers. In a further embodiment, the compound of formula (I) has 90% or greater by weight of the (4aS,5S,7aS) stereoisomer and 10% or less by weight of other stereoisomers. In a yet further embodiment, the compound of formula (I) has 95% or greater by weight of the (4aS,5S,7aS) stereoisomer and 5% or less by weight of other stereoisomers. In a still further embodiment, the compound of formula (I) has 97% or greater by weight of the (4aS,5S,7aS) stereoisomer and 3% or less by weight of other stereoisomers.

In the present specification, although crystal polymorphs of the compound may be present, the compound is similarly not limited thereto and may be present as a single crystal form or a mixture of single crystal forms. The compound may be an anhydride or a hydrate. Any of these forms is included in the claims of the present specification.

The present invention also includes isotopically-labelled compounds, which are identical to the compounds of formula (I), except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, fluorine, phosphorous, chlorine, technetium and iodine such as $^2$H, $^3$H, $^{11}$C, $^{14}$C, $^{13}$N, $^{15}$O, $^{18}$F, $^{32}$P, $^{99m}$Tc, $^{123}$I and $^{131}$I.

Compounds of the present invention and pharmaceutically acceptable derivatives (e.g. salts) of said compounds that contain the aforementioned isotopes and/or other isotopes of other atoms are within the scope of the present invention. Isotopically-labelled compounds of the present invention, for example those into which radioactive isotopes such as $^3$H and/or $^{14}$C are incorporated, are useful in drug and/or substrate tissue distribution assays. $^3$H and $^{14}$C are considered useful due to their ease of preparation and detectability. $^{11}$C, $^{15}$O and $^{18}$F isotopes are considered useful in PET (positron emission tomography), and $^{99m}$Tc, $^{123}$I and $^{131}$I isotopes are considered useful in SPECT (single photon emission computerized tomography), all useful in brain imaging. Substitution with heavier isotopes such as $^2$H can afford certain therapeutic advantages resulting from greater metabolic stability, for example increased in vivo half-life or reduced dosage requirements and, hence, are considered useful in some circumstances. Isotopically labelled compounds of formula (I) of this invention can generally be prepared by carrying out the procedures disclosed in the Schemes and/or in the Examples below, by substituting a readily available isotopically labelled reagent for a non-isotopically labelled reagent.

The fused aminodihydrothiazine derivative of the formula (I) according to the present invention may be a pharmaceutically acceptable salt. Pharmaceutically acceptable salts include those described by Berge, Bighley and Monkhouse, J. Pharm. Sci., 1977, 766, 1-19. Specific examples of the pharmaceutically acceptable salt include inorganic acid salts (such as sulfates, nitrates, perchlorates, phosphates, carbonates, bicarbonates, hydrofluorides, hydrochlorides, hydrobromides and hydroiodides), organic carboxylates (such as acetates, oxalates, maleates, tartrates, fumarates, citrates, malonates and lactates), organic sulfonates (such as methanesulfonates, trifluoromethanesulfonates, ethanesulfonates, benzenesulfonates, toluenesulfonates and camphorsulfonates), amino acid salts (such as aspartates and glutamates), quaternary amine salts, alkali metal salts (such as sodium salts and potassium salts) and alkali earth metal salts (such as magnesium salts and calcium salts).

The compound of the formula (I) according to the present invention can be converted to a pharmaceutically acceptable salt by a conventional method where necessary. The salt can be prepared by a method in which methods typically used in the field of organic synthetic chemistry and the like are appropriately combined. Specific examples of the method include neutralization titration of a free solution of the compound of the present invention with an acid solution.

The fused aminodihydrothiazine derivative of formula (I) or pharmaceutically acceptable salt according to the present invention may be a solvate thereof. Examples of a solvate include a hydrate.

The compound of formula (I) according to the present invention can be converted to a solvate by subjecting the compound to a solvate forming reaction known per se where necessary.

The present invention further provides a compound of formula (I) or a pharmaceutically acceptable salt thereof for use in therapy.

The fused aminodihydrothiazine derivative or pharmaceutically acceptable salt thereof according to the present invention has an excellent Aβ production inhibitory effect or BACE1 inhibitory effect and is useful as a prophylactic or therapeutic agent for a neurodegenerative disease caused by Aβ and typified by Alzheimer-type dementia. The compounds of the invention reduce both Aβ40 and Aβ42. Furthermore, the compounds of the present invention may have a BACE 2 inhibitory effect.

Thus, in another aspect, the present invention provides a compound of formula (I) as defined above, or a pharmaceutically acceptable salt thereof, for inhibiting production of amyloid-β protein.

In a further aspect, the present invention provides a compound of formula (I) as defined above, or a pharmaceutically acceptable salt thereof, for inhibiting beta-site amyloid-β precursor protein cleaving enzyme 1 (BACE 1).

In a further aspect, the present invention provides a compound of formula (I) as defined above, or a pharmaceutically acceptable salt thereof, for treating a neurodegenerative disease. Examples of neurodegenerative diseases include Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD. In one embodiment, the neurodegenerative disease is Alzheimer-type dementia (AD).

In another aspect, the invention provides the use of a compound of formula (I) as defined above, or a pharmaceutically acceptable salt thereof, for the manufacture of a medicament for the treatment or prevention of a neurodegenerative disease such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD. In one embodiment, the neurodegenerative disease is Alzheimer-type dementia or Down's syndrome. In another embodiment, the neurodegenerative disease is Alzheimer-type dementia (AD).

In another aspect, the invention provides the use of a compound of formula (I) as defined above, or a pharmaceutically acceptable salt thereof, for the manufacture of a medicament for the treatment or prevention of a neurodegenerative disease, such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD. In one embodiment, the neurodegenerative disease is Alzheimer-type dementia (AD).

In another aspect, the invention provides a method of inhibiting production of amyloid-β protein and/or of treating or preventing a neurodegenerative disease, such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD, involving administering to a human subject suffering from the condition a therapeutically or prophylactically effective amount of a compound of formula (I) or a pharmaceutically acceptable salt thereof. Examples of neurodegenerative diseases include those listed above. In one embodiment, the neurodegenerative disease is Alzheimer-type dementia (AD). "Effective amount" means an amount sufficient to cause a benefit to the subject or at least to cause a change in the subject's condition.

Additional conditions which may be treated by the compounds of the present invention include type 2 diabetes, Creutzfield-Jakob Disease (CJD), peripheral nerve injury, peripheral neuropathy, progressive supra-nuclear palsy, stroke, amyotrophic lateral sclerosis (ALS), autoimmune diseases, inflammation, arterial thrombosis, anxiety disorders, psychotic disorders, epilepsy, seizures, convulsions, stress disorders, vascular amyloidosis, pain, Gerstmann-Straeussler-Scheinker syndrome, scrapie, encephalopathy, spino cerebellar ataxia, Wilson's Disease, Graves Disease, Huntington's Disease, Whipple's Disease, Kostmann Disease, glaucoma, hereditary cerebral hemorrhage with amyloidosis, cerebral hemorrhage with amyloidosis, vascular amyloidosis, brain inflammation, fragile X syndrome, stroke, Tourette's syndrome, inclusion body myositis, stress disorders, depression, bipolar disorder and obsessive compulsive disorder.

In one aspect the present invention further provides a compound of formula (I) as defined above, or a pharmaceutically acceptable salt thereof, for treating type 2 diabetes. In a further aspect the present invention further provides the use of a compound of formula (I) as defined above, or a pharmaceutically acceptable salt thereof, for the manufacture of a medicament for the treatment or prevention of type 2 diabetes. In a yet further aspect the present invention further provides a method of inhibiting production of amyloid-β protein and/or of treating or preventing type 2 diabetes involving administering to a human subject suffering from the condition a therapeutically or prophylactically effective amount of a compound of formula (I) or a pharmaceutically acceptable salt thereof.

A further aspect of the invention provides a pharmaceutical composition comprising a compound of formula (I) as defined above, or a pharmaceutically acceptable salt thereof, as active ingredient in association with a pharmaceutically acceptable carrier. The composition may be in any suitable form, depending on the intended method of administration. It may for example be in the form of a tablet, capsule or liquid for oral administration, or of a solution or suspension for administration parenterally.

The fused aminodihydrothiazine derivative or pharmaceutically acceptable salt thereof according to the present invention can be formulated by a conventional method. Preferable examples of the dosage form include tablets, coated tablets such as film tablets and sugar-coated tablets, fine granules, granules, powders, capsules, syrups, troches, inhalants, suppositories, injections, ointments, eye drops, nasal drops, ear drops, cataplasms and lotions.

These solid preparations such as tablets, capsules, granules and powders can contain generally 0.01 to 100 wt %, and preferably 0.1 to 100 wt % of the fused aminodihydrothiazine derivative or pharmaceutically acceptable salt thereof according to the present invention as an active ingredient.

The active ingredient is formulated by blending ingredients generally used as materials for a pharmaceutical preparation and adding an excipient, a disintegrant, a binder, a lubricant, a colorant and a corrective typically used, and adding a stabilizer, an emulsifier, an absorbefacient, a surfactant, a pH adjuster, a preservative and an antioxidant where necessary, for example, using a conventional method. Examples of such ingredients include animal and vegetable oils such as soybean oil, beef tallow and synthetic glyceride; hydrocarbons such as liquid paraffin, squalane and solid paraffin; ester oils such as octyldodecyl myristate and isopropyl myristate; higher alcohols such as cetostearyl alcohol and behenyl alcohol; a silicone resin; silicone oil; surfactants such as polyoxyethylene fatty acid ester, sorbitan fatty acid ester, glycerol fatty acid ester, polyoxyethylene sorbitan fatty acid ester, polyoxyethylene hydrogenated castor oil and a polyoxyethylene-polyoxypropylene block copolymer; water-soluble polymers such as hydroxyethylcellulose, polyacrylic acid, a carboxyvinyl polymer, polyethylene glycol, polyvinylpyrrolidone and methylcellulose; lower alcohols such as ethanol and isopropanol; polyhydric alcohols such as glycerol, propylene glycol, dipropylene glycol and sorbitol; sugars such as glucose and sucrose; inorganic powders such as silicic anhydride, magnesium aluminum silicate and aluminum silicate; and purified water. Examples of the excipient used include lactose, corn starch, saccharose, glucose, mannitol, sorbitol, crystalline cellulose and silicon dioxide. Examples of the binder used include polyvinyl alcohol, polyvinyl ether, methylcellulose, ethylcellulose, gum arabic, tragacanth, gelatin, shellac, hydroxypropylmethylcellulose, hydroxypropylcellulose, polyvinylpyrrolidone, a polypropylene glycol-polyoxyethylene block copolymer and meglumine. Examples of the disintegrant used include starch, agar, gelatin powder, crystalline cellulose, calcium carbonate, sodium bicarbonate, calcium citrate, dextrin, pectin and carboxymethylcellulose calcium. Examples of the lubricant used include magnesium stearate, talc, polyethylene glycol, silica and hydrogenated vegetable oil. Examples of the colorant used include those permitted to be added to pharmaceuticals. Examples of the corrective used include cocoa powder, menthol, empasm, mentha oil, borneol and cinnamon powder. Obviously, the ingredients are not limited to the above additive ingredients.

For example, an oral preparation is prepared by adding the fused aminodihydrothiazine derivative or pharmaceutically acceptable salt thereof according to the present invention as an active ingredient, an excipient and, where necessary, a binder, a disintegrant, a lubricant, a colorant, a corrective and the like, and then forming the mixture into powder, fine granules, granules, tablets, coated tablets, capsules or the like by a conventional method. Obviously, tablets or granules may be appropriately coated, for example, sugar coated, where necessary.

For example, a syrup or an injection preparation is prepared by adding a pH adjuster, a solubilizer, an isotonizing agent and the like, and a solubilizing agent, a stabilizer and the like where necessary by a conventional method. The injection may be a previously prepared solution, or may be powder itself or powder containing a suitable additive, which is dissolved before use. The injection can contain usually 0.01 to 100 wt %, and preferably 0.1 to 100 wt % of the active ingredient. Further, a liquid preparation for oral administration such as a suspension or a syrup can contain usually 0.01 to 100 wt %, and preferably 0.1 to 100 wt % of the active ingredient.

For example, an external preparation can be prepared by any conventional method without specific limitations. As a base material, any of various materials usually used for a pharmaceutical, a quasi drug, a cosmetic or the like can be used. Examples of the base material include materials such as animal and vegetable oils, mineral oils, ester oils, waxes, higher alcohols, fatty acids, silicone oils, surfactants, phospholipids, alcohols, polyhydric alcohols, water-soluble polymers, clay minerals and purified water. A pH adjuster, an antioxidant, a chelator, a preservative and fungicide, a colorant, a flavor or the like can be added where necessary. Further, ingredients such as an ingredient having a differentiation inducing effect, a blood flow enhancer, a bactericide, an antiphlogistic, a cell activator, vitamin, amino acid, a humectant and a keratolytic agent can be blended where necessary.

The dose of the fused aminodihydrothiazine derivative or pharmaceutically acceptable salt thereof according to the present invention varies according to the degree of symptoms, age, sex, body weight, mode of administration, type of salt and specific type of disease, for example. Typically, the active ingredient is orally administered to an adult at about 30 µg to 10 g, preferably 100 µg to 5 g, and more preferably 100 µg to 1 g per day, or is administered to an adult by injection at about 30 µg to 1 g, preferably 100 µg to 500 mg, and more preferably 100 µg to 300 mg per day, in one or several doses, respectively.

Compounds of formula (I) may be used in combination with other therapeutic agents, for example medicaments claimed to be useful as either disease modifying or symptomatic treatments of a neurodegenerative disease such as Alzheimer's disease. Thus, in a further aspect, the present invention provides a pharmaceutical product comprising, in combination, a first active ingredient which is a compound of formula (I) or a pharmaceutically acceptable salt thereof and at least one further active ingredient useful in treating a neurodegenerative disease. In one embodiment of the invention, the neurodegenerative disease is Alzheimer-type dementia (AD). Suitable examples of such further active ingredients may be symptomatic agents, for example those known to modify cholinergic transmission such as M1 and M3 muscarinic receptor agonists or allosteric modulators, M2 muscarinic antagonists, M4 agonists or positive allosteric modulators (PAMs), acetylcholinesterase inhibitors (such as tetrahydroaminoacridine, donepezil hydrochloride and rivastigmine), nicotinic receptor agonists or allosteric modulators (such as $\alpha 7$ agonists or allosteric modulators or $\alpha 4\beta 2$ agonists or allosteric modulators), PPAR agonists (such as PPAR$\gamma$ agonists), 5-HT$_4$ receptor agonists or partial agonists, histamine H3 antagonists, 5-HT$_6$ receptor antagonists or 5HT$_{1A}$ receptor ligands and NMDA receptor antagonists or modulators, 5-HT$_{2A}$ antagonists, 5-HT$_7$ antagonists, D1 agonists or PAMs, D4 agonists or PAMs, D5 agonists or PAMs, GABA-A $\alpha 5$ inverse agonists or negative allosteric modulators (NAMs), GABA-A $\alpha 2/3$ agonists or PAMs, mGluR2 modulators (PAMs or NAMs), mGluR3 PAMs, mGluR5 PAMs, PDE 1 inhibitors, PDE 2 inhibitors, PDE 4 inhibitors, PDE 5 inhibitors, PDE 9 inhibitors, PDE 10 inhibitors, GlyT1 inhibitors, DAAO inhibitors, ASC1 inhibitors, AMPA modulators, SIRT1 activators or inhibitors, AT4 antagonists, GalR1 antagonists, GalR3 ligands, adenosine A1 antagonists, adenosine A2a antagonists, $\alpha 2A$ antagonists or agonists, selective and unselective norepinephrine reuptake inhibitors (SNRIs), or potential disease modifying agents such as gamma secretase inhibitors or modulators, alpha secretase activators or modulators, amyloid aggregation inhibitors, amyloid antibodies, tau aggregation inhibitors or tau phosphorylation/kinase inhibitors, tau dephosphorylation/phosphatase activators, mitogen-activated protein kinase kinase 4 (MKK4/MEK4/MAP2K4) inhibitors, c-Jun N-terminal kinase (JNK) inhibitors, casein kinase inhibitors, MK2 (mitogen activated protein kinase-activated protein kinase 2) inhibitors, MARK (microtubule affinity regulating kinase) inhibitors, CDK5 (cyclin dependent kinase 5) inhibitors, GSK-3 (glycogen synthase kinase-3) inhibitors and tau-tubulin kinase-1 (TTBK1) inhibitors. Further examples of such other therapeutic agents may be calcium channel blockers, HMG-CoA (3-hydroxy-3-methyl-glutaryl-CoA) reductase inhibitors (statins) and lipid lowering agents, NGF (nerve growth factor) mimics, antioxidants, GPR3 ligands, plasmin activators, neprilysin (NEP) activators, IDE (insulin degrading enzyme) activators, melatonin MT1 and/or MT2 agonists, TLX/NR2E1 (tailless X receptor) ligands, GluR1 ligands, RAGE (receptor for advanced glycation end-products) antagonists, EGFR (epidermal growth factor receptor) inhibitors, FPRL-1 (formyl peptide-like receptor-1) ligands, GABA antagonists, and MICAL (molecule interacting with casL) inhibitors, e.g. oxoreductase inhibitors, CB 1 antagonists/inverse agonists, non-steroidal anti-inflammatory drugs (NSAIDs), anti-inflammatory agents (for example agents that could be used to treat neuroinflammation either by enhancing or reducing neuroinflammation), amyloid precursor protein (APP) ligands, anti-amyloid vaccines and/or antibodies, agents that promote or enhance amyloid efflux and/or clearance, histone deacetylase (HDAC) inhbitors, EP2 antagonists, 11-beta HSD1 (hydroxysteroid dehydrogenase) inhibitors, liver X receptor (LXR) agonists or PAMs, lipoprotein receptor-related protein (LRP) mimics and/or ligands and/or enhancers and/or inhibitors, butyryl cholinesterase inhibitors, kynurinic acid antagonists and/or inhibitors of kynurenine aminotransferease (KAT), orphanin FQ/nociceptin (NOP)/opioid-like receptor 1 (ORL1) antagonists, excitatory amino acid transporter (EAAT) ligands (activators or inhibitors), and plasminogen activator inhibitor-1 (PAI-1) inhibitors, niacin and/or GPR109 agonists or PAMs in combination with cholesterol lowering agents and/or HMGCoA reductase inhibitors (statins), dimebolin or similar agents, antihistamines, metal binding/chelating agents, antibiotics, growth hormone secretagogues, cholesterol lowering agents, vitamin E, cholesterol absorption inhibitors, cholesterol efflux promoters and/or activators, and insulin upregulating agents.

In one embodiment, the present invention provides a pharmaceutical product comprising, in combination, a first active ingredient which is a compound of formula (I) or a pharmaceutically acceptable salt thereof and at least one further active ingredient selected from:—
cholinesterase inhibitors, e.g. donepezil, galantamine, rivastigamine, tetrahydroaminoacridine and pharmaceutically acceptable salts thereof,
5-$HT_6$ antagonists, e.g. SB-742457 and pharmaceutically acceptable salts thereof,
HMGCoA reductase inhibitors e.g. lovastatin, rosuvastatin, atorvastatin, simvastatin, fluvastatin, pitavastatin, pravastatin and pharmaceutically acceptable salts thereof.

The individual components of such combinations may be administered either sequentially or simultaneously in separate or combined pharmaceutical formulations. Consequently, the pharmaceutical product may, for example be a pharmaceutical composition comprising the first and further active ingredients in admixture. Alternatively, the pharmaceutical product may for example comprise the first and further active ingredients in separate pharmaceutical preparations suitable for simultaneous, sequential or separate administration to a patient in need thereof.

The combinations referred to above may conveniently be presented for use in the form of a pharmaceutical formulation and thus pharmaceutical formulations comprising a combination as defined above together with a pharmaceutically acceptable carrier or excipient comprise a further aspect of the invention.

When a compound of formula (I) or a pharmaceutically acceptable salt thereof is used in combination with a second therapeutic agent active, the dose of each compound may differ from that when the compound is used alone. Appropriate doses will be readily appreciated by those skilled in the art.

Thus, an additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

In one embodiment, the present invention provides a pharmaceutical composition comprising a compound of formula (I), one or more other agents for the treatment of Alzheimer's disease such as symptomatic agents, for examples those known to modify cholinergic transmission such as M1 and M3 muscarinic receptor agonists or allosteric modulators, M2 muscarinic antagonists, acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-$HT_4$ receptor agonists or partial agonists, histamine H3 antagonists, 5-$HT_6$ receptor antagonists or 5HT1A receptor ligands and NMDA receptor antagonists or modulators, 5-$HT_{2A}$ antagonists, 5-$HT_7$ antagonists, D1 agonists or positive allosteric modulators (PAMs), D4 agonists or PAMs, GABA-A α5 inverse agonists or negative allosteric modulators (NAMs), GABA-A α2/3 agonists or PAMs, mGluR2 modulators (PAMs or NAMs), mGluR3 PAM, mGluR5 PAM, PDE 1 inhibitors, PDE 2 inhibitors, PDE 4 inhibitors, PDE 5 inhibitors, PDE 9 inhibitors, PDE 10 inhibitors, GlyT1 inhibitors, DAAO inhibitors, ASC1 inhibitors, AMPA modulators, SIRT1 activators or inhibitors, AT4 antagonists, GalR1 antagonists, GalR3 ligands, adenosine A1 antagonists, adenosine Ata antagonists, α2A antagonists or agonists, selective and unselective norepinephrine reuptake inhibitors (SNRIs), or potential disease modifying agents such as gamma secretase inhibitors or modulators, alpha secretase activators or modulators, amyloid aggregation inhibitors, amyloid antibodies, tau aggregation inhibitors or tau phosphorylation inhibitors, in association with a pharmaceutically acceptable carrier. In a further embodiment the present invention provides a combination comprising a compound of formula (I) or a pharmaceutically acceptable salt thereof, together with a further therapeutic agent as described herein above for sequential or simultaneous administration in separate or combined pharmaceutical formulations.

In a further aspect, the invention provides a method of inhibiting production of amyloid-β protein and/or of treating or preventing a neurodegenerative disease, such as Alzheimer-type dementia (AD), Down's syndrome, cerebrovascular amyloid angiopathy (CAA), mild cognitive impairment (MCI), memory loss, presenile dementia, senile dementia, hereditary cerebral hemorrhage with amyloidosis, and other degenerative dementias such as dementias of mixed vascular and degenerative origin, dementia associated with supranuclear palsy, dementia associated with cortical basal degeneration, dementia associated with Parkinson's Disease (PD), and dementia associated with diffuse Lewy Body type of AD, the method involving administering to a human subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

Alzheimer's Disease (AD) is characterized pathologically by the presence of neurofibrillary tangles (NFTs) and plaques, consisting of amyloid (Aβ) peptides of varying length, for example 42 amino acids (Aβ42) and 40 amino acids (Aβ40). In addition to these pathological markers, brain atrophy is also evident. The build up of plaques is believed to be due to the aggregation of Aβ peptides. Aβ peptides are formed in the brain by the sequential cleavage of amyloid precursor protein (APP) by β-secretase (BACE-1) and γ-secretase. Therefore potential AD drugs aimed at inhibiting amyloid formation by inhibiting BACE-1 or γ-secretase, must be able to achieve adequate exposure in the brain, in order to exert an effect on AD.

Although BACE-1 represents an attractive target to halt or slow the production of amyloid peptides, various research groups have found it challenging to identify BACE-1 inhibitors that can penetrate the central nervous system (CNS) and thus inhibit the enzyme at the site of action.

The brain is protected by several barriers including the blood brain barrier (BBB) and transporters (Hitchcock and Pennington, J Med Chem 2006, 29, 7559; Ueno, Curr. Med. Chem. 2007, 14, 1199; Gloor et al., Brain Res. Rev. 2001, 36, 258). Several efflux transporters have been characterised which prevent compounds entering the brain. One of the best characterised and most prominent in preventing the CNS penetration of xenobiotics is P-glycoprotein (Pgp) (Kusuhara and Sugiyama, Drug Discovery Today, 2001, 6, 150; Mahar Doan et al., J. Pharm. Expt. Ther. 2002, 303, 1029; Lin, Drugs of Today 2004, 40, 5; Lin & Yamazaki, Clin Pharmacokinet. 2003, 42, 59; Schinkel, Adv. Drug Deliv. Rev. 1999, 36, 179). It has been shown that Pgp efflux is important for BACE-1 inhibitors (Hussain et al., J. Neurochem. 2007, 100, 802). Thus, overcoming Pgp efflux is important.

Those skilled in the art will appreciate that there are several ways to measure or predict CNS penetration in vitro or in vivo. The potential for CNS penetration can be assessed in vitro by determining whether a compound can be subjected to Pgp efflux, i.e. by conducting an in vitro Pgp assay. Those skilled in the art will appreciate that a number of cell lines can be used and that the choice of cell line may or may not affect the results of the assay.

Those skilled in the art will appreciate that in vitro Pgp assays are predictive assays of in vivo CNS penetration. Those skilled in the art will appreciate there are many ways to assess the CNS penetration of compounds in vivo. For example, one can quantify compound concentrations in blood or plasma and brain and calculate a brain:blood (Br:Bl) or brain:plasma (Br:Pl) ratio. This method has been used historically and has been widely accepted as a method of determining CNS penetration (Summerfield et al., J Pharmacol. Expt. Ther. 2007, 322, 205). Those skilled in the art will appreciate that this type of assay could be conducted at steady state, a single time point, multiple time points or could be done by quoting Area Under the Curve (AUC) ratios. All methods are equally valid but each may have certain caveats that will be appreciated by those skilled in the art. Recent literature has been published to suggest that it is important to consider the free concentrations in vivo and that when no efflux occurs from the brain the free plasma concentration should be the same or equivalent to the free brain concentration (Kalvass and Maurer Biopharmaceutics & Drug Disposition 2002, 23, 327; Mauer et al., Drug Metab. Disposition 2005, 33, 175; Trainor Expert Opin. Drug Discov. 2007, 2, 51). Thus, a compound that can freely penetrate the CNS and is not subjected to active efflux, for example by Pgp or another transporter, should demonstrate a free brain:free plasma ($Br_{fr}$:$Pl_{fr}$) or an unbound brain:unbound plasma ($Br_u$:$Pl_u$) of approximately 1:1. Those skilled in the art will appreciate that the free or unbound concentrations can be calculated by multiplying the total brain or total plasma concentration by the fraction unbound in brain tissue or plasma, which can be measured by the assay described below. Those skilled in the art will appreciate that the fraction unbound may change with experimental factors, for example concentration, or temperature, etc. Those skilled in the art will be able to assess this and select the most appropriate set of conditions. Those skilled in the art will also appreciate that as long as the conditions are the same for each compound screened then the assay will give consistent data for the range of compounds tested thus minimising any discrepancies. It has also been proposed that drug concentrations in cerebrospinal fluid (CSF) are equivalent to free brain concentrations for compounds which are not actively effluxed from the brain (He et al., Xenobiotica 2009, 39, 687). Thus another method of determining CNS penetration would be to assess the CSF:free plasma (CSF:$Pl_{fr}$) or CSF:unbound plasma (CSF:$Pl_u$). If the free drug in plasma is able to permeate into the CNS and is not actively influxed or effluxed then the CSF:$Pl_{fr}$ or CSF:$Pl_u$ should be approximately 1:1. Those skilled in the art will appreciate the issues associated with determining CSF drug concentrations and extracting CSF, for example CSF can be contaminated by blood depending on the method of withdrawal, also the CSF concentrations may be of lower accuracy, depending on the dose used.

Thus it has been shown that a BACE inhibitor from GlaxoSmithKline (GSK188909), BACE-1 $IC_{50}$ 5 nM, which has low CNS exposure was ineffective at lowering Aβ40 production in the brains of TASTPM mice (which overexpress both human APPswe$^{K595N/M5961}$ and PS-1$^{M146V}$) upon acute administration (Hussain et al., J. Neurochem. 2007, 100, 802-809). Following an oral dose of 250 mg/kg the brain concentration of GSK188909 in TASTPM mice was 0.62 uM. When a Pgp inhibitor (GF120918) was dosed 5 hours before the oral administration of GSK188909, the brain concentration of GSK188909 was found to be 5.43 uM following an oral dose of 250 mg/kg, i.e. the co-administration of a Pgp inhibitor caused an almost 9-fold increase in CNS penetration, showing Pgp efflux is an important mechanism in preventing BACE inhibitors from penetrating the CNS. Furthermore, in the absence of a Pgp inhibitor, a 250 mg/kg oral dose of GSK188909 did not have any effect on brain Aβ40 levels in TASTPM mice, whereas when a Pgp inhibitor was co-administered (5 hours prior to the administration of GSK188909) a 68% reduction in brain Aβ40 levels relative to vehicle-treated mice was observed.

Another paper has reported a similar effect with three BACE-1 inhibitors from Bristol-Myers Squibb (Meredith et al., J. Pharm. Expt. Ther. 2008, 326, 502-513). The three reported compounds were found to be Pgp substrates in vitro. When dosed to mice, the three compounds showed low CNS penetration and did not lower amyloid levels in the brain but were able to lower plasma amyloid levels. When the same three compounds were administered to Pgp knockout (KO) mice, the level of CNS penetration increased and the compounds were able to lower amyloid levels in the brain.

Researchers at Schering-Plough have also published papers (Iserloh et al., Bioorg. Med. Chem. Lett. 2008, 18, 418) to show that BACE-1 inhibitors from their series (e.g. example 11 from the aforementioned reference), are subject to Pgp efflux, as a result of which the compound was found to display a low Br:Pl (<0.1) in the rat.

The literature cited above emphasizes the difficulties in identifying BACE-1 inhibitors which are not subjected to Pgp efflux. Such inhibitors would be highly desirable and many research groups have attempted to discover such compounds without success. Thus BACE-1 inhibitors which are not Pgp substrates and can therefore readily penetrate the CNS and lower amyloid in the brain would be desirable.

More recently, researchers at Wyeth have reported extensive work to overcome Pgp efflux in a series of cyclic acylguanidine BACE-1 inhibitors (Malamas et al., Bioorg. Med. Chem. Lett. 2010, 20, 6597). Compounds were discovered that were weak Pgp substrates and with Br:Pl approaching 1:1. However, two lead examples with reduced Pgp efflux (84 and 89 from the aforementioned reference), did not lower Aβ40 in the brain of Tg2576 mice 8 hours after a 30 mg/kg oral dose. The lack of efficacy was attributed to the fact the compounds showed high brain tissue binding. Thus, it is important to discover BACE-1 inhibitors that are not Pgp substrates but still have a reasonable unbound fraction in brain tissue and are able to lower amyloid in the brain.

It has also been shown that BACE inhibitors that are not Pgp substrates in vitro, can penetrate the CNS (e.g. TC-1 from Merck), and can lower Aβ40 levels in the brain of APP-YAC mice and monkeys (Sankaranarayanan et al., J. Pharmacol. Expt. Ther. 2009, 328, 131-140). Thus, in vitro Pgp assays showed TC-1 not to be a Pgp substrate and when TC-1 was dosed to APP-YAC mice (100 mg/kg i.p.) it was able to modestly penetrate the CNS as shown by the brain concentrations and the brain:plasma ratio and this ability resulted in moderate lowering of brain amyloid.

| Time | Plasma conc. (μM) | Brain conc. (μM) | Br:Pl | Reduction in brain Aβ40 (%) |
|---|---|---|---|---|
| 2 h | 25 | 1.6 | 0.06 | 26 |
| 4 h | 13 | 1.8 | 0.14 | 29 |

Brain and plasma concentration of TC-1 following 100 mg/kg i.p. dose and corresponding effects on brain Ab40 levels, in APP-YAC mice.

In separate experiments it was shown that TC-1 could penetrate the CSF of monkeys when co-administered with a CYP3A4 inhibitor (ritonavir). In these experiments the average plasma concentration of TC-1 was found to be 2.7 uM, whilst the CSF concentration was found to be 0.025 uM. However, as TC-1 is ~99% bound to plasma proteins the free plasma concentration was calculated to be ~0.027 nM. It was found that CSF Aβ40 levels showed a 42% decrease relative to a vehicle treated control group. Thus, a BACE inhibitor that can freely penetrate the CNS would be expected to be able to lower amyloid levels in the CNS. It would be beneficial not to have to be co-dosed with a CYP3A4 inhibitor.

The compounds of the present invention have been shown to lower Aβ production in cellular assays which correlates with their ability to lower Aβ production in animals. Thus, the compounds of the present invention will have utility in lowering Aβ production in humans and thus will be useful in the treatment of neurodegenerative diseases such as Alzheimer's disease.

Rat In Vivo CNS Penetration

Male Sprague Dawley rats were acquired from Charles River UK Ltd. (Margate, UK) and housed according to UK Home Office guidelines. Drugs were made up to the appropriate concentrations in 0.5% methyl cellulose. Animals were dosed orally (2 mL/kg) by gavage at the doses outlined in Tables 1 to 4 below.

At the time points post-dosing, specified in the Tables 1 to 4 below the animals were administered an i.p. injection of sodium pentobarbitone (approximately 330 mg/kg for terminal anaesthesia).

Using a guillotine, the animals were decapitated and trunk blood collected into 15 ml Falcon tubes containing 100 IU heparin. Blood was vortexed followed by centrifugation at 6000 rpm, 4° C. for 5 minutes. Plasma was collected for DMPK and ELISA assays and stored at −80° C. until use. Brains were dissected out and divided along the midline, weighed and stored at −80° C. until further use.

Method for Analysis of Plasma, Brain and CSF Samples
Preparation of Acetonitrile Working Solutions Test compound was prepared as a 1 mg free base/mL solution in DMSO, vortexed and sonicated for 5 min. The 1 mg/mL DMSO solution was diluted to 10 and 30 μg/mL acetonitrile stocks, by adding 10 μL to 990 μL acetonitrile and 30 μL to 970 acetonitrile, respectively. The 10 and 30 μg/mL acetonitrile stocks were then serially diluted 1:9 (v/v) (100 μL stock into 900 μL acetonitrile) to give the following solutions: 0.003, 0.01, 0.03, 0.1, 0.3, 1, 3, 10 and 30 μg/mL acetonitrile.

Preparation of Plasma Standards, Blanks and Samples

Control male Sprague Dawley rat plasma and the study plasma samples were stored at −80° C. until the day of analysis when they were thawed at room temperature. Control plasma was centrifuged (2,000 g for 10 min) and aliquoted (90 μL) into eppendorf tubes for preparation of standards and blank samples. Study samples were previously aliquoted (100 μL) into eppendorf tubes immediately following collection of the plasma.

An aliquot (10 μL) of the appropriate acetonitrile stock was added to the control plasma (to give a final volume of 100 μL) to give the required calibration standards covering the range 1-3000 ng/mL. Double blank and blank samples were prepared by adding 10 μL of acetonitrile to 90 μL of blank plasma.

Preparation of Brain Standards, Blanks and Samples

Control male Sprague Dawley rat brain and the study brain samples were weighed after collection and stored at −80° C. until the day of analysis when they were thawed at room temperature. Once thawed brains were diluted with water (4 mL per gram of tissue) and homogenised using a mechanical homogeniser. An aliquot (100 μL) of each study sample was taken into Micronics tubes ready for analysis and sufficient aliquots (90 μL) of control brain homogenate prepared for preparation of standards and blanks.

An aliquot (10 μL) of the appropriate acetonitrile stocks was added to the control brain homogenate (to give a final volume of 100 μL) to give the required calibration standards covering the range 1.5-5000 ng/g. Double blank and blank samples were prepared by adding 10 μL of acetonitrile to 90 μL of blank brain homogenate.

Extraction of Plasma and Brain Samples, Standards and Blanks

Each plasma and brain homogenate sample, standard and blank (100 μL) was extracted with an aliquot (300 μL) of acetonitrile (containing 0.1% formic acid and 100 ng/mL of an appropriate internal standard). Double blanks were extracted with an aliquot (300 μL) of acetonitrile containing 0.1% formic acid). All samples, standards and blanks were then vortex mixed and centrifuged (2000 g for 15 min). An aliquot (50 μL) of the resulting supernatant was then taken into a 2 mL 96-deep well plate and diluted with acetonitrile: water (50:50 v/v) (150 µL) ready for analysis by a specific LC-MS/MS method.

Preparation of CSF Samples, Standards and Blanks

Control male Sprague Dawley rat CSF and the study CSF samples were stored at −80° C. until the day of analysis when they were thawed at room temperature. An aliquot (50 µL) of each study sample was taken into Micronics tubes ready for analysis and sufficient aliquots (45 µL) of control CSF prepared for preparation of standards and blanks.

An aliquot (5 µL) of the appropriate acetonitrile stocks was added to the control CSF (to give a final volume of 50 µL) to give the required calibration standards covering the range 1-1000 ng/mL. Double blank and blank samples were prepared by adding 5 µL of acetonitrile to 45 µL of blank CSF.

Extraction of CSF Samples, Standards and Blanks

Each CSF sample, standard and blank (50 µL) was extracted with an aliquot (150 µL) of acetonitrile (containing 0.1% formic acid and 100 ng/mL of an appropriate internal standard). Double blanks were extracted with an aliquot (150 µL) of acetonitrile containing 0.1% formic acid. All samples were then vortex mixed and an aliquot (50 µL) of each was then further diluted in 150 µL of acetonitrile:water (50/50 v/v) in a 2 mL 96-deep well block ready for LC-MS/MS analysis.

All samples were then analysed using a Waters Acquity UPLC coupled to a Waters Xevo TQ mass spectrometer.

LC Conditions:

Column: Acquity UPLC BEH C18, 1.7 urn, 2.1×50 mm, maintained at 40° C.

Mobile Phase: A=95% Water: 5% MeOH containing 0.01M Ammonium acetate
B=5% Water: 95% MeOH containing 0.01M Ammonium acetate

| Time (min) | B (%) |
|---|---|
| 0 | 5 |
| 1.2 | 95 |
| 1.5 | 95 |
| 1.7 | 5 |
| 2.0 | 5 |

Gradient:

Flow rate: 0.6 mL/min; injection volume 5 µL; autosampler temperature 6° C.

LC flow was diverted to waste for the first 0.3 min of each injection

MS/MS transitions were optimised automatically by Waters QuanOptimise software.

Amyloid Detection

DEA/NaCl Extraction of AR Peptides from Rat Brain:

100 ml of chilled 0.2% diethyl amine (DEA) in 50 mM NaCl (pH 10) was freshly prepared and 1 ml/25 mg brain tissue was added to each hemisphere (i.e. 40× brain volume). The brains were immediately homogenized using a Polytron PT 1200 for 1.5 minutes and samples left to incubate on ice for one hour after homogenisation. 3 ml of the homogenate was transferred to a polyallomer tube (Beckman #362333) and spun at 133000×g (55,000 rpm) for 45 min at 4° C. The supernatant was then neutralised to pH 8-8.3 by adding 1/10 volume 0.5M Tris/HCl, pH 6.8. The samples can be used fresh or snap frozen on dry-ice and stored at −80° C. until required for analysis Human/Rat βAmyloid (40) ELISA (Wako Kit)

The Wako Aβ40 ELISA kit (Code No. 294-62501) uses the monoclonal antibody BNT77, raised against epitope Aβ(11-28) and the monoclonal antibody BA27, which specifically detects the C-terminal portion of Aβ40. This kit is used for the quantitative determination of human or rat Aβ(1-40) and also N-terminally truncated Aβ40 species (Aβ(x-40)) in biological matrices such as tissue culture medium, tissue homogenate, CSF and plasma.

For analysis, plasma and brain samples are diluted 1:1 with the standard diluent contained in the kit and CSF samples are diluted 1:8 with the standard diluent contained in the kit. The assay is carried out according to manufacturers instructions and samples are analysed in duplicate. Data is analysed using Microsoft Excel 2003 and statistical analysis is carried out using Genstat $9^{th}$ Edition.

Thus, when Comparative Example 1 was administered at a dose of 10 mg/kg p.o. and plasma, brain and CSF samples were collected 2, 4, 6 and 8 hours post-dose the following concentrations were measured (Table 1):

TABLE 1

Data for Comparative Example 1
(Example 73 in WO2009/091016)

| Time (h) | [Pl] (nM) | $^1$[Pl$_u$] (nM) | [Br] (nM) | $^2$[Br$_u$] (nM) | [CSF] (nM) | Br$_{tot}$: Pl$_{tot}$ | Br$_u$: Pl$_u$ | CSF: Pl$_u$ |
|---|---|---|---|---|---|---|---|---|
| 2 | 1257 | 440 | 971 | 65 | 104 | 0.8 | 0.15 | 0.24 |
| 4 | 1162 | 407 | 874 | 59 | 88 | 0.7 | 0.14 | 0.22 |
| 6 | 834 | 292 | 570 | 38 | 63 | 0.7 | 0.13 | 0.22 |
| 8 | 484 | 169 | 368 | 25 | 26 | 0.8 | 0.15 | 0.15 |

$^1$Calculated by multiplying the [Pl] by Pl Fu.
$^2$Calculated by multiplying the [Br] by Br Fu.

From the above study, Comparative Example 1 showed a 59% and 64% reduction of Aβ40 in the brain at 4 and 6 hours respectively; and a 76% and 70% reduction of Aβ40 in the CSF at 4 and 6 hours respectively.

Certain compounds of the present invention have been assessed in vivo in the rat to corroborate the levels of CNS penetration; these data are presented in the tables below.

Surprisingly, it has been found that examples of compounds of the present invention show increased CNS penetration in the rat relative to compounds from WO2009/091016 by any of the aforementioned recognized methods of determining CNS penetration. Thus the compounds of the present invention may show improved profiles in that they more readily target the site of action, the brain, and therefore may show improved efficacy or efficacy at lower concentrations or doses or decreased peripherally mediated side effects, by way of preferential CNS partitioning, or a combination of any or all of these aspects.

Thus, when Example 4 was administered at a dose of 10 mg/kg p.o. and plasma and brain samples were collected 2, 4, 6 and 8 hours post-dose the following concentrations were measured (Table 2).

TABLE 2

Data for Example 4

| Time (h) | [Pl] (nM) | $^1$[Pl$_u$] (nM) | [Br] (nM) | $^2$[Br$_u$] (nM) | [CSF] (nM) | Br$_{tot}$: Pl$_{tot}$ | Br$_u$: Pl$_u$ | CSF: Pl$_u$ |
|---|---|---|---|---|---|---|---|---|
| 2 | 392 | 51 | 1470 | 31 | 33 | 3.8 | 0.6 | 0.6 |
| 4 | 482 | 63 | 1616 | 34 | 40 | 3.4 | 0.5 | 0.6 |
| 6 | 162 | 21 | 609 | 13 | 13 | 3.8 | 0.6 | 0.6 |
| 8 | 105 | 14 | 385 | 8 | 8 | 3.7 | 0.6 | 0.6 |

$^1$Calculated by multiplying the [Pl] by Pl Fu.
$^2$Calculated by multiplying the [Br] by Br Fu.

From the above study, Example 4 showed a 51% and 42% reduction of Aβ40 in the brain at 4 and 6 hours respectively, and a 67% and 63% reduction of Aβ40 in the CSF at 4 and 6 hours respectively.

Thus compounds of the present invention show increased CNS penetration and whilst demonstrating efficacy in the CNS. The efficacy is thus achieved with lower circulating plasma concentrations.

When Example 3 was administered at a dose of 10 mg/kg p.o. and plasma, brain and CSF samples were collected 2, 4, 6 and 8 hours post-dose the following concentrations were measured (Table 3).

TABLE 3

Data for Example 3

| Time (h) | [Pl] (nM) | $^1$[Pl$_u$] (nM) | [Br] (nM) | $^2$[Br$_u$] (nM) | [CSF] (nM) | Br$_{tot}$: Pl$_{tot}$ | Br$_u$: Pl$_u$ | CSF: Pl$_u$ |
|---|---|---|---|---|---|---|---|---|
| 2 | 385 | 55 | 1087 | 38 | 34 | 2.8 | 0.7 | 0.6 |
| 4 | 226 | 32 | 576 | 20 | 16 | 2.5 | 0.6 | 0.5 |
| 6 | 232 | 33 | 561 | 20 | 15 | 2.4 | 0.6 | 0.5 |
| 8 | 85 | 12 | 257 | 9 | 9 | 3.0 | 0.7 | 0.7 |

$^1$Calculated by multiplying the [Pl] by Pl Fu.
$^2$Calculated by multiplying the [Br] by Br Fu.

From the above study, Example 3 showed a 58% and 61% reduction of Aβ40 in the brain at 4 and 6 hours respectively, and a 75% and 71% reduction of Aβ40 in the CSF at 4 and 6 hours respectively. Thus compounds of the present invention show increased CNS penetration and whilst demonstrating efficacy in the CNS. The efficacy is thus achieved with lower circulating plasma concentrations.

When Example 2 was administered at a dose of 10 mg/kg p.o. and plasma, brain and CSF samples were collected 2, 4, 6 and 8 hours post-dose the following concentrations were measured (Table 4).

TABLE 4

Data for Example 2

| Time (h) | [Pl] (nM) | $^1$[Pl$_u$] (nM) | [Br] (nM) | $^2$[Br$_u$] (nM) | [CSF] (nM) | Br$_{tot}$: Pl$_{tot}$ | Br$_u$: Pl$_u$ | CSF: Pl$_u$ |
|---|---|---|---|---|---|---|---|---|
| 2 | 850 | 214 | 1781 | 118 | 133 | 2.1 | 0.6 | 0.6 |
| 4 | 645 | 163 | 1338 | 88 | 201 | 2.1 | 0.5 | 1.2 |
| 6 | 353 | 89 | 703 | 46 | 60 | 2.0 | 0.5 | 0.7 |
| 8 | 224 | 56 | 479 | 32 | 68 | 2.1 | 0.6 | 1.2 |

$^1$Calculated by multiplying the [Pl] by Pl Fu.
$^2$Calculated by multiplying the [Br] by Br Fu.

From the above study, Example 2 showed a 63% and 65% reduction of Aβ40 in the brain at 4 and 6 hours respectively, and an 85% and 69% reduction of Aβ40 in the CSF at 4 and 6 hours respectively. Thus compounds of the present invention show increased CNS penetration and whilst demonstrating efficacy in the CNS. The efficacy is thus achieved with lower circulating plasma concentrations.

Method for Determination of Plasma Protein Binding (PPB) and Brain Tissue Binding (BTB)

Compound Preparation

Compounds were dissolved in DMSO to give a 1 mg free base/mL solution, before further dilution to 100 µg/mL in acetonitrile (100 µL of 1 mg/mL into 900 µL acetonitrile).

Matrix Preparation

On the morning of dialysis, control male Sprague Dawley rat plasma and brain, previously stored at −80° C. were thawed at room temperature. Plasma was checked for pH and if necessary adjusted to 7.4 with 1M HCl. Plasma was then centrifuged (2000 g for 10 min) and the brains diluted with 2 mL of Phosphate Buffered Saline (pH 7.4) per gram of tissue and homogenised using a mechanical homogeniser. An aliquot (10 µL) of the 100 µg/mL acetonitrile compound solution was then added to 1 mL of plasma and brain homogenate and vortex mixed to give a final compound concentration of 1 µg/mL in matrix.

RED Plate Preparation

The Rapid Equilibrium Dialysis (RED) plate (Thermo Scientific) was prepared in accordance with the manufacturers guidelines i.e. the base plate was soaked in 20% (v/v) ethanol for 10 min and then rinsed twice with deionised water before being allowed to dry. The base plate was then filled with the appropriate number of disposable inserts (n=3 per compound) (Thermo Scientific) and matrix containing 1 µg/mL compound added into the matrix chamber of the inserts (200 µL) and an aliquot (350 µL) of PBS added to the buffer chamber. The plate was then covered with an adhesive and incubated in air at 37° C. for 6 h with 130 rpm agitation.

Sampling

Following the 6 h incubation, the seal was removed and an aliquot (50 µL) taken from the PBS chambers and dispensed into Micronics tubes. Also, an aliquot (50 µL) was removed from the matrix chambers and placed into separate Micronics tubes. Plasma and brain was then matrix matched with 50 µL of drug-free PBS and the PBS samples with 50 µL of the corresponding drug-free matrix, to give equal final compositions and volumes (1004).

Sample Analysis

Samples were vortex mixed and an aliquot (300 µL) of acetonitrile containing 0.1% formic acid and 100 ng/mL of an appropriate internal standard added. Samples were then mixed and centrifuged (2000 g for 15 min) and an aliquot of the supernatant (100 µL) removed into a 96-deep well plate and diluted with an equal volume of water ready for analysis by LC-MS/MS.

The following data was obtained for the following compounds in the above assay (Table 5).

TABLE 5

| Compound | Rat PPB (%) | Rat Plasma fu | Rat BTB (%) | Rat Brain fu |
|---|---|---|---|---|
| Comparative Example 1 | 65.0 | 0.350 | 93.3 | 0.067 |
| Example 4 | 87.0 | 0.130 | 97.9 | 0.021 |
| Example 3 | 85.7 | 0.143 | 96.5 | 0.035 |
| Example 2 | 74.9 | 0.252 | 93.4 | 0.066 |

Data represents the Mean of n = 3 replicates
fu = fraction unbound

From the data presented herein above it will be apparent to those skilled in the art that the compounds of the invention achieve a similar reduction of brain Aβ40 to that of Comparative Example 1, but with a lower plasma concentration and free plasma concentration. This is advantageous and indicates that the compounds of the invention will have similar or better efficacy at lower concentrations than the compounds of WO2009/091016, and consequently will be less likely to cause unwanted peripherally mediated side effects, such as cardiovascular effects, phospholipidosis, liver toxicity, renal toxicity and gastrointestinal toxicity.

In addition to improved CNS penetration, the compounds of the present invention also demonstrated improved metabolic stability compared to compounds described in WO2009/091016 as outlined in the table below (Table 6):

TABLE 6

| Compound | HLM stability[1] |
| --- | --- |
| Comparative Example 2 (Example 107 from WO2009/092016) | 0.3 |
| Comparative Example 3 (Example 177 from WO2009/092016) | 1.5 |
| Example 2 | 82.0 |
| Example 3 | 73.3 |
| Example 4 | 78.6 |

[1]percentage of parent remaining upon 30 minute incubation with human liver microsomes (HLM) in the assay described below.

Human Liver Microsomal Stability Assay

The compound was dissolved in DMSO to prepare 1 mmol/L DMSO solution. The DMSO solution was diluted with distilled water to prepare 1 μmol/L compound dosing solution (DMSO conc.: 0.1%).

105 μL of reaction buffer (1 mol/L phosphate buffer (pH 7.4)/1 mmol/L EDTA (pH 7.4)/distilled water=1/1/5, v/v/v), 15 μL of 1 μmol/L compound dosing solution, and 15 μL of rat or human liver microsomes (5 mg/mL) were mixed, and preincubated for 5 min at 37° C. Metabolic reaction was initiated by adding 15 μL of NADPH generating system (3.3 mmol/L β-NADPH+, 80 mmol/L glucose 6-phosphate, 1 unit/mL glucose 6-phosphate dehydrogenase, 60 mmol/L $MgCl_2$). For the control sample, NADPH generating system was replaced with 60 mmol/L $MgCl_2$. The 150 μL of reaction mixture (final compound conc.: 0.1 μmol/L, final DMSO conc.: 0.01%) was incubated for 30 min at 37° C., and the reaction was terminated by adding 150 μL of methanol/acetonitrile solution containing an appropriate internal standard compound. The sample was vortexed and centrifuged, and obtained supernatant was subject to LC/MS analysis.

Next, methods for preparing the compound of formula (I) or pharmaceutically acceptable salt thereof according to the present invention will be described.

A. General Preparation Method A:

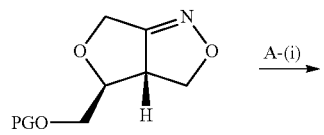

A-(1)

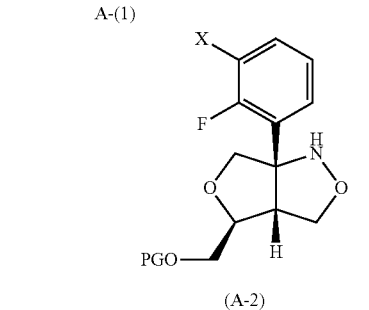

(A-2)

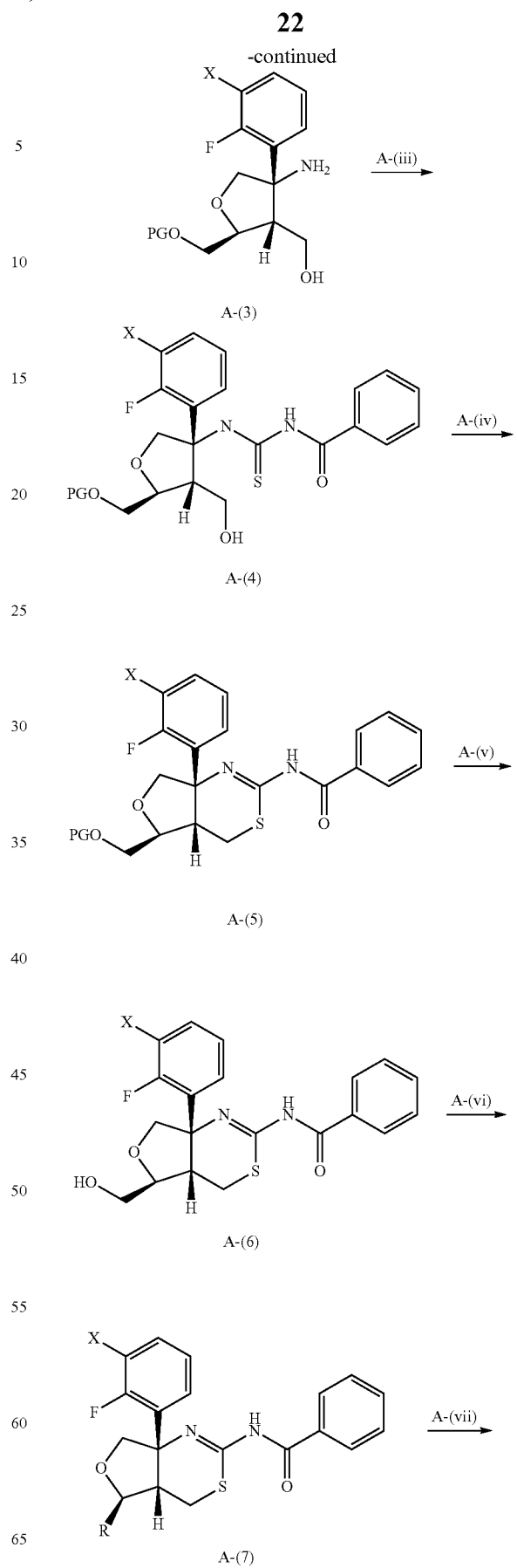

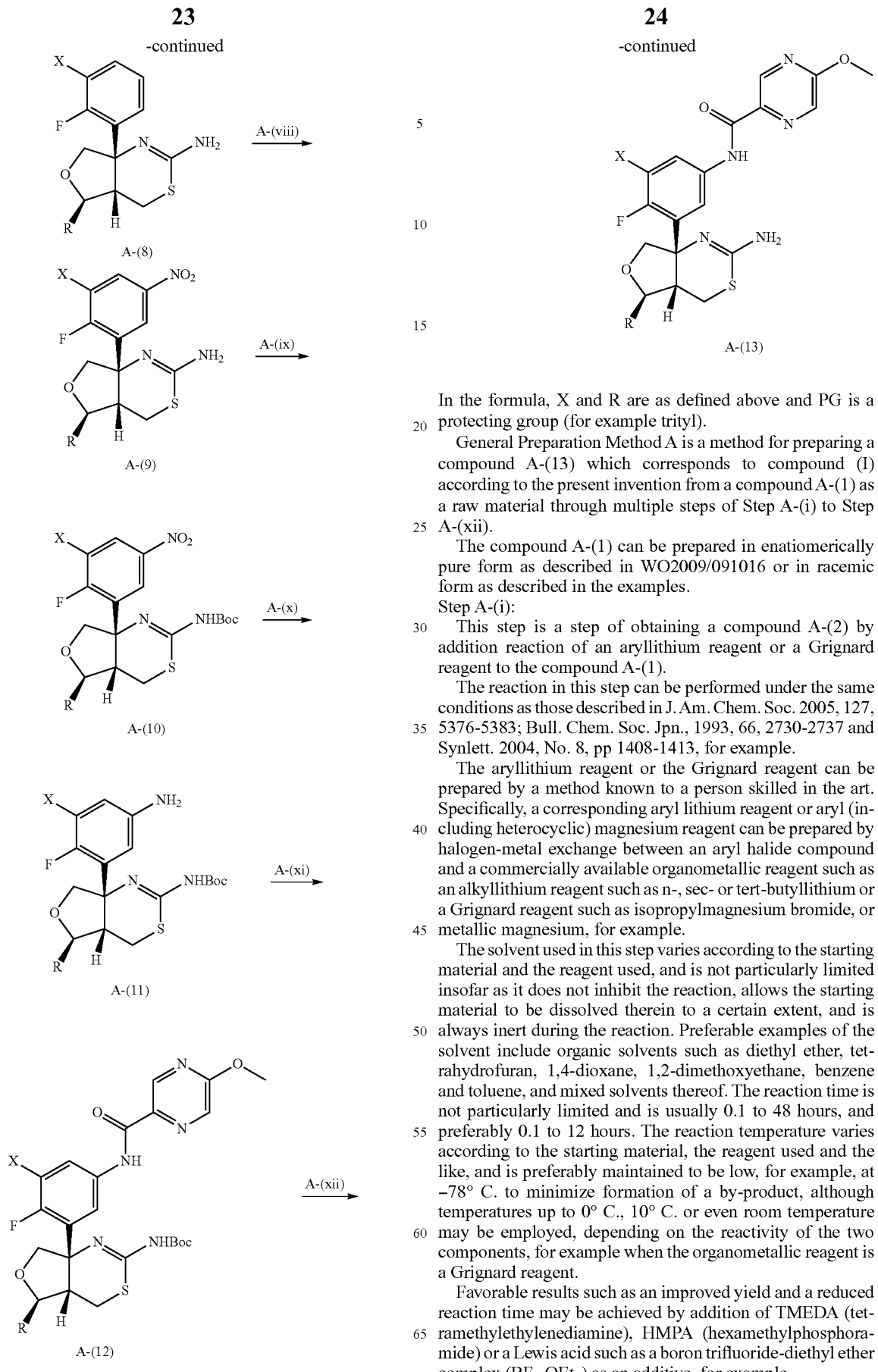

In the formula, X and R are as defined above and PG is a protecting group (for example trityl).

General Preparation Method A is a method for preparing a compound A-(13) which corresponds to compound (I) according to the present invention from a compound A-(1) as a raw material through multiple steps of Step A-(i) to Step A-(xii).

The compound A-(1) can be prepared in enatiomerically pure form as described in WO2009/091016 or in racemic form as described in the examples.

Step A-(i):

This step is a step of obtaining a compound A-(2) by addition reaction of an aryllithium reagent or a Grignard reagent to the compound A-(1).

The reaction in this step can be performed under the same conditions as those described in J. Am. Chem. Soc. 2005, 127, 5376-5383; Bull. Chem. Soc. Jpn., 1993, 66, 2730-2737 and Synlett. 2004, No. 8, pp 1408-1413, for example.

The aryllithium reagent or the Grignard reagent can be prepared by a method known to a person skilled in the art. Specifically, a corresponding aryl lithium reagent or aryl (including heterocyclic) magnesium reagent can be prepared by halogen-metal exchange between an aryl halide compound and a commercially available organometallic reagent such as an alkyllithium reagent such as n-, sec- or tert-butyllithium or a Grignard reagent such as isopropylmagnesium bromide, or metallic magnesium, for example.

The solvent used in this step varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene and toluene, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78° C. to minimize formation of a by-product, although temperatures up to 0° C., 10° C. or even room temperature may be employed, depending on the reactivity of the two components, for example when the organometallic reagent is a Grignard reagent.

Favorable results such as an improved yield and a reduced reaction time may be achieved by addition of TMEDA (tetramethylethylenediamine), HMPA (hexamethylphosphoramide) or a Lewis acid such as a boron trifluoride-diethyl ether complex ($BF_3 \cdot OEt_2$) as an additive, for example.

Step A-(ii):

This step is a step of obtaining a compound A-(3) by subjecting the compound A-(2) to reductive cleavage reaction of the N—O bond.

The reductive cleavage reaction of the N—O bond can be performed under the conditions using zinc-acetic acid, a metal catalyst such as hydrogen-platinum oxide, or lithium aluminum hydride, for example.

The reaction using zinc such as zinc-acetic acid can be performed under the same conditions as those described in J. Org. Chem. 2003, 68, 1207-1215 and Org. Lett. 2005, 7, 5741-5742, for example. Examples of the acid used include acetic acid, formic acid and hydrochloric acid. The solvent used in the reaction is not particularly limited insofar as it does not inhibit the reaction and allows the starting material to be dissolved therein to a certain extent. Examples of the solvent include methanol, ethanol, 1,4-dioxane, THF and water. The above acid may also be used as a solvent. The reaction temperature is usually −20° C. to solvent reflux temperature, and preferably ice-cold temperature to solvent reflux temperature. The reaction time is not particularly limited and is usually 5 minutes to 48 hours, and preferably 5 minutes to 24 hours.

The reaction using a metal catalyst such as hydrogen-platinum oxide can be performed under the same conditions as those described in Tetrahedron: Asymmetry, 1994, 5, 1018-1028 and Tetrahedron, 1997, 53, 5752-5746, for example. The compound A-(3) can be obtained by hydrogenating the compound A-(2) using platinum oxide as a catalyst in a solvent such as methanol, for example.

The reaction using lithium aluminum hydride can be performed under the same conditions as those described in Bull. Chem. Soc. Jpn., 1993, 66, 2730-2737 for example. The compound A-(3) can be obtained by reducing the compound A-(2) using lithium aluminum hydride in a solvent such as ether, for example.

Step A-(iii):

This step is a step of obtaining a compound A-(4) from the compound A-(3). The thiourea derivative A-(4) can be obtained from the compound A-(3) by a method known to a person skilled in the art.

The compound A-(4) can be obtained in this step by reacting the compound A-(3) with benzoyl isothiocyanate in a solvent such as dichloromethane or toluene or ethyl acetate. This reaction can be performed under the same conditions as those described in J. Med. Chem. 1990, 33, 2393-2407, for example. The solvent used in the reaction is not particularly limited insofar as it does not inhibit the reaction and allows the starting material to be dissolved therein to a certain extent. Examples of the solvent include dichloromethane, chloroform, toluene, 1,4-dioxane, THF and ethyl acetate. The reaction temperature is usually −20° C. to solvent reflux temperature, and preferably ice-cold temperature to room temperature. The reaction time is not particularly limited and is usually 5 minutes to 48 hours, and preferably 5 minutes to 24 hours.

Step A-(iv):

This step is a method of obtaining a compound A-(5) by cyclizing the compound A-(4).

In this reaction, the compound A-(4) can be cyclized under various conditions to obtain the compound A-(5) by activating the alcohol of compound A-(4).

For example, the compound A-(5) can be obtained in this reaction by heating the compound A-(4) in a solvent such as methanol in the presence of an acid such as concentrated hydrochloric acid, for example. The solvent used in the reaction is not particularly limited insofar as it does not inhibit the reaction and allows the starting material to be dissolved therein to a certain extent. Examples of the solvent include solvents such as methanol, ethanol, 1-propanol and water, mixed solvents thereof, and acids used as a solvent. The reaction can be performed by using one equivalent to a large excess of an appropriate acid to act in the presence or absence of such a solvent. Examples of the acid used include concentrated hydrochloric acid, hydrobromic acid, sulfuric acid, trifluoroacetic acid, methanesulfonic acid, trifluoromethanesulfonic acid and mixtures thereof. The reaction time is not particularly limited and is usually 0.5 to 72 hours, and preferably 0.5 to 24 hours. The reaction temperature is usually ice-cold temperature to solvent reflux temperature.

Alternatively, the compound A-(5) can be obtained by reacting the compound A-(4) with trifluoromethanesulfonic anhydride in a solvent such as dichloromethane in the presence of a base such as pyridine. The solvent used in the reaction is not particularly limited insofar as it does not inhibit the reaction and allows the starting material to be dissolved therein to a certain extent. Those skilled in the art will appreciate that a solvent is not always required and the the reaction may also be conducted in the absence of a solvent, for example when the base is pyridine. Examples of the solvent include solvents such as dichloromethane, chloroform, 1,2-dichloroethane, THF, 1,2-dimethoxyethane and toluene, and mixed solvents thereof. The reaction can be performed using 1 to 20 equivalents of an appropriate base in such a solvent. Examples of the base used include pyridine, 2,6-lutidine, sodium carbonate, potassium carbonate and mixtures thereof. The reaction time is not particularly limited and is usually 0.5 to 24 hours, and preferably 0.5 to 12 hours. The reaction temperature is usually −78° C. to room temperature.

Step A-(v):

This step is a method of obtaining a compound A-(6) by deprotecting the alcohol protecting group of the compound A-(5).

Those skilled in the art will appreciate that various suitable alcohol protecting groups could be selected and that the choice of protecting group is influenced by its chemical stability and conditions required for deprotection. Suitable protecting groups are described in T. W. Greene and P. G. M. Wuts, "Protective Groups in Organic Chemistry, Third Edition", John Wiley & Sons (1999).

When the protecting group is trityl (triphenylmethyl), suitable conditions for the deprotection can be found in T. W. Greene and P. G. M. Wuts, "Protective Groups in Organic Chemistry, Third Edition", John Wiley & Sons (1999), P. 102-104.

For example, a compound A-(6) can be prepared from A-(5) by removing the trityl protecting group from compounds A-(5) by treating with acid. Depending on the choice of acid it may act as a solvent, or alternatively a solvent may also be added. The solvent used in the reaction is not particularly limited insofar as it does not inhibit the reaction and allows the starting material to be dissolved therein to a certain extent. Examples of the solvent include alcoholic solvents such as methanol and ethanol which may or may not be used in conjunction with water. An example of a suitable solvent system is aqueous methanol. Those skilled in the art will appreciate that the compound A-(5) may or may not dissolve in the solvent or may partially dissolve. The acid used is not particularly limited. Examples of acids include strong mineral acids for example concentrated hydrochloric acid. The reaction time is not particularly limited and is usually 0.5 to 72 hours, and preferably 0.5 to 24 hours. The reaction temperature is usually ice-cold temperature to solvent reflux temperature, and preferably room temperature.

Alternatively, the reaction may be conducted with an acid in the absence of a solvent. Examples of such acids include formic acid. The reaction time is not particularly limited and is usually 0.1 to 72 hours, and preferably 0.1 to 24 hours. The reaction temperature is usually ice-cold temperature to solvent reflux temperature, and preferably room temperature. Those skilled in the art will appreciate that these conditions may also result in the concomitant formation of a formate ester in addition to the desired alcohol. Those skilled in the art will know how to monitor the reaction and the formation of the aforementioned formate ester. Those skilled in the art will also appreciate how to convert the formate ester to the desired alcohol. For example the formate ester could be converted to the alcohol by hydrolyzing the ester, for example by using an alcohol, for example, methanol or ethanol, in the presence of a base, for example triethylamine. The reaction time is not particularly limited and is usually 0.1 to 72 hours, and preferably 0.1 to 24 hours. The reaction temperature is usually ice-cold temperature to solvent reflux temperature.

Step A-(vi):

This step is a method of obtaining a compound A-(7) from the compound A-(6) by converting the primary alcohol in compound A-(6) to $CH_2F$, as outlined in step A-(vi)-a, or $CHF_2$, as outlined in step A-(vi)-b and c, wherein R is as defined in compound-(I).

Step A-(vi)-a

This step is the step of obtaining a compound A-(7) from the compound A-(6) wherein R=$CH_2F$ by converting the primary alcohol in compound A-(6) to $CH_2F$ by activation of the alcohol and displacement with a fluoride equivalent.

Those skilled in the art will appreciate that activation of the alcohol and displacement by a fluoride equivalent may be conducted with a single reagent. Examples of such reagents are diethylaminosulfur trifluoride (DAST, J. Org. Chem. 1975, 40, 574), bis-(2-methoxyethyl)aminosulfur trifluoride (deoxo-fluor, Synthesis, 2002, 17, 2561; J. Org. Chem. 1999, 64, 7048; Chem. Commun. 1999, 215), diethylaminodifluorosulfinium tetrafluoroborate (XtalFluor-E, J. Org. Chem. 2010, 75, 3401), morpholinodifluorosulfinium tetrafluoroborate (XtalFluor-M, J. Org. Chem. 2010, 75, 3401) and perfluoro-1-butanesulfonyl fluoride (PBSF, Tetrahedron Lett. 1995, 36, 2611). Those skilled in the art will appreciate that in some instances it may be necessary or advantageous to add an additional reagent to provide a further source of fluoride, examples of such reagents include, but are not limited to, triethylamine trihydrofluoride (TEA.3HF), triethylamine dihydrofluoride (TEA.2HF) and hydrogen fluoride. The solvent used in the reaction is not particularly limited insofar as it does not inhibit the reaction and allows the starting material to be dissolved therein to a certain extent. Examples of the solvent include solvents such as dichloromethane, chloroform, 1,2-dichloroethane, THF, and mixed solvents thereof. The reaction time is not particularly limited and is usually 0.5 to 24 hours, and preferably 0.5 to 12 hours. The reaction temperature is usually 0° C. to room temperature.

Step A-(vi)-b and c

These steps are the steps of obtaining a compound A-(7) from the compound A-(6) wherein R=$CHF_2$ by converting the primary alcohol in compound A-(6) to $CHF_2$ by oxidation of the alcohol to the aldehyde (step b) and conversion of the aldehyde to a difluoromethyl moiety (step c) by reaction with a fluorinating reagent.

Step A-(vi)-b

This step is the step of converting the alcohol A-(6) to an aldehyde by subjecting compound A-(6) to an oxidation reaction. Oxidation conditions to convert a primary alcohol to an aldehyde are known to those skilled in the art. Examples of such conditions and reagents include reaction with Dess-Martin periodinane (J. Org. Chem. 1983, 48, 4155; Org. Synth. Coll. Vol. 10, 696) in a suitable solvent, for example DCM, at an appropriate reaction temperature, for example 0° C. to room temperature. Those skilled in the art will also appreciate that it may be possible to conduct this reaction with a range of alternative conditions, for example using TPAP (Synthesis 1994, 639), Swern oxidation (Synthesis 1981, 165-185; Org. React. 39: 297-572; Synthesis 1990: 857-870), Parikh-Doering oxidation (J. Am. Chem. Soc., 1967, 89: 5505-5507), Corey-Kim oxidation (J. Am. Chem. Soc 1972, 94, 7586), Pfitzner-Moffatt (J. Am. Chem. Soc. 1963, 85, 3027) or using pyridinium chlorochromate (PCC) (Tetrahedron 1990, 46: 4417-4420; Tetrahedron Lett., 1975, 16, 2647-2650).

Those skilled in the art will also appreciate that precautions may be required in handling certain aldehydes.

Step A-(vi)-c

This step is the step of converting an aldehyde to a difluoromethyl group. Those skilled in the art will appreciate that conversion of the aldehyde to a difluoromethyl group may be conducted with a fluorinating reagent. Examples of such reagents are diethylaminosulfur trifluoride (DAST, J. Org. Chem. 1975, 40, 574), bis-(2-methoxyethyl)aminosulfur trifluoride (deoxo-fluor, Synthesis, 2002, 17, 2561; J. Org. Chem. 1999, 64, 7048; Chem. Commun. 1999, 215), diethylaminodifluorosulfinium tetrafluoroborate (XtalFluor-E, J. Org. Chem. 2010, 75, 3401) and morpholinodifluorosulfinium tetrafluoroborate (XtalFluor-M, J. Org. Chem. 2010, 75, 3401). Those skilled in the art will appreciate that in some instances it may be necessary or advantageous to add an additional reagent to provide a further source of fluoride, examples of such reagents include, but are not limited to, triethylamine trihydrofluoride (TEA.3HF), triethylamine dihydrofluoride (TEA.2HF) and hydrogen fluoride. The solvent used in the reaction is not particularly limited insofar as it does not inhibit the reaction and allows the starting material to be dissolved therein to a certain extent. Examples of the solvent include solvents such as dichloromethane (DCM), dichloroethane (DCE), chloroform, 1,2-dichloroethane, THF, and mixed solvents thereof. The reaction time is not particularly limited and is usually 0.5 to 24 hours, and preferably 0.5 to 12 hours. The reaction temperature is usually 0° C. to solvent reflux, preferably 0° C. to room temperature.

Step A-(vii)

This step is a method of obtaining the compound A-(8) by deprotecting the protecting group of the compound A-(7). The compound A-(8) can be obtained under deprotection conditions known to a person skilled in the art for removing benzoyl groups. For example, the compound A-(8) can be obtained in this reaction by heating the compound A-(7) in a solvent such as methanol in the presence of a base such as DBU, for example. This reaction can be performed under the same conditions as those described in Synth. Commun. 2002, 32 (2), 265-272 for example. The solvent used in the reaction is not particularly limited insofar as it does not inhibit the reaction and allows the starting material to be dissolved therein to a certain extent. Examples of the solvent include solvents such as methanol, ethanol and 1-propanol. The reaction can be performed using 1 to 20 equivalents of an appropriate base in such a solvent. Examples of the base used include DBU. The reaction time is not particularly limited and is usually 0.5 to 24 hours, and preferably 0.5 to 12 hours. The reaction temperature is usually room temperature to solvent reflux temperature.

Alternatively, the compound A-(8) can be obtained in this reaction by heating compound A-(7) with an inorganic base such as potassium carbonate, for example. The solvent used in the reaction is not particularly limited insofar as it does not inhibit the reaction and allows the starting material to be dissolved therein to a certain extent. Examples of the solvent include solvents such as methanol, ethanol and 1-propanol. The reaction can be performed using 1 to 20 equivalents of an appropriate base in such a solvent, and preferably a slight excess is used. Examples of the base used include potassium carbonate. The reaction time is not particularly limited and is usually 0.5 to 24 hours, and preferably 0.5 to 12 hours. The reaction temperature is usually room temperature to solvent reflux temperature, and preferably 50-100° C. Those skilled in the art will appreciate that the the selected solvent will limit the reaction temperature by its reflux temperature. Examples of suitable solvents include refluxing methanol.

Step A-(viii):

This step is a step of obtaining the compound A-(9) by nitration reaction of the compound A-(8). In this nitration reaction, the compound A-(9) can be obtained from the compound A-(8) by a method known to a person skilled in the art. Examples of the nitrating agent used in the reaction include potassium nitrate/concentrated sulfuric acid, fuming nitric acid/concentrated sulfuric acid and fuming nitric acid/acetic anhydride. Suitable solvents for the reaction include trifluoroacetic acid. The reaction temperature is not particularly limited and is usually −20° C. to room temperature, and preferable reaction temperatures include 0-10° C.

Step A-(ix):

This step is a step of obtaining a compound A-(10) by t-butoxycarbonylation of the amino group of the compound A-(9).

The reaction can be performed under the same conditions as those generally used in t-butoxycarbonylation of an amino compound such as the conditions described in a document such as T. W. Greene and P. G. M. Wuts, "Protective Groups in Organic Chemistry, Third Edition", John Wiley & Sons (1999), P. 518-525. The compound A-(10) can be obtained by reacting the compound A-(9) with di-tert-butyl dicarbonate using in a solvent such as tetrahydrofuran, for example. Alternative solvents include acetonitrile and DMF. Those skilled in the art will appreciate that a base may also be added to the reaction mixture, although is not essential. Suitable examples of a base include, but are not limited to triethylamine and diisopropylethylamine. The reaction temperature is not particularly limited and is usually to room temperature to reflux, and preferably room temperature to 60° C.

Step A-(x):

This step is a step of obtaining a compound A-(11) from the compound A-(10).

The compound A-(11) is synthesized by reducing the nitro compound A-(10) by a synthesis method known to a person skilled in the art. Examples of the method include reduction by catalytic hydrogenation using a noble metal catalyst such as Raney nickel, palladium, ruthenium, rhodium or platinum. Other reducing reagents include tin chloride, for example. Examples of the solvent include alcoholic solvents such as methanol, ethanol and 1-propanol, preferably ethanol. The reaction time is not particularly limited and is usually 0.5 to 24 hours, and preferably 0.5 to 18 hours. The reaction temperature is usually room temperature. Alternative reduction reaction conditions include reaction with iron with an additive such as ammonium chloride or hydrochloric acid, in an alcoholic solvent such as ethanol, at an appropriate reaction temperature, for example 65° C.

Step A-(xi):

This is a step of obtaining a compound A-(12) from the compound A-(11) by condensing compound A-(11) with a carboxylic acid and a condensing agent. The condensation reaction can be performed under the same conditions as those usually used and described in the following documents. Examples of the known method include those in J. Med. Chem., 1991, 34 (1), 227-234; Heterocycles, 1991, 32 (10), 1968-1972 and J. Med. Chem., 1994, 37 (7), 998-1014.

The compound A-(11) may be a free form or a salt.

The solvent in this reaction is not particularly limited insofar as it does not inhibit the reaction. Examples of the solvent include tetrahydrofuran, 1,4-dioxane, ethyl acetate, methyl acetate, dichloromethane, chloroform, N,N-dimethylformamide, toluene, acetonitrile and xylene. Examples of the condensing agent include CDI (N,N'-carbonyldiimidazole), Bop (1H-1,2,3-benzotriazol-1-yloxy(tri(dimethylamino))phosphonium hexafluorophosphate), DCC (N,N-dicyclohexylcarbodiimide), diethylphosphoryl cyanide, PyBOP (benzotriazol-1-yloxytri(pyrrolidino)phosphonium hexafluorophosphate) and WSC/EDC.HCl (1-ethyl-3-(3-dimethylaminopropyl)carbodiimide hydrochloride). Suitable conditions include an agent to activate the acid, such as N,N'-carbonyl diimidazole. One equivalent to a large excess of the acid may be used with respect to the compound A-(11). One equivalent to a large excess of an organic base such as triethylamine or N,N-diisopropylethylamine may be added where necessary.

The reaction time is not particularly limited and is usually 0.5 to 72 hours, and preferably 0.5 to 24 hours. The reaction temperature varies according to the raw material used, the solvent and the like and is not particularly limited. Ice-cold temperature to solvent reflux temperature is acceptable, ice cold to room temperature is preferable.

Alternatively, the compound A-(12) can be obtained by converting the desired carboxylic acid to the corresponding acid chloride and then reacting the acid chloride with the compound A-(11). The acid chloride can be synthesized by a means known to a person skilled in the art. For example the desired carboxylic acid may converted to the corresponding acid chloride by reaction with thionyl chloride in the presence or absence of a solvent, for example dichloromethane, N,N'-dimethylimidazoline-2-one, NMP or DMF. One to two equivalents or a large excess of thionyl chloride may be used with respect to the desired carboxylic acid. The reaction temperature is −30° C. to reflux, and preferably −10° C. to room temperature. An additive, such as carbonyl diimidazole may also be used. The acid chloride may also be formed by treating the acid with oxalyl chloride in a solvent such as dichloromethane in the presence of DMF. The reaction temperature is −30° C. to room temperature, and preferably −10° C. to room temperature Alternatively, the compound A-(12) can be obtained by converting the desired carboxylic acid to a mixed acid anhydride and then reacting the mixed acid anhydride with the compound A-(11). The mixed acid anhydride can be synthesized by a means known to a person skilled in the art. The synthesis is performed by reacting the desired carboxylic acid with a chloroformate such as ethyl chloroformate or isopropyl chloroformate in the presence of a base such as triethylamine, for example. One to two equivalents of the chloroformate and the base are used with respect to the desired carboxylic acid. The reaction temperature is −30° C. to room temperature, and preferably −20° C. to room temperature.

The step of condensing the mixed acid anhydride with the compound A-(11) is performed by reacting the mixed acid anhydride with the compound A-(11) in a solvent such as dichloromethane, tetrahydrofuran or N,N-dimethylformamide, for example. One equivalent to a large excess of the desired carboxylic acid is used with respect to the compound A-(11).

The reaction time is not particularly limited and is usually 0.5 to 48 hours, and preferably 0.5 to 12 hours. The reaction temperature is −20° C. to 50° C., and preferably −20° C. to room temperature.

Alternatively, the compound A-(12) can be obtained by converting the desired carboxylic acid to an active ester and then reacting the active ester with the compound A-(11). The step of obtaining the active ester is performed by reacting the desired carboxylic acid with an active ester synthesis reagent in a solvent such as 1,4-dioxane, tetrahydrofuran or N,N-dimethylformamide in the presence of a condensing agent such as DCC, for example. Examples of the active ester synthesis reagent include N-hydroxysuccinimide. One to 1.5 equivalents of the active ester synthesis reagent and the condensing agent are used with respect to the compound A-(11). The reaction time is not particularly limited and is usually 0.5 to 48 hours, and preferably 0.5 to 24 hours.

The reaction temperature is −20° C. to 50° C., and preferably −20° C. to room temperature.

The step of condensing the active ester with the compound A-(11) is performed by reacting the active ester with the compound A-(11) in a solvent such as dichloromethane, tetrahydrofuran or N,N-dimethylformamide, for example. One equivalent to a large excess of the active ester is used with respect to the compound A-(11). The reaction time is not particularly limited and is usually 0.5 to 48 hours, and preferably 0.5 to 24 hours. The reaction temperature is −20° C. to 50° C., and preferably −20° C. to room temperature.

Step A-(xii):

This step is a step of obtaining the compound A-(13) by deprotection of the t-butoxycarbonyl group of the compound A-(12).

The reaction can be performed under the same conditions as those generally used in deprotection reaction of a t-butoxycarbonyl group such as the conditions described in a document such as T. W. Greene and P. G. M. Wuts, "Protective Groups in Organic Chemistry, Third Edition", John Wiley & Sons (1999), P. 518-525. The compound A-(13) can be obtained by reacting the compound A-(12) with a strong acid, for example trifluoroacetic acid in the presence or absence of a solvent. Suitable solvents include dichloromethane. Alternative acids include hydrochloric acid in suitable solvents, such as methanol, diethyl ether or dioxane, for example.

The reaction temperature is normally ice cold to 80° C., preferably room temperature. The reaction time is not particularly limited and is usually 5 minutes to 48 hours, and preferably 5 minutes to 12 hours.

B. General Preparation Method B:

In the formula, X and R are as defined above.

General Preparation Method B is an alternative method for preparing a compound A-(13) which is a derivative of the compound (I) according to the present invention from a compound A-(9) as a raw material through multiple steps of Step B-(i) to Step B-(ii).

The compound A-(9) may be prepared as described in General Preparation Method A or the examples.

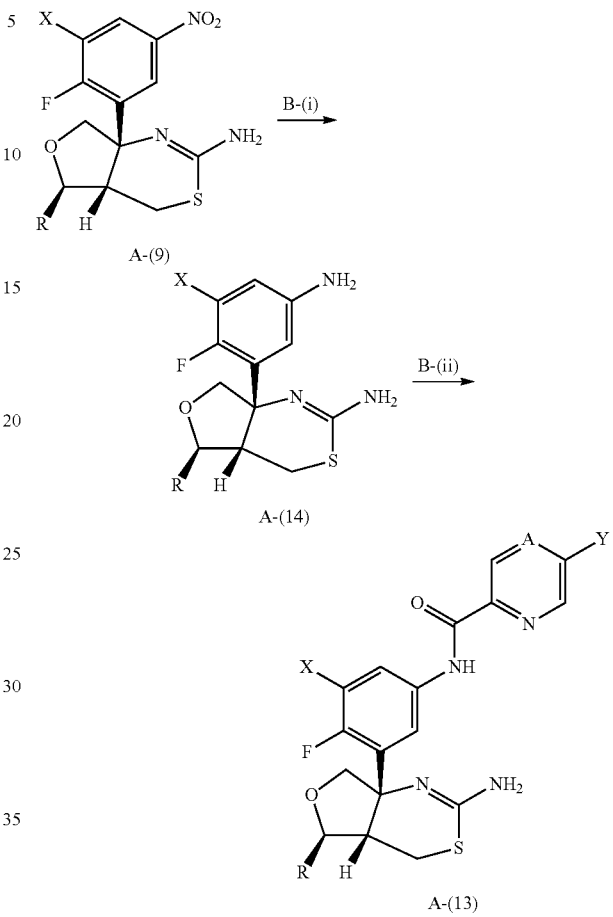

Step B-(i):

This step is a step of obtaining a compound A-(14) from the compound A-(9).

The compound A-(14) is synthesized by reducing the nitro compound A-(9) by a synthesis method known to a person skilled in the art. Reduction reaction conditions include reaction with iron with an additive such as ammonium chloride or hydrochloric acid, in an alcoholic solvent such as ethanol, at an appropriate reaction temperature, for example room temperature to solvent reflux, preferably elevated temperature, for example 55-65° C. Alternative examples of the method include reduction by catalytic hydrogenation using a noble metal catalyst such as Raney nickel, palladium, ruthenium, rhodium or platinum. Other reducing reagents include tin chloride, or reduction with Zn in AcOH. Examples of the solvent include alcoholic solvents such as methanol, ethanol and 1-propanol, preferably ethanol. The reaction time is not particularly limited and is usually 0.5 to 24 hours, and preferably 0.5 to 18 hours. The reaction temperature is usually room temperature.

Step B-(ii):

This is a step of obtaining a compound A-(13) from the compound A-(14) by condensing compound A-(14) with a carboxylic acid chloride.

The compound A-(13) can be obtained by converting the desired carboxylic acid to the corresponding acid chloride and then reacting the acid chloride with the compound A-(14). The reaction time is not particularly limited and is usually 0.5 to 48 hours, and preferably 0.5 to 12 hours. The acid chloride can be synthesized by a means known to a person skilled in the art. For example the desired carboxylic acid may converted to the corresponding acid chloride by reaction with thionyl chloride in the presence or absence of a solvent, for example dichloromethane, N,N'-dimethylimidazoline-2-one, NMP or DMF. One to two equivalents or a large excess of thionyl chloride may be used with respect to the desired carboxylic acid. Those skilled in the art will appreciate that the choice of reaction conditions employed may affect the outcome of the reaction, for example the conditions may affect whether the acid chloride reacts with the aniline or the isothiourea moieties. Those skilled in the art will appreciate that the reaction of thionyl chloride with a carboxylic acid results in the concomitant formation of 1 equivalent of hydrochloric acid in addition to the formation of the desired acid chloride. Those skilled in the art will appreciate that the current conditions do not employ a method of removing the thus formed hydrochloric acid. The hydrochloric acid formed in this reaction may or may not affect the selectivity of the reaction which may or may not result in a beneficial outcome. The reaction time is not particularly limited and is usually 0.5 to 48 hours, and preferably 0.5 to 12 hours. The reaction temperature is −30° C. to reflux, and preferably −10° C. to room temperature. The acid chloride may also be formed by treating the acid with oxalyl chloride in a solvent such as dichloromethane in the presence of DMF. The reaction temperature is −30° C. to room temperature, and preferably −10° C. to room temperature.

C. General Preparation Method C:

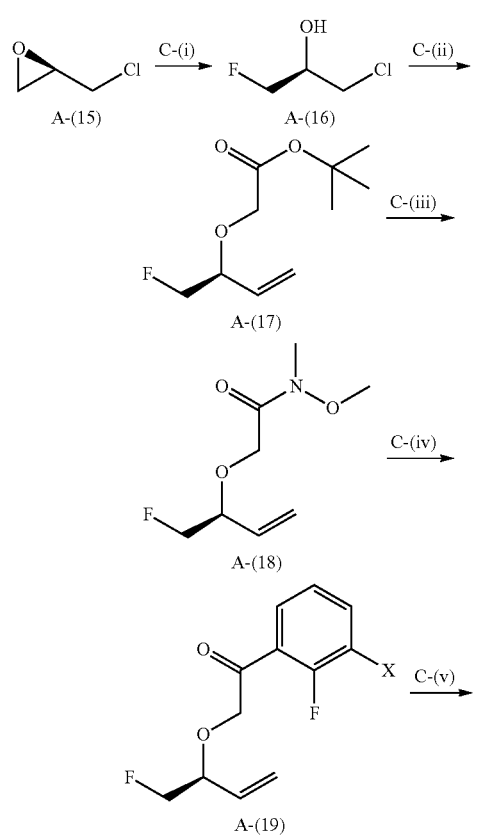

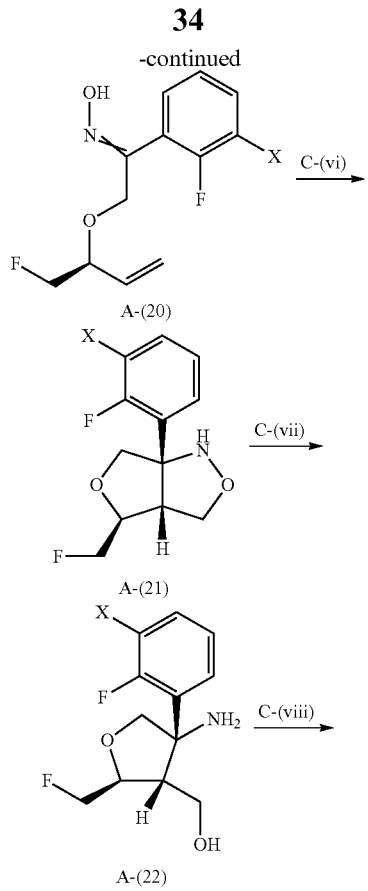

In the formula, X is as defined above.

General Preparation Method C is an alternative method for preparing a compound A-(24) which is a derivative of the compound A-(7), when R is $CH_2F$, according to the present invention from a compound A-(15) as a raw material through multiple steps of Step C-(i) to Step C-(ix).

The compound A-(15) is commercially available.

Step C-(i):

This step is a step of obtaining a compound A-(16) by opening the epoxide A-(15) with a fluoride equivalent to give the compound A-(16).

Specifically, the epoxide A-(15) can be opened by treating the epoxide with pyridine hydrofluoride. Preferably, the reaction should be conducted below room temperature, preferably −30-4° C. The solvent used in the reaction is not particularly limited insofar as it does not inhibit the reaction and allows the starting material to be dissolved therein to a certain extent. Examples of suitable solvents include, but are not limited to, dichloromethane. The addition of a base may prove beneficial or advantageous. Suitable examples of bases include, but are not limited to, pyridine. The reaction time is not particularly limited and is usually 5 minutes to 24 hours, preferably 0.5-6 hours.

Step C-(ii):

This step is a step of obtaining a compound A-(17) from alcohol A-(16) in a three step sequential process.

In the first step, the compound A-(16) is treated with a base in a solvent to form the corresponding (S)-2-(fluoromethyl) oxirane. Examples of suitable solvents for the reaction include THF. Examples of suitable bases include potassium hexamethyldisilazide. The reaction time is not particularly limited and is usually 0.5 to 72 hours, and preferably 0.5 to 24 hours. The reaction temperature is usually −20° C. to room temperature.

In the second and third step, the intermediate (S)-2-(fluoromethyl)oxirane is converted to the corresponding allylic alcohol by opening the epoxide with a sulfonium ylide to generate an intermediate allylic alkoxide which is then alkylated to give the compound A-(17). Those skilled in the art will appreciate that this transformation can be conducted in one pot or as two individual reactions. Those skilled in the art will appreciate the benefits and drawbacks of a one pot reaction compared to conducting two separate reactions and choose the best method for their requirements accordingly.

Specifically, the intermediate epoxide (S)-2-(fluoromethyl)oxirane can be opened by the anion of trimethylsulfonium iodide and resultant loss of dimethylsulfide to give the corresponding allylic alkoxide. Trimethylsulfonium iodide can be deprotonated with a suitable base, for example butyl lithium or lithium hexamethyldisilazide. The solvent used in the reaction is not particularly limited insofar as it does not interfere with the reaction. Examples of suitable solvents include THF. Those skilled in the art will appreciate that the word solvent in this instance is used to denote the liquid in which the reaction is effected and that the reagents may not be dissolved. Preferably the reaction should be conducted below room temperature, preferably −30-20° C. Upon addition the reaction may be warmed to room temperature to facilitate reaction. The reaction time is not particularly limited and is usually 5 minutes to 24 hours, preferably 1-6 hours.

Those skilled in the art will appreciate that the intermediate alkoxide generated from this reaction can be reacted with an alkylating agent directly, such as tert-butyl bromoacetate, and that this reaction may proceed with or without additional solvents. If additional solvents are required to facilitate reaction, then solvents such as DMF or NMP are suitable. The reaction temperature is not particularly limited. Suitable reaction temperatures include room temperature to 80° C., preferably room temperature. The reaction time is not particularly limited and is usually 5 minutes to 1 week, preferably 1-48 hours.

Those skilled in the art will appreciate that the intermediate alkoxide could be quenched, isolated and purified then subjected to independent alkylation conditions. This reaction can be performed under the same conditions as those usually used in O-alkylation reaction of an alcohol compound (such as the conditions described in Tetrahedron Lett. 2005, 46, 7751-7755). In this reaction, the compound A-(17) can be obtained by adding a base such as sodium hydride to a solution of the the intermediate alcohol in THF to prepare an alkoxide, and then reacting the alkoxide with the tert-butyl bromoacetate, for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 50° C.

A more preferable result such as an improved yield may be achieved by adding a salt such as tetrabutylammonium iodide in this reaction.

Alternatively, the compound A-(17) can be obtained from the the intermediate allylic alcohol by conducting the alkylation reaction under phase transfer conditions. The solvent for the reaction is not particularly limited insofar as it does not interfere with the reaction and is immiscible with water. Suitable examples of solvents include, but are not limited to dichloromethane and chloroform. The base used is water soluble, examples of such bases includes, but are not limited to, aqueous sodium hydroxide and aqueous potassium hydroxide. In addition, the reaction requires the addition of a phase transfer catalyst. Examples of suitable phase transfer catalysts include, but are not limited to, tetrabutylammonium salts, for example tetrabutylammonium hydrogen sulfate. The reaction time is not particularly limited and is usually 0.5 to 72 hours, and preferably 0.5 to 24 hours. The reaction temperature is usually—ice cold to 40° C.

Step C-(iii):

This step is a two step sequential reaction to obtain compound A-(18) from compound A-(17) by deprotecting the ester group then forming a Weinreb amide.

Specifically, the tert-butyl ester of compound A-(17) can be deprotected under the same conditions as those generally used in deprotection of a tert-butyl ester compound (such as the conditions described in a document such as T. W. Greene and P. G. M. Wuts, "Protective Groups in Organic Chemistry, Third Edition", John Wiley & Sons (1999), p. 404-408). In this reaction, the compound A-(17) can be reacted with an appropriate acid in a suitable solvent, such as formic acid, as solvent and acid, for example. The solvent used in the reaction is not particularly limited insofar as it does not inhibit the reaction and allows the starting material to be dissolved therein to a certain extent. The reaction time is not particularly limited and is usually 0.5 to 72 hours, and preferably 0.5 to 24 hours. The reaction temperature is usually ice-cold temperature to 60° C.

The intermediate acid can then be transformed to the Weinreb amide (Tetrahedron Lett. 1981, 22, 3815) by reaction of N,O-dimethylhydroxylamine hydrochloride under standard amide formation conditions, ie by condensing the intermediate acid with N,O-dimethylhydroxylamine hydrochloride using a condensing agent. Alternatively, this step is a step of obtaining a compound A-(18) by condensing the intermediate acid with N,O-dimethylhydroxylamine hydrochloride by acylation reaction.

The condensation reaction of the intermediate acid with N,O-dimethylhydroxylamine hydrochloride using a condensing agent can be performed under the same conditions as those usually used and described in the following documents. Examples of the known method include those in J. Med. Chem., 1991, 34 (1), 227-234; Heterocycles, 1991, 32 (10), 1968-1972 and J. Med. Chem., 1994, 37 (7), 998-1014.

The N,O-dimethylhydroxylamine may be a free form or a salt.

The solvent in this reaction is not particularly limited insofar as it does not inhibit the reaction. Examples of the solvent include tetrahydrofuran, 1,4-dioxane, ethyl acetate, methyl acetate, dichloromethane, chloroform, N,N-dimethylformamide, toluene, acetonitrile and xylene. Examples of the condensing agent include CDI (N,N'-carbonyldiimidazole), Bop (1H-1,2,3-benzotriazol-1-yloxy(tri(dimethylamino))phosphonium hexafluorophosphate), DCC (N,N-dicyclohexylcarbodiimide), diethylphosphoryl cyanide, PyBOP (benzotriazol-1-yloxytris(pyrrolidino)phosphonium hexafluorophosphate) and WSC/EDC.HCl (1-ethyl-3-(3-dimethylaminopropyl)carbodiimide hydrochloride). Suitable conditions include an agent to activate the acid, such as N,N'-carbonyl diimidazole. One equivalent to a large excess of N,O-dimethylhydroxylamine hydrochloride is used with respect to the intermediate acid. One equivalent to a large excess of an organic base such as triethylamine may be added where necessary.

The reaction time is not particularly limited and is usually 0.5 to 72 hours, and preferably 0.5 to 24 hours. The reaction temperature varies according to the raw material used, the solvent and the like and is not particularly limited. Ice-cold temperature to solvent reflux temperature is acceptable, ice cold to room temperature is preferable.

Step C-(iv):

This step is a step of obtaining a compound A-(19) by reaction of an organometallic (aryllithium reagent or a Grignard reagent) reagent with the Weinreb amide, A-(18) as described in Tetrahedron Lett. 1981, 22, 3815.

The reaction in this step can be performed under the same conditions as those described in Tetrahedron Lett. 1981, 22, 3815, for example.

The aryllithium reagent or the Grignard reagent can be prepared by a method known to a person skilled in the art. Specifically, the corresponding phenyl lithium reagent or phenyl magnesium (Grignard) reagent can be prepared by halogen-metal exchange between an aryl halide compound and a commercially available organometallic reagent such as an alkyllithium reagent such as n-, sec- or tert-butyllithium or a Grignard reagent such as isopropylmagnesium bromide, or metallic magnesium, for example.

The solvent used in this step varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene and toluene, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78-−60° C., although temperatures up to 0° C., 10° C. or even room temperature may be employed, depending on the reactivity of the two components, for example when the organometallic reagent is a Grignard reagent.

Step C-(v):

This step is a step of obtaining a compound A-(20) by oximation of the compound A-(19).

The reaction in this step can be performed under the same conditions as those usually used in oximation reaction of a carbonyl compound such as the conditions described in Org. Lett. 2007, 9, 753-756; Tetrahedron: Asymmetry 1994, 5, 1018-1028 and Tetrahedron, 1998, 54, 5868-5882.

Specifically, the compound A-(20) can be obtained by reacting the compound A-(19) with hydroxylamine or a hydroxylamine salt (such as hydroxylamine hydrochloride or hydroxylamine sulfate) in the presence of a base or in the absence of a base, for example.

The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step C-(vi):

This step is a step of obtaining a compound A-(21) by a thermal intramolecular cycloaddition of the alkenyl oxime A-(20).

The reaction is conducted in the presence of an additive, for example hydroquinone.

The solvent used in this reaction is not particularly limited insofar as it does not inhibit the reaction. Suitable reaction solvents include high boiling solvents such as xylenes. The reaction temperature is not particularly limited and is usually 80-200° C. or solvent reflux temperature. The reaction time is not particularly limited and is usually 0.5 to 48 hours, and preferably 0.5 to 24 hours.

Step C-(vii):

This step is a step of obtaining a compound A-(22) by subjecting the compound A-(21) to reductive cleavage reaction of the N—O bond.

This reaction can be conducted under the conditions described under General Preparation Method A, Step A-(ii).

Step C-(viii):

This step is a step of obtaining a compound A-(23) from the compound A-(22). The thiourea derivative A-(23) can be obtained from the compound A-(22) by a method known to a person skilled in the art.

This reaction can be conducted under the conditions described under General Preparation Method A, Step A-(iii).

Step C-(ix):

This step is a method of obtaining a compound A-(24) by cyclizing the compound A-(23). The compound A-(24) is a derivative of the compound A-(7) when R is $CH_2F$.

This reaction can be conducted under the conditions described under General Preparation Method A, Step A-(iv).

D. General Preparation Method D:

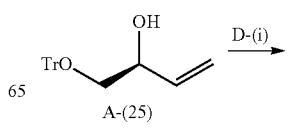

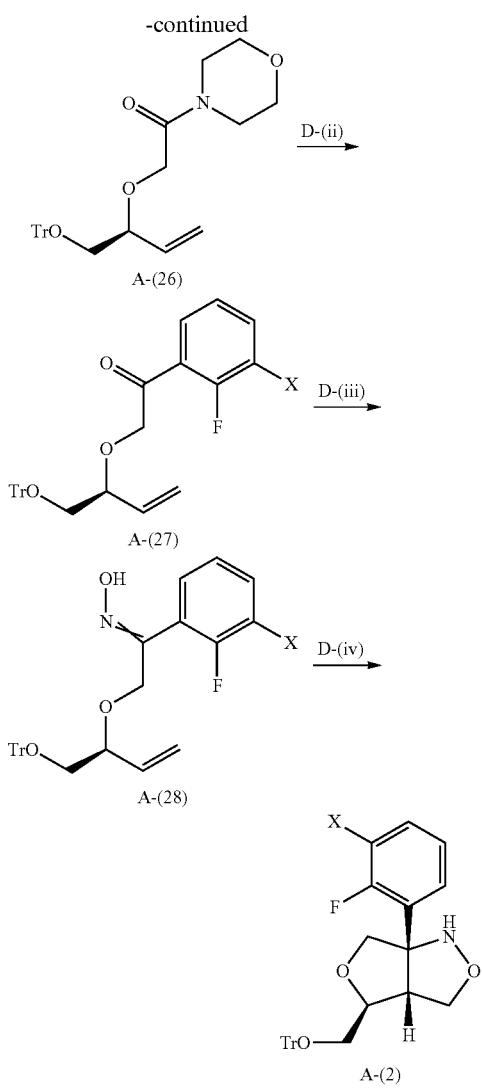

In the formula, X is as defined above.

General Preparation Method D is an alternative method for preparing a compound A-(2) when PG is Tr from a compound A-(25) as a raw material through multiple steps of Step D-(i) to Step D-(iv). A-(2) is an intermediate of the compound (I) according to the present invention The preparation of compound A-(25) is described in General Preparation Methods F and G.

Step D-(i):

This step is a step of obtaining a compound A-(26) by treating alcohol A-(25) with a base and an alkylating agent, (chloroacetyl)morpholine to give the compound A-(26).

Those skilled in the art will appreciate that this reaction can be performed under the same conditions as those usually used in O-alkylation reaction of an alcohol compound (such as the conditions described in Tetrahedron Lett. 2005, 46, 7751-7755). In this reaction, the compound A-(25) can be obtained by adding a base such as sodium hydride to a solution of the the intermediate alcohol in THF to prepare an alkoxide, and then reacting the alkoxide with the tert-butyl bromoacetate, for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 50° C.

A more preferable result such as an improved yield may be achieved by adding a salt such as tetrabutylammonium iodide in this reaction.

Alternatively, the compound A-(26) can be obtained from the compound A-(25) by conducting the alkylation reaction under phase transfer conditions. The solvent for the reaction is not particularly limited insofar as it does not interfere with the reaction and is immiscible with water. Suitable examples of solvents include, but are not limited to dichloromethane and chloroform. The base used is water soluble, examples of such bases includes, but are not limited to, aqueous sodium hydroxide and aqueous potassium hydroxide. In addition, the reaction requires the addition of a phase transfer catalyst. Examples of suitable phase transfer catalysts include, but are not limited to, tetrabutylammonium salts, for example tetrabutylammonium hydrogen sulfate. The reaction time is not particularly limited and is usually 0.5 to 72 hours, and preferably 0.5 to 24 hours. The reaction temperature is usually ice cold to 40° C.

Step D-(ii):

This step is a step of obtaining a compound A-(27) by reaction of an organometallic (aryllithium reagent or a Grignard reagent) reagent with compound A-(26) as described in Synlett 1997, 12, 1414.

The reaction in this step can be performed under the same conditions as those described in Synlett 1997, 12, 1414, for example.

The aryllithium reagent (including heterocyclic) or the Grignard reagent (including heterocyclic) can be prepared by a method known to a person skilled in the art. Specifically, the corresponding phenyl lithium reagent or phenyl magnesium (Grignard) reagent can be prepared by halogen-metal exchange between an aryl halide compound and a commercially available organometallic reagent such as an alkyllithium reagent such as n-, sec- or tert-butyllithium or a Grignard reagent such as isopropylmagnesium bromide, or metallic magnesium, for example. A more favourable result may be obtained by using isopropylmagnesium bromide-lithium chloride complex.

The solvent used in this step varies according to the starting material and the reagent used, and is not particularly limited insofar as it does not inhibit the reaction, allows the starting material to be dissolved therein to a certain extent, and is always inert during the reaction. Preferable examples of the solvent include organic solvents such as diethyl ether, tetrahydrofuran, 1,4-dioxane, 1,2-dimethoxyethane, benzene and toluene, and mixed solvents thereof. The reaction time is not particularly limited and is usually 0.1 to 48 hours, and preferably 0.1 to 12 hours. The reaction temperature varies according to the starting material, the reagent used and the like, and is preferably maintained to be low, for example, at −78-−60° C. although temperatures up to 0° C., 10° C. or even room temperature may be employed, depending on the reactivity of the two components, for example when the organometallic reagent is a Grignard reagent.

Step D-(iii):

This step is a step of obtaining a compound A-(28) by oximation of the compound A-(27).

The reaction in this step can be performed under the same conditions as those usually used in oximation reaction of a carbonyl compound such as the conditions described in Org. Lett. 2007, 9, 753-756; Tetrahedron: Asymmetry 1994, 5, 1018-1028 and Tetrahedron, 1998, 54, 5868-5882.

Specifically, the compound A-(28) can be obtained by reacting the compound A-(27) with hydroxylamine or a hydroxylamine salt (such as hydroxylamine hydrochloride or hydroxylamine sulfate) in the presence of a base or in the absence of a base, for example.

The solvent used in this reaction is not particularly limited insofar as it does not inhibit the reaction. Preferable examples of the solvent include organic solvents such as ethanol, methanol, tetrahydrofuran, 1,4-dioxane, 1,2-dimethoxyethane and dichloromethane, and mixtures of these solvents and water. Examples of the base used include sodium acetate, pyridine, sodium hydroxide, cesium hydroxide, barium hydroxide and 2,6-lutidine. The reaction time is not particularly limited and is usually 5 minutes to 24 hours, and preferably 5 minutes to 12 hours. The reaction temperature is usually −20° C. to solvent reflux temperature, and more preferably 0° C. to solvent reflux temperature.

Step D-(iv):

This step is a step of obtaining a compound A-(2) when PG is Tr by a thermal intramolecular cycloaddition of the alkenyl oxime A-(28).

This reaction can be conducted under the conditions described under General Preparation Method C, Step C-(vi).

E. General Preparation Method E:

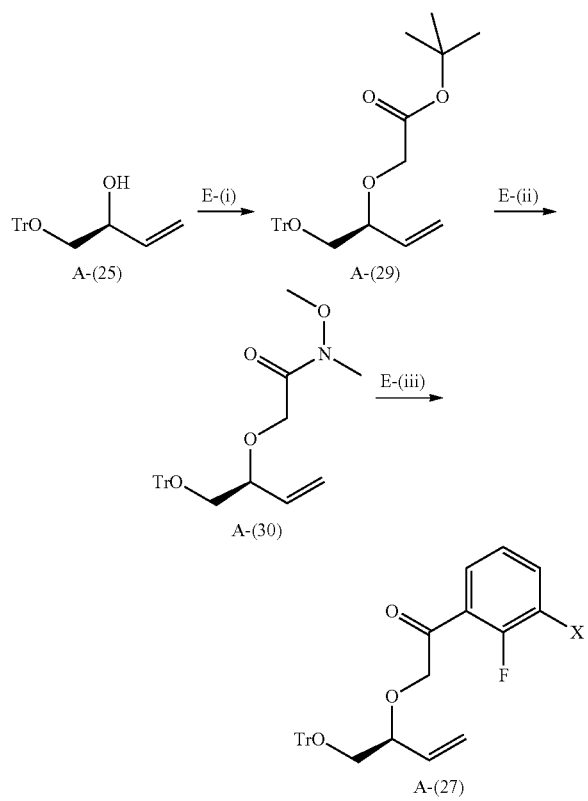

In the formula, X is as defined above.

General Preparation Method E is an alternative method for preparing a compound A-(27) which is an intermediate of the compound (I), according to the present invention from a compound A-(25) as a raw material through multiple steps of Step E-(i) to Step E-(iii).

The preparation of compound A-(25) is described in General Preparation Methods F and G.

Step E-(i):

This step is a step of alkylating a compound A-(25) by treating alcohol A-(25) with a base and an alkylating agent, tert-butylbromo acetate to give the compound A-(29).

Those skilled in the art will appreciate that this reaction can be performed under the same conditions as those usually used in O-alkylation reaction of an alcohol compound (such as the conditions described in Tetrahedron Lett. 46 (2005) 45, 7751-7755). In this reaction, the compound A-(25) can be obtained by adding a base such as sodium hydride to a solution of the the intermediate alcohol in THF to prepare an alkoxide, and then reacting the alkoxide with the tert-butyl bromoacetate, for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 50° C.

A more preferable result such as an improved yield may be achieved by adding a salt such as tetrabutylammonium iodide in this reaction.

Alternatively, the compound A-(29) can be obtained from the compound A-(25) by conducting the alkylation reaction under phase transfer conditions. The solvent for the reaction is not particularly limited insofar as it does not interfere with the reaction and is immiscible with water. Suitable examples of solvents include, but are not limited to dichloromethane and chloroform. The base used is water soluble, examples of such bases include, but are not limited to, aqueous sodium hydroxide and aqueous potassium hydroxide. In addition, the reaction requires the addition of a phase transfer catalyst. Examples of suitable phase transfer catalysts include, but are not limited to, tetrabutylammonium salts, for example tetrabutylammonium hydrogen sulfate. The reaction time is not particularly limited and is usually 0.5 to 72 hours, and preferably 0.5 to 24 hours. The reaction temperature is usually ice cold to 40° C.

Step E-(ii):

This step is a two step sequential reaction to obtain compound A-(30) from compound A-(29) by deprotecting the ester group then forming a Weinreb amide.

This reaction can be conducted under the conditions described under General Preparation Method C, Step C-(iii).

Step E-(iii):

This step is a step of obtaining a compound A-(27) by reaction of an organometallic (aryllithium reagent or a Grignard reagent) reagent with compound A-(30) as described in Tetrahedron Lett. 1981, 22, 3815.

This reaction can be conducted under the conditions described under General Preparation Method C, Step C-(iv).

F. General Preparation Method F:

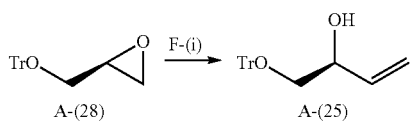

General Preparation Method F is a method for preparing a compound A-(25) which is an intermediate of the compound (I), according to the present invention from a compound A-(28) as a raw material through Step F-(i).

Compound A-(28) is commercially available.

This step is a step of obtaining a compound A-(25) by opening the epoxide A-(28) with a sulfonium ylide to generate an the allylic alcohol A-(25). Those skilled in the art will appreciate that the allylic alcohol A-(25) could be transformed directly to a compound such as A-(26), A-(29) or A-(30) without isolation. Those skilled in the art will appreciate that this transformation can be conducted in one pot or as two individual reactions. Those skilled in the art will appreciate the benefits and drawbacks of a one pot reaction compared to conducting two separate reactions and choose the best method for their requirements accordingly.

Specifically, the epoxide A-(28) can be opened by the anion of trimethylsulfonium iodide and resultant loss of dimethylsulfide to give the corresponding allylic alkoxide. Trimethylsulfonium iodide can be deprotonated with a suitable base, for example butyl lithium. The solvent used in the reaction is not particularly limited insofar as it does not interfere with the reaction. Examples of suitable solvents include THF. Those skilled in the art will appreciate that the word solvent in this instance is used to denote the liquid in which the reaction is effected and that the reagents may not be dissolved. Preferably the reaction should be conducted below room temperature, preferably −30-20° C. Upon addition the reaction may be warmed to room temperature to facilitate reaction. The reaction time is not particularly limited and is usually 5 minutes to 24 hours, preferably 1-6 hours.

Those skilled in the art will appreciate that the alkoxide generated from this reaction can be reacted with an alkylating agent directly, such as tert-butyl bromoacetate, to give A-(29) or 4-(chloroacetyl)-morpholine to give A-(26) and that this reaction may proceed with or without additional solvents. If additional solvents are required to facilitate reaction, then solvents such as DMF or NMP are suitable. The reaction temperature is not particularly limited. Suitable reaction temperatures include room temperature to 80° C., preferably room temperature. The reaction time is not particularly limited and is usually 5 minutes to 1 week, preferably 1-48 hours.

Those skilled in the art will appreciate that the intermediate alkoxide could be quenched, isolated and purified then subjected to independent alkylation conditions. This reaction can be performed under the same conditions as those usually used in O-alkylation reaction of an alcohol compound (such as the conditions described in Tetrahedron Lett. 2005, 46, 7751-7755). In this reaction, the compound A-(29) can be obtained by adding a base such as sodium hydride to a solution of the the intermediate alcohol in THF to prepare an alkoxide, and then reacting the alkoxide with the tert-butyl bromoacetate, for example. The solvent used in the reaction is not particularly limited insofar as it does not inhibit the reaction and allows the starting material to be dissolved therein to a certain extent. Examples of the solvent include solvents such as THF, DMF and dimethyl sulfoxide. The reaction can be performed by causing 1 to 3 equivalents of an appropriate base to act in the presence of such a solvent. Examples of the base used include sodium hydride, potassium hydride and t-butoxypotassium. The reaction time is not particularly limited and is usually 0.5 to 72 hours, and preferably 0.5 to 12 hours. The reaction temperature is usually −20° C. to 50° C.

A more preferable result such as an improved yield may be achieved by adding a salt such as tetrabutylammonium iodide in this reaction.

G. General Preparation Method G:

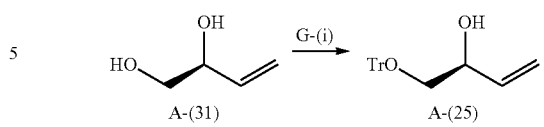

General Preparation Method G is an alternative method for preparing a compound A-(25) which is an intermediate of the compound (I), according to the present invention from a compound A-(31) as a raw material through Step G-(i).

Compound A-(31) is commercially available in racemic form. Those skilled in the art will appreciate that the compound A-(31) can be used in racemic or enantiomerically pure form.

Specifically, this step is a step of selectively protecting the primary alcohol of compound A-(31) and can be accomplished with a range of protecting groups known to those skilled in the art. Those skilled in the art will appreciate that often a large protecting group is selected for this type of transformation.

One example of such a protecting group is the trityl (triphenylmethyl) protecting group.

Those skilled in the art will appreciate that various suitable alcohol protecting groups could be selected and that the choice of protecting group is influenced by its chemical stability and conditions required for deprotection. Suitable protecting groups are described in T. W. Greene and P. G. M. Wuts, "Protective Groups in Organic Chemistry, Third Edition", John Wiley & Sons (1999).

When the protecting group is trityl (triphenylmethyl), suitable conditions for the deprotection can be found in T. W. Greene and P. G. M. Wuts, "Protective Groups in Organic Chemistry, Third Edition", John Wiley & Sons (1999), P. 102-104.

For example, a compound A-(25) can be prepared from A-(31) by treating compound A-(31') with trityl chloride (triphenylmethyl chloride). The solvent used in the reaction is not particularly limited insofar as it does not inhibit the reaction and allows the starting material to be dissolved therein to a certain extent. Examples of the solvent include toluene or dichloromethane. Those skilled in the art will appreciate that the use of a base may facilitate reaction or improve reaction yields. Examples of suitable bases include, but are not limited to, triethylamine and diisopropylethylamine. The reaction time is not particularly limited and is usually 0.5 to 72 hours, and preferably 0.5 to 24 hours. The reaction temperature is usually ice-cold temperature to solvent reflux temperature, and preferably ice cold to 40° C.

The present invention will be described more specifically below with reference to Examples, Preparation Examples and Test Example. However, the present invention is not limited thereto. The abbreviations used in Examples are conventional abbreviations known to a person skilled in the art. Some abbreviations are shown below:

LCMS, LC/MS & LC-MS (liquid chromatography/mass spectrometry); MS (mass spectrometry); MDAP (mass directed auto purification); NMR (nuclear magnetic resonance); s, d, t, dd, m, br (singlet, doublet, triplet, doublet of doublets, multiplet, broad); Ph, Me, Et, Pr, Bu, Bn (phenyl, methyl, ethyl, propyl, butyl, benzyl); THF (tetrahydrofuran); DCM (dichloromethane); DMF (N,N-dimethylformamide); h, hr, hrs (hours); EDC & EDAC (N-3-(dimethylaminopropyl)-N'ethylcarbodiimide hydrochloride); DMAP (4-N,N-dimethylaminopyridine); DMSO (dimethylsulfoxide); UV (ultraviolet); RT & rt (room temperature); Rt (retention time); min & mins (minutes); EtOAc (ethyl acetate); Et$_2$O (diethyl ether); MeCN (acetonitrile); EtOH (ethanol); MeOH (methanol); PhCH₃ & PhMe (toluene); tlc (thin layer chromatography); TFA (trifluoroactic acid); NaOH (sodium hydroxide); HCl (hydrochloric acid); NMP (N-methylpyrrolidinone or 1-methyl-2-pyrrolidinone); HPLC (high performance liquid chromatography); TBAF (tetrabutylammonium fluoride); BuLi (n-butyl lithium); PyBOP: benzotriazol-1-yloxytris (pyrrolidino)phosphonium hexafluorophosphate; $Pd_2dba_3$: tris(dibenzylideneacetone)dipalladium; $Pd(t-Bu_3P)_2$: bis(tri-t-butylphosphine)palladium; TFA: trifluoroacetic acid; pTLC: preparative thin-layer chromatography; HRMS (high resolution mass spectrometry); Tr or Trt (trityl or triphenylmethyl).

¹H NMR spectra were recorded on a Bruker AM series spectrometer operating at a (reported) frequency of 400 MHz. Chemical shifts in proton nuclear magnetic resonance spectra are recorded in δ units (ppm) relative to tetramethylsilane and coupling constants (J) are recorded in Hertz (Hz). Patterns are designated as s: singlet, d: doublet, t; triplet, br; broad.

The "room temperature" in the following Examples and Preparation Examples typically refers to about 10° C. to about 35° C. "%" indicates wt % unless otherwise specified.

Chemical names were generated from chemical structures using ChemBioDraw Ultra 11.0 and 12.0.

DESCRIPTION OF FIGURES

FIG. 1 is a Typical Chromatogram from a Chiral HPLC Isolation of Compound 4-(9).

EXAMPLE 1

Synthesis of N-(3-((4aS,5S,7aS)-2-amino-5-(difluoromethyl)-4a,5,7,7a-tetrahydro-4H-furo[3,4-d][1,3]thiazin-7a-yl)-4,5-difluorophenyl)-5-methoxypyrazine-2-carboxamide (Example 1-(14))

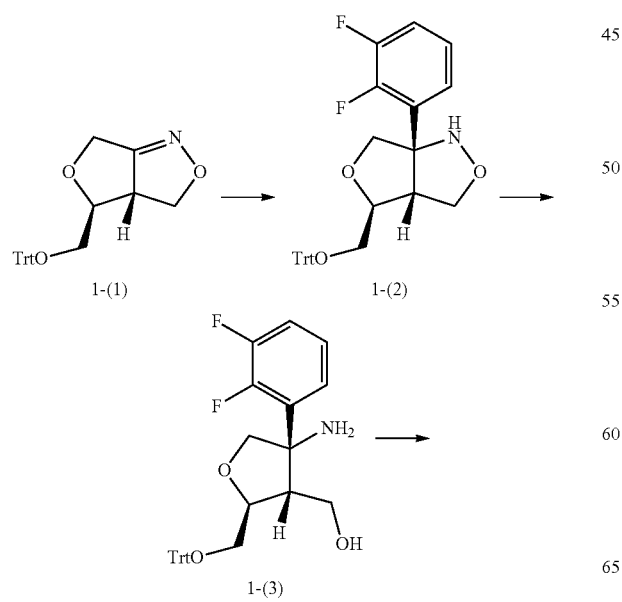
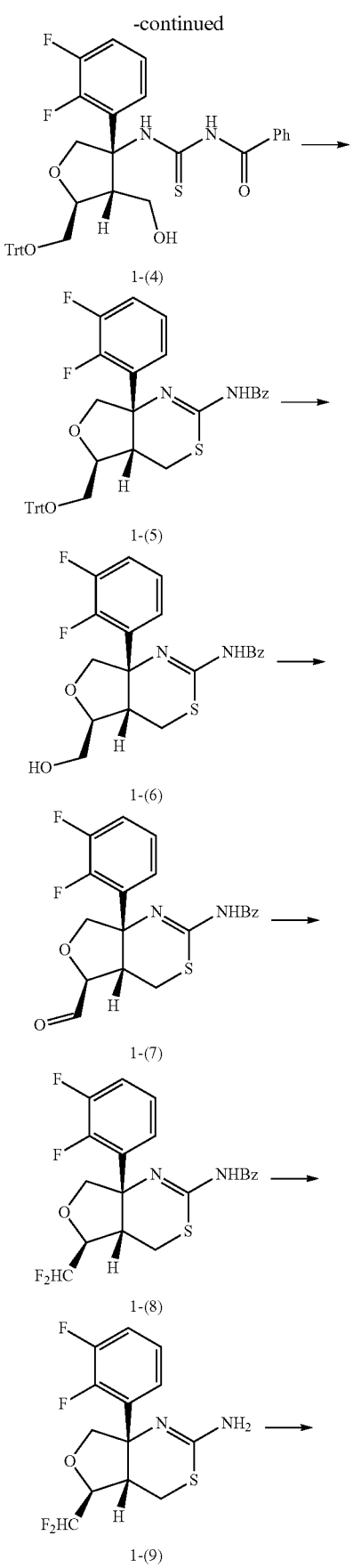

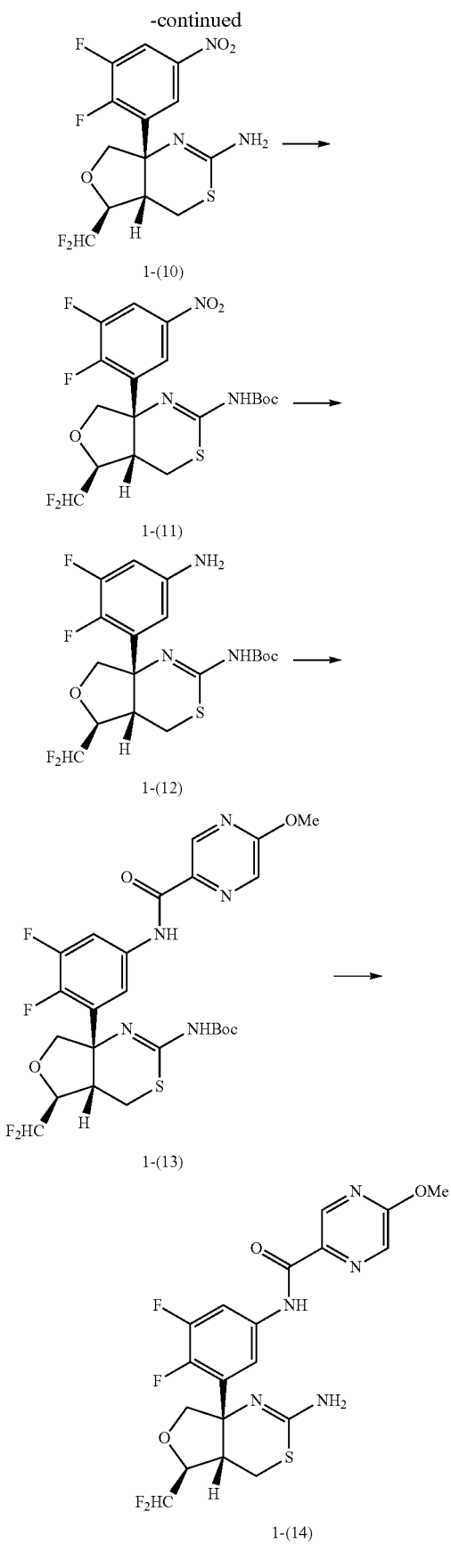

1-(2) Synthesis of (3aR,4S,6aS)-6a-(2,3-difluorophenyl)-4-((trityloxy)methyl)hexahydrofuro[3,4-c]isoxazole A solution of n-butyllithium in hexane (2.50 M; 29.8 mL) was added dropwise to a solution containing 1-bromo-2,3-fluorobenzene (2.93 mL) in THF/toluene (15 mL/150 mL) under a $N_2$ atmosphere at −78° C. The reaction solution was stirred at the same temperature for 30 min. Boron trifluoride-diethyl ether complex (9.2 mL) and a solution containing (3aR,4S)-4-((trityloxy)methyl)-3,3a,4,6-tetrahydrofuro[3,4-c]isoxazole (17.0 g) in toluene (50 mL) were then added dropwise to the reaction solution sequentially at the same temperature. After stirring at the same temperature for 60 min, aqueous $NH_4Cl$ (sat., 50 mL) was carefully added to the reaction solution, followed by warming to RT. Brine (200 mL) was then added to the reaction solution, and the mixture was extracted with EtOAc (3×200 mL). The combined organic layers were dried over anhydrous $MgSO_4$, and the insoluble matter was separated by filtration. The filtrate was concentrated and the residue was purified by silica gel column chromatography (gradient from 0% to 20% EtOAc in DCM: Hexanes 1:3) to obtain the title compound (15.51 g). $^1$H-NMR (400 MHz, $CDCl_3$) δ ppm 3.18-3.38 (m, 2H), 3.44-3.54 (m., 1H), 3.83-3.99 (m, 2H), 4.04-4.38 (br. s., 2H), 5.35 (s, 1H), 7.03-7.51 (m, 18H)

1-(3) ((2S,3R,4S)-4-amino-4-(2,3-difluorophenyl)-2-((trityloxy)methyl)tetrahydrofuran-3-yl)methanol Zinc powder (20.0 g) was added to a solution containing (3aR,4S,6aS)-6a-(2,3-difluorophenyl)-4-((trityloxy)methyl)hexahydrofuro[3,4-c]isoxazole, obtained in Preparation Example 1-(2), (15.51 g) in acetic acid (120 mL) at 0° C. The reaction solution was allowed to warm to RT and stirred for 18 h. The insoluble matter was separated by filtration through Celite®, washing with acetic acid (100 mL) and AcOEt (300 mL), and the filtrate was concentrated. Saturated aqueous $NaHCO_3$ solution was added carefully to neutralize the residue, and the mixture was extracted with EtOAc (3×200 mL). The combined organic layers were dried over $MgSO_4$ and evaporated to obtain the title compound (15.42 g). $^1$H-NMR (400 MHz, $CDCl_3$) δ (ppm): 2.60-2.68 (m, 1H), 2.85 (br s, 3H), 3.29 (d, J=4.8 Hz, 2H), 3.66 (dd, J=12.1, 4.8 Hz, 1H), 3.89-3.99 (m, 2H), 4.31 (d, J=9.1 Hz, 1H), 4.34-4.40 (m, 1H), 7.04-7.19 (m, 2H), 7.20-7.33 (m, 10H), 7.39-7.50 (m, 6H)

1-(4) N-(((3S,4R,5S)-3-(2,3-difluorophenyl)-4-(hydroxymethyl)-5-((trityloxy)methyl)tetrahydrofuran-3-yl)carbamothioyl)benzamide Benzoyl isothiocyanate (6 g) was added dropwise to a solution containing ((2S,3R,4S)-4-amino-4-(2,3-difluorophenyl)-2-((trityloxy)methyl)tetrahydrofuran-3-yl)methanol, obtained in Preparation Example 1-(3), (15.42 g) in $CH_2Cl_2$ (80 mL), and the mixture was stirred at RT for 18 h. EtOAc was added and the mixture was extracted with $NaHCO_3$ (3×100 mL), dried over $MgSO_4$, evaporated, and the residue was purified by silica gel column chromatography (0% to 30% EtOAc in hexanes) to obtain the title compound (19.06 g). $^1$H-NMR (400 MHz, $CDCl_3$) δ (ppm): 3.00 (t, J=6.2 Hz, 1H), 3.08-3.17 (m, 1H), 3.26 (dd, J=10.2, 4.2 Hz, 1H), 3.38 (dd, J=10.2, 3.9 Hz, 1H), 3.73-3.95 (m, 2H), 4.04-4.12 (m, 1H), 4.54 (d, J=9.6 Hz, 1H), 4.69 (d, J=9.9 Hz, 1H), 7.05-7.68 (m, 21H) 7.88 (d, J=7.1 Hz, 2H), 8.88 (s, 1H), 11.83 (s, 1H)

1-(5) N-((4aS,5S,7aS)-7a-(2,3-difluorophenyl)-5-((trityloxy)methyl)-4a,5,7,7a-tetrahydro-4H-furo[3,4-d][1,3]thiazin-2-yl)benzamide N-(((3S,4R,5S)-3-(2,3-difluorophenyl)-4-(hydroxymethyl)-5-((trityloxy)methyl)tetrahydrofuran-3-yl)carbamothioyl)benzamide, obtained in Preparation Example 1-(4), (19.06 g) was dissolved in DCM (75 mL). Pyridine (8.6 mL) was added, and the mixture cooled to 0° C. Trifluoromethanesulfonic anhydride (9.6 mL) was added dropwise and the reaction was allowed to stir at 0° C. After 90 min, the reaction was quenched by the careful addition of NaHCO$_3$ (sat., aq., 250 mL) and extracted with EtOAc (3×250 mL). The combined organic extracts were dried over MgSO$_4$, concentrated in vacuo and purified by silica gel column chromatography (0% to 30% EtOAc/hex) to obtain the title compound (14.52 g). $^1$H NMR (400 MHz, CDCl$_3$) δ ppm 2.63-2.76 (m, 1H), 3.07-3.24 (m, 2H), 3.32-3.52 (m, 3H), 3.99-4.11 (m, 1H), 4.53-4.63 (m, 2H), 7.09-7.56 (m, 21H), 8.08-8.30 (m, 2H)

1-(6) Synthesis of N-((4aS,5S,7aS)-7a-(2,3-difluorophenyl)-5-(hydroxymethyl)-4a,5,7,7a-tetrahydro-4H-furo[3,4-d][1,3]thiazin-2-yl)benzamide N-((4aS,5S,7aS)-7a-(2,3-difluorophenyl)-5-((trityloxy)methyl)-4a,5,7,7a-tetrahydro-4H-furo[3,4-d][1,3]thiazin-2-yl)benzamide, obtained in preparation example 1-(5), (8.42 g) was suspended in methanol (100 mL) and water (3 mL) and conc. hydrochloric acid (5 mL) were added. The reaction mixture was stirred vigorously overnight, and then concentrated under reduced pressure to a volume of about 30 mL. The mixture was then carefully neutralised with NaHCO$_3$ (sat., aq., 100 mL) and extracted with EtOAc (3×100 mL). The combined organic portions were dried over MgSO$_4$, evaporated, and the residue purified by silica gel column chromatography (0% to 50% EtOAc in hexanes) to afford the title compound (4.20 g). $^1$H NMR (400 MHz, CDCl$_3$) δ ppm 1.94 (br. s., 1H), 2.83 (d, J=10.6 Hz, 1H), 3.14-3.49 (m, 2H), 3.77 (d, J=8.8 Hz, 1H), 3.97 (dd, J=11.7, 2.7 Hz, 1H), 4.08 (d, J=6.3 Hz, 1H), 4.46-4.63 (m, 2H), 7.07-7.25 (m, 3H), 7.37-7.60 (m, 3H), 8.00-8.26 (m, 2H)

1-(7) Synthesis of N-((4aS,5S,7aS)-7a-(2,3-difluorophenyl)-5-formyl-4a,5,7,7a-tetrahydro-4H-furo[3,4-d][1,3]thiazin-2-yl)benzamide N-((4aS,5S,7aS)-7a-(2,3-difluorophenyl)-5-(hydroxymethyl)-4a,5,7,7a-tetrahydro-4H-furo[3,4-d][1,3]thiazin-2-yl)benzamide, obtained in preparation example 1-(6), (4.20 g) was dissolved in DCM (60 mL) and the solution was cooled to 0° C. 1,1,1-Tris(acetyloxy)-1,1-dihydro-1,2-benziodoxol-3(1H)-one (5.50 g) was added portionwise over 10 min, and the reaction mixture was allowed to warm to RT. After stirring for 2 h, NaHCO$_3$ (sat., aq., 100 mL) was added, and the mixture was extracted with DCM (3×150 mL). The combined organic portions were dried over MgSO$_4$ and evaporated to afford the title compound (3.04 g, approx. purity 60%) which was used in the subsequent step without purification. $^1$H NMR (400 MHz, CDCl$_3$) δ ppm 2.97 (dd, J=14.0, 4.2 Hz, 1H), 3.23 (d, J=11.6 Hz, 1H), 3.29-3.38 (m, 1H), 4.08-4.18 (m, 1H), 4.56-4.83 (m, 2H), 7.11-7.24 (m, 3H), 7.39-7.64 (m, 3H), 7.98-8.18 (m, 2H), 9.96 (d, J=1.0 Hz, 1H).

1-(8) Synthesis of N-((4aS,5S,7aS)-5-(difluoromethyl)-7a-(2,3-difluorophenyl)-4a,5,7,7a-tetrahydro-4H-furo[3,4-d][1,3]thiazin-2-yl)benzamide N-((4aS,5S,7aS)-7a-(2,3-difluorophenyl)-5-formyl-4a,5,7,7a-tetrahydro-4H-furo[3,4-d][1,3]thiazin-2-yl)benzamide, obtained in preparation example 1-(7), (3.04 g, approx purity 60%) was dissolved in DCM (50 mL) and the solution cooled to 0° C. Diethylaminosulfur trifluoride (0.99 mL) was then added dropwise, and the reaction mixture was allowed to warm and stir at RT. After 2 h, the reaction was quenched by the addition of NaHCO$_3$ (sat., aq., 100 mL) and extracted with DCM (2×150 mL). The combined organic portions were dried over MgSO$_4$, evaporated, and the residue was purified by silica gel column chromatography (5% to 50% EtOAc in hexanes) to afford the title compound (757 mg). $^1$H NMR (400 MHz, CDCl$_3$) δ ppm 2.89 (dd, J=13.8, 3.7 Hz, 1H), 3.22 (d, J=13.1 Hz, 1H), 3.46-3.61 (m, 1H), 4.02 (d, J=8.8 Hz, 1H), 4.56 (d, J=9.1 Hz, 1H), 4.62-4.72 (m, 1H), 5.86-6.18 (m, 1H), 7.08-7.25 (m, 3H), 7.40-7.63 (m, 3H), 7.96-8.16 (br. s., 2H).

1-(9) Synthesis of (4aS,5S,7aS)-5-(difluoromethyl)-7a-(2,3-difluorophenyl)-4a,5,7,7a-tetrahydro-4H-furo[3,4-d][1,3]thiazin-2-amine N-((4aS,5S,7aS)-5-(difluoromethyl)-7a-(2,3-difluorophenyl)-4a,5,7,7a-tetrahydro-4H-furo[3,4-d][1,3]thiazin-2-yl)benzamide, obtained in Preparation Example 1-(8), (891 mg) was dissolved in methanol (10 mL), 1,8-diazabicyclo[5.4.0]undec-7-ene (1.02 g) was added, and the solution was heated to reflux (heating block temperature 70° C.). After 16 h, the reaction mixture was cooled, concentrated under reduced pressure, and the residue purified by silica gel column chromatography (0% to 80% EtOAc in hexanes) to afford the title compound (565 mg). $^1$H NMR (400 MHz, CDCl$_3$) δ ppm 2.88 (dd, J=13.4, 4.0 Hz, 1H), 3.13 (dd, J=13.6, 3.3 Hz, 1H), 3.24 (dt, J=7.7, 3.7 Hz, 1H), 3.89 (d, J=8.3 Hz, 1H), 4.33-4.70 (m, 4H), 5.94 (td, J=56.3, 3.8 Hz, 1H), 7.05-7.25 (m, 3H)

1-(10) Synthesis of (4aS,5S,7aS)-7a-(2,3-difluoro-5-nitrophenyl)-5-(difluoromethyl)-4a,5,7,7a-tetrahydro-4H-furo[3,4-d][1,3]thiazin-2-amine (4aS,5S,7aS)-5-(difluoromethyl)-7a-(2,3-difluorophenyl)-4a,5,7,7a-tetrahydro-4H-furo[3,4-d][1,3]thiazin-2-amine, obtained in Preparation Example 1-(9), (565 mg) was dissolved in TFA (3 mL), and the solution was cooled to 0° C. Sulfuric acid (conc., 0.8 mL) was added, followed by fuming nitric acid (0.08 mL) dropwise over 20 mins. After stirring at 0° C. for 90 min, the reaction mixture carefully neutralized with NaHCO$_3$ (sat., aq., 50 mL) and extracted with EtOAc (3×100 mL), and the combined organic portions dried over MgSO$_4$ and evaporated. The residue was purified by silica gel column chromatography (0% to 80% EtOAc in hexanes) to afford the title compound (700 mg, purity approx. 80%) which was used in the subsequent step without purification. $^1$H NMR (400 MHz, CDCl$_3$) δ ppm 3.04 (dd, J=14.0, 3.9 Hz, 1H), 3.23-3.31 (m, 1H), 3.59 (d, J=3.0 Hz, 1H), 4.23 (d, J=9.9 Hz, 1H), 4.44-4.60 (m, 2H), 6.02 (t, J=57.6 Hz, 1H), 8.02-8.26 (m, 2H)

1-(11) Synthesis of tert-butyl ((4aS,5S,7aS)-7a-(2,3-difluoro-5-nitrophenyl)-5-(difluoromethyl)-4a,5,7,7a-tetrahydro-4H-furo[3,4-d][1,3]thiazin-2-yl)carbamate (4aS,5S,7aS)-7a-(2,3-difluoro-5-nitrophenyl)-5-(difluoromethyl)-4a,5,7,7a-tetrahydro-4H-furo[3,4-d][1,3]thiazin-2-amine, obtained in Preparation Example 1-(10), (700 mg, approx. purity 80%) was dissolved in THF (10 mL), di-tert-butyl dicarbonate (450 mg) was added portionwise over 20 mins and the reaction mixture was heated to 60° C. Two additional portions of di-tert-butyl dicarbonate (250 mg)

were added at two-hourly intervals. After 6 h, the reaction mixture was cooled and sodium bicarbonate (sat., aq., 20 mL) was added. The mixture was then extracted with EtOAc (3×50 mL) and the combined organic portions were dried over MgSO$_4$ and evaporated. The residue was purified by silica gel column chromatography (0% to 50% EtOAc in hexanes) to afford the title compound (489 mg). $^1$H NMR (400 MHz, CDCl$_3$) δ ppm 1.53 (s, 9H), 2.81 (dd, J=13.9, 4.0 Hz, 1H), 2.98 (dd, J=13.9, 2.3 Hz, 1H), 3.41 (dd, J=7.3, 3.5 Hz, 1H), 3.86 (d, J=8.3 Hz, 1H), 4.46 (d, J=8.6 Hz, 1H), 4.52-4.71 (m, 1H), 6.00 (t, J=54.6 Hz, 1H), 7.36 (br. s., 1H), 8.03-8.22 (m, 2H) 1-(12) Synthesis of tert-butyl ((4aS,5S,7aS)-7a-(5-amino-2,3-difluorophenyl)-5-(difluoromethyl)-4a,5,7,7a-tetrahydro-4H-furo[3,4-d][1,3]thiazin-2-yl)carbamate tert-butyl ((4aS,5S,7aS)-7a-(2,3-difluoro-5-nitrophenyl)-5-(difluoromethyl)-4a,5,7,7a-tetrahydro-4H-furo[3,4-d][1,3]thiazin-2-yl)carbamate, obtained in Preparation Example 1-(11), (489 mg) was dissolved in ethanol (10 mL) and tin chloride dihydrate (800 mg) was added. After stirring for 16 h, NaOH (2N aq., 20 mL) was added and the mixture extracted with EtOAc (2×50 mL). The combined organic portions were dried over MgSO$_4$ and evaporated to the title compound (457 mg). $^1$H NMR (400 MHz, CDCl$_3$) δ ppm 1.52 (m, 9H), 2.79 (dd, J=13.8, 3.9 Hz, 1H), 3.08 (d, J=13.6 Hz, 1H), 3.34 (d, J=3.5 Hz, 1H), 3.70 (br. s., 2H), 3.85 (d, J=8.3 Hz, 1H), 4.40-4.62 (m, 2H), 5.76-6.14 (dt, J=4.0, 56.6 Hz, 1H), 6.28-6.38 (m, 1H), 6.45 (ddd, J=11.1, 6.3, 2.8 Hz, 1H)

1-(13) Synthesis of tert-butyl ((4aS,5S,7aS)-7a-(2,3-difluoro-5-(5-methoxypyrazine-2-carboxamido)phenyl)-5-(difluoromethyl)-4a,5,7,7a-tetrahydro-4H-furo[3,4-d][1,3]thiazin-2-yl)carbamate tert-butyl ((4aS,5S,7aS)-7a-(5-amino-2,3-difluorophenyl)-5-(difluoromethyl)-4a,5,7,7a-tetrahydro-4H-furo[3,4-d][1,3]thiazin-2-yl)carbamate, synthesized in preparation example 1-(13), (100 mg) was dissolved in DCM (2 mL) and 5-methoxypyrazine-2-carboxylic acid (50 mg), N,N-diisopropylethylamine (100 mg) and (1H-benzotriazol-1-yloxy)tripyrrolidin-1-yl)phosphonium hexafluorophosphate (175 mg) were added. The reaction mixture was stirred at RT for 3 days, and sodium bicarbonate (sat., aq., 25 mL) was added. The mixture was extracted with EtOAc (2×40 mL), the combined organic portions were dried over MgSO$_4$, evaporated and purified by silica gel chromatography (EtOAc/hexanes gradient) to afford the title compound (108 mg) as a white solid. $^1$H NMR (400 MHz, CDCl$_3$) δ ppm 1.54 (s, 9H), 2.82 (dd, J=13.5, 3.4 Hz, 1H), 3.08 (d, J=12.9 Hz, 1H), 3.33-3.45 (m, 1H), 3.84-3.93 (m, 1H), 4.10 (s, 3H), 4.46-4.65 (m, 2H), 5.97 (dt, J=3.8, 56.6 Hz, 1H), 7.08 (br. s., 1H), 7.27-7.36 (m, 1H), 8.14 (ddd, J=11.6, 7.0, 2.7 Hz, 1H), 8.20 (d, J=1.3 Hz, 1H), 9.04 (d, J=1.3 Hz, 1H), 9.55 (s, 1H)

1-(14) Synthesis of N-(344aS,5S,7aS)-2-amino-5-(difluoromethyl)-4a,5,7,7a-tetrahydro-4H-furo[3,4-d][1,3]thiazin-7a-yl)-4,5-difluorophenyl)-5-methoxypyrazine-2-carboxamide tert-butyl ((4aS,5S,7aS)-7a-(2,3-difluoro-5-(5-methoxypyrazine-2-carboxamido)phenyl)-5-(difluoromethyl)-4a,5,7,7a-tetrahydro-4H-furo[3,4-d][1,3]thiazin-2-yl)carbamate, synthesized in preparation example 1-(13), (108 mg) was dissolved in DCM (2 mL) and TFA (1 mL) was added. After stirring at RT for 2 h, the reaction mixture was evaporated and sodium bicarbonate (sat., aq., 25 mL) was added. The mixture was extracted with EtOAc (3×25 mL), and the combined organic portions dried over MgSO$_4$, evaporated, and purified by silica gel chromatography to afford the title compound as a white solid (45 mg). $^1$H NMR (400 MHz, MeOD) δ ppm 2.87-2.99 (m, 1H), 3.17-3.26 (m, 2H), 3.89 (d, J=8.8 Hz, 1H), 4.09 (s, 3H), 4.39-4.59 (m, 2H), 6.02 (dt, J=3.8, 55.8 Hz, 1H), 7.48-7.63 (m, 1H), 7.98 (ddd, J=12.1, 7.0, 2.7 Hz, 1H), 8.29 (d, J=1.3 Hz, 1H), 8.92 (d, J=1.5 Hz, 1H)

EXAMPLE 2

Synthesis of N-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-5-methoxypyrazine-2-carboxamide

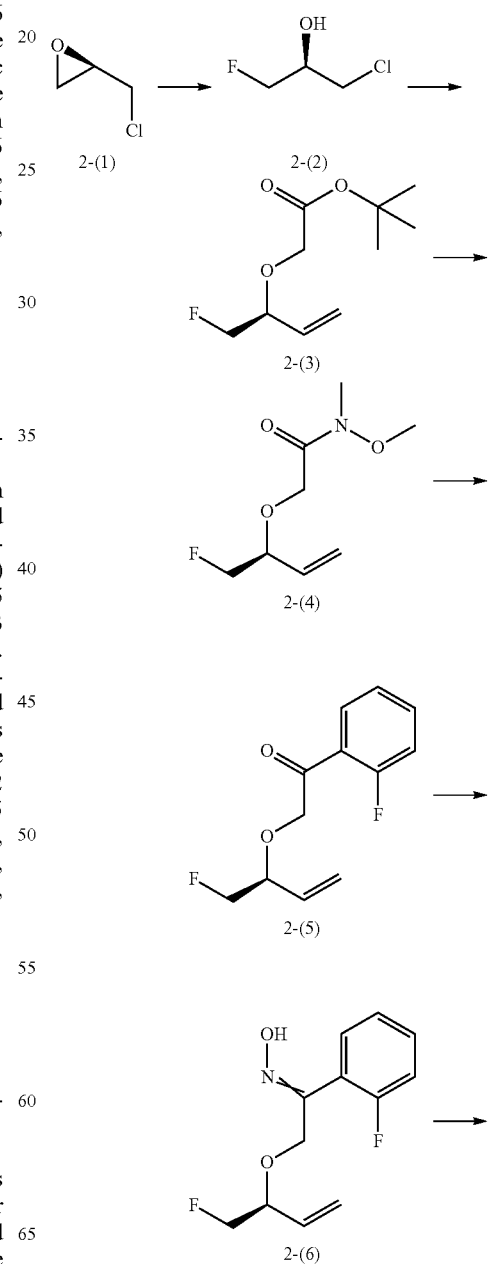

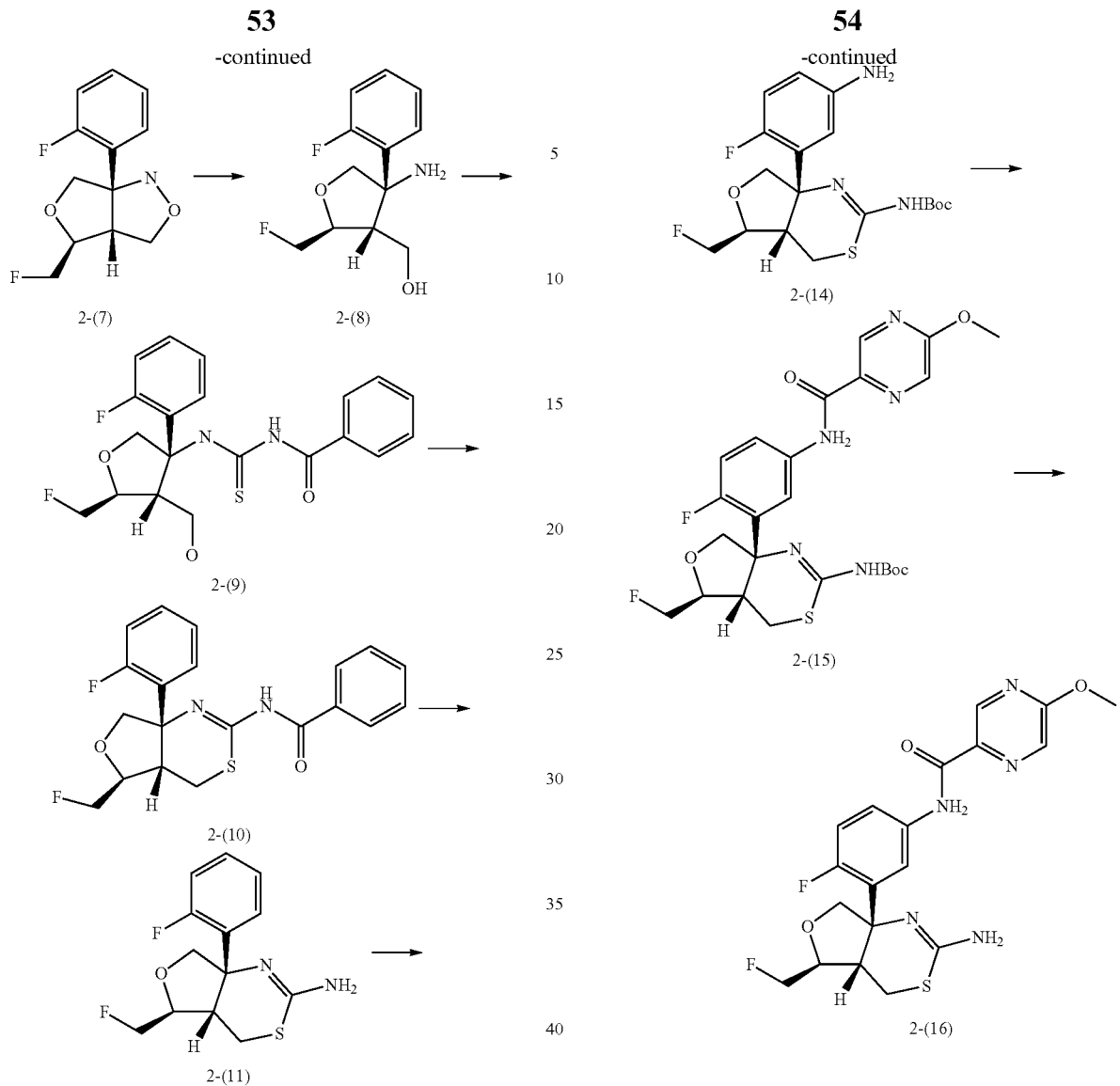

2-(2) Synthesis of (R)-1-chloro-3-fluoropropan-2-ol

Pyridine hydrofluoride (70% HF and 30% pyridine complex) (460 mL, 5.10 mol) was transferred into a 1 L polypropylene Erlenmayer flask with a magnetic teflon-coated stirring bar. The flask was cooled to −30° C. and the internal temperature was monitored using a PTFE-coated thermometer for the duration of the reaction. Pyridine (60 mL, 741.83 mmol) was injected in small portions in such a rate that the internal temperature did not exceed 0° C. The reaction vessel was then transferred into an ice bath and the internal temperature was brought to 0° C. (R)-2-(chloromethyl)oxirane (60 ml, 765.2 mmol) was added dropwise as a solution in DCM (60 ml) using a syringe pump/or a dropping funnel that had a needle attached to it. The addition was done over a period of 140 mins. It is important that the end of the needle (~2 cm) is immersed in the HF-pyridine mixture. During the addition the temperature increased from 0° C. to 4° C. The mixture was stirred for an additional 30 mins and was poured slowly onto a mixture of ice (1100 g)-water (600 mL)-NaCl (200 g)-DCM (500 mL). The organic layer was separated and the aqueous layer was extracted with DCM (8×300 mL). The combined organic extracts were stirred with NaHCO₃ (120 mL), dried over MgSO₄ and concentrated. (The temperature of the water bath was kept below 20° C. at the beginning of the evaporation and about 10° C. at the end with pressure at 150 mbar). The crude product (78.65 g) was obtained a yellow liquid. The above reaction was repeated on the same scale 13 times to produce 1020 g of crude material. The crude product was distilled under reduced pressure to give the title compound as a clear oil at 40-50° C./8 mbar (378.2 g). $^1$H NMR (400 MHz, CDCl$_3$)) δ ppm 2.36-2.56 (m, 1H) 3.61-3.73 (m, 2H) 4.03-4.16 (m, 1H) 4.47 (dd, J=4.80, 1.14 Hz, 1H) 4.59 (dd, J=4.80, 1.01 Hz, 1H)

2-(3) Synthesis of (S)-tert-butyl 2-((1-fluorobut-3-en-2-yl)oxy)acetate (R)-1-chloro-3-fluoropropan-2-ol (50.0 g, 444.37 mmol) was dissolved in tetrahydrofuran (150 mL) under nitrogen. The solution was cooled to −20° C. Potassium hexamethyldisilazide (89.8 g, 450.16 mmol) was added in small portions (9 portions ~10 g each) over 40 mins ensuring that the internal temperature remained between −5° C. to −10° C. The reaction was then allowed to warm to RT and stirred overnight under nitrogen.

Into a different flask, trimethylsulfonium iodide (181.35 g, 888.65 mmol) was dissolved in THF. The solution was cooled to −30° C. Lithium hexamethyldisilazide (888.65 mL, 1 M solution in THF, 888.65 mmol) was added over 25 mins. The internal temperature went from −30° C. to −26° C. upon the addition. The reaction was stirred at −30° C. for 30 mins. To this solution was added the (S)-2-(fluoromethyl)oxirane solution (that was prepared in the previous flask). The addition was done over 5 mins at −30° C. The reaction was then allowed to warm up to RT and stirred for 3 h. It was then cooled to 3° C. (internal temperature) using an ice bath and 1-methyl-2-pyrrolidinone (100 mL) was added. The internal temperature rose to 8° C. tert-Butyl bromoacetate (131.22 mL, 888.65 mmol) in 1-methyl-2-pyrrolidinone (100 mL) was added dropwise using a dropping funnel and ensuring the temperature remained between 17-20° C. The reaction was stirred in the ice bath for 10 mins until the temperature went to 5° C. The ice bath was removed and it was stirred at RT overnight. Water (2 L) was poured into the reaction mixture and followed by Et$_2$O (1 L). After stirring for 10 mins the two layers were separated and the aqueous layer was extracted with Et$_2$O (4×500 mL). The combined organic extracts were dried over MgSO$_4$ and concentrated. The crude product was purified by silica gel column chromatography using hexanes initially and then 5% EtOAc in hexanes to obtain the title compound as a yellow liquid (57 g, 63%).

The above reaction was repeated 3 times on the same scale to produce 168 g of the title compound. This was further purified by distillation under reduced pressure to give at 0.3 mbar and 80-95° C. the product as a clear liquid (93.88 g). $^1$H NMR (400 MHz, CDCl$_3$) δ ppm 1.48 (s, 9H) 4.01 (s, 1H) 4.05 (s, 1H) 4.12-4.22 (m, 1H) 4.36-4.44 (m, 1H) 4.48-4.57 (m, 1H) 5.33-5.51 (m, 2H) 5.67-5.82 (m, 1H)

2-(4) Synthesis of (S)-2-((1-fluorobut-3-en-2-yl)oxy)-N-methoxy-N-methylacetamide (S)-tert-butyl 2-((1-fluorobut-3-en-2-yl)oxy)acetate (96.26 g, 471.31 mmol) was cooled to 0° C. Formic acid (354 mL) was added. The mixture was allowed to warm to RT and stir overnight. The reaction mixture was then concentrated under reduced pressure (water bath temperature 40° C.). The residue was azeotroped with toluene (3×100 mL) to give the carboxylic acid as a dark brown oil. The residue was dissolved in DCM (720 mL), cooled in an ice-bath until the internal temperature was 3° C. N,N'-Carbonyl diimidazole (87.88 g, 542.00 mmol) was added portionwise over 10 mins ensuring that the internal temperature did not rise above 8° C. The ice bath was then removed and the mixture was stirred at RT for 48 mins. It was then cooled in an ice bath until the internal temperature was 3° C. N, 0-dimethyl hydroxylamine hydrochloride (55.17 g, 565.57 mmol) was added over 10 mins (internal temperature rose to 8° C.). The reaction mixture was allowed to warm to RT and stir overnight. 2N HCl (500 mL) was added and the two layers were separated. The aqueous layer was extracted with DCM (2×200 mL) and the combined organic portions were dried over MgSO$_4$ and evaporated. The crude product was purified by filtration through a pad of NH silica using EtOAc as the eluent to give the product as a pale yellow liquid (70 g, 366.10 mmol). $^1$H-NMR (400 MHz, CDCl$_3$) δ ppm 3.01 (s, 3H) 3.50 (s, 3H) 3.99-4.11 (m, 1H) 4.11-4.20 (m, 2H) 4.23-4.27 (m, 1H) 4.35-4.39 (m, 1H) 5.16-5.31 (m, 2H) 5.60 (ddd, J=17.43, 10.29, 7.26 Hz, 1H).

2-(5) Synthesis of ((S)-2-((1-fluorobut-3-en-2-yl)oxy)-1-(2-fluorophenyl)ethanone A solution of n-butyllithium in hexane (2.50 M; 176.52 mL, 441.29 mmol) was added dropwise over 20 mins to a solution of 2-bromofluorobenzene (49.00 mL, 451.88 mmol) in THF (670 mL) under a N$_2$ atmosphere at −78° C. The temperature of the reaction was kept below −60° C. during the addition. The yellow solution was stirred at −78° C. for 30 mins. (S)-2-((1-fluorobut-3-en-2-yl)oxy)-N-methoxy-N-methylacetamide (67.50 g, 353.03 mmol) was added dropwise as a solution in THF (100 mL) keeping the internal temperature below −60° C. The reaction was stirred at −78° C. for 45 mins. Aqueous NH$_4$Cl (200 mL) was added to the reaction solution and was allowed to warm up to RT and EtOAc (700 mL) was added. The two layers were separated. The aqueous layer was extracted with EtOAc (300 mL). The combined organic portions were washed with water 9300 mL), dried over MgSO$_4$, (40 g) and concentrated. The crude product was purified by silica gel column chromatography (1% to 10% EtOAc in hexanes) to obtain the title compound as a yellow liquid (63.78 g, 80%). $^1$H-NMR (400 MHz, CDCl$_3$) δ ppm 4.16-4.31 (m, 1H) 4.42-4.51 (m, 1H) 4.54-4.61 (m, 1H) 4.67-4.88 (m, 2H) 5.35-5.52 (m, 2H) 5.80 (ddd, J=17.43, 10.29, 7.26 Hz, 1H) 7.11-7.19 (m, 1H) 7.24-7.31 (m, 1H) 7.49-7.60 (m, 1H) 7.92-8.00 (m, 1H).

2-(6) Synthesis of (S)-2-((1-fluorobut-3-en-2-yl)oxy)-1-(2-fluorophenyl)ethanone oxime (S)-2-((1-fluorobut-3-en-2-yl)oxy)-1-(2-fluorophenyl)ethanone (63.25 g, 279.59 mmol) was dissolved in anhydrous methanol (620 mL) and hydroxylamine hydrochloride (25.26 g, 363.47 mmol) and sodium acetate (34.40 g, 419.39 mmol) were added. The reaction mixture was heated to 50° C. for 90 min, then cooled to RT. It was then filtered through celite, washed with EtOAc (600 mL) and concentrated in vacuo. EtOAc (500 mL) was added to the crude product followed by water (600 mL). The two layers were separated and the aqueous layer was extracted with EtOAc (2×500 mL). The combined organic extracts were dried over MgSO$_4$ and concentrated. The crude product was purified by silica gel chromatography (10% to 50% EtOAc in hexanes) to afford the title compound as a clear oil. It exists as a mixture of geometric isomers (67.76 g, 100%). $^1$H-NMR (400 MHz, CDCl$_3$) δ ppm 3.91-4.06 (m, 1H) 4.16-4.19 (m, 1H) 4.29 (d, J=5.56 Hz, 1H) 4.78 (d, J=0.76 Hz, 2H) 5.24-5.43 (m, 2H)

5.57-5.77 (m, 1H) 7.06-7.14 (m, 1H) 7.15-7.24 (m, 1H) 7.35-7.41 (m, 1H) 7.47 (td, J=7.45, 1.77 Hz, 1H) 9.24 (br. s, 1H).

2-(7) Synthesis of (3aR,4S,6aS)-4-(fluoromethyl)-6a-(2-fluorophenyl)hexahydrofuro[3,4-c]isoxazole (S)-2-((1-fluorobut-3-en-2-yl)oxy)-1-(2-fluorophenyl)ethanone oxime (67.5 g, 279.81 mmol) was dissolved in xylenes (560 mL) and hydroquinone (5.54 g, 50.36 mmol) was added. The reaction mixture was heated to reflux (heating block temperature 145° C.) for 5 hrs. The reaction was cooled to RT and the solvent was evaporated. The residue was purified by column chromatography on amino silica (30% EtOAc in hexanes) to obtain the title compound as a yellow oil (50.53 g, 75%). $^1$H NMR (400 MHz, CDCl$_3$) δ ppm 3.32-3.42 (m, 1H) 3.96 (dd, J=10.11, 1.52 Hz, 2H) 4.16-4.43 (m, 2H) 4.44-4.83 (m, 2H) 5.38 (s, 1H) 7.09 (dd, J=11.75, 8.72 Hz, 1H) 7.18 (td, J=7.58, 1.26 Hz, 1H) 7.28-7.34 (m, 1H) 7.71 (br. s., 1H).

2-(8) Synthesis of ((2S,3R,4S)-4-amino-2-(fluoromethyl)-4-(2-fluorophenyl)tetrahydrofuran-3-yl)methanol (3aR,4S,6aS)-4-(fluoromethyl)-6a-(2-fluorophenyl)hexahydrofuro[3,4-c]isoxazole (62.20 g, 257.14 mmol) was dissolved in acetic acid (540 mL) and the solution was cooled to 0° C. Zinc dust (168.14 g, 2571.4 mmol) was added over 15 mins. The reaction temperature rose from 8° C. to 16° C. The ice bath was removed after addition and the reaction mixture was allowed to warm up to RT. Internal temperature increased to 40° C. and gradually went down to 24° C. The reaction was stirred at RT for 16 h. The reaction mixture was filtered through celite, and washed with 1.5 L of EtOAc. The solvent was evaporated and the crude product was dissolved in chloroform (600 mL), and ammonia (28% aq., 240 mL) was added slowly using a dropping funnel. Internal temperature rose to 40° C. The layers were separated, and the aqueous layer was further extracted with chloroform (3×250 mL). The combined organic extracts were dried over anhydrous MgSO$_4$ and evaporated to afford the title compound (63.00 g, 100%) which was used in the subsequent step without further purification. $^1$H-NMR (400 MHz, CDCl$_3$) δ ppm 2.39-2.86 (m, 4H) 3.81 (dd, J=11.87, 4.55 Hz, 1H) 3.94 (dd, J=9.09, 3.03 Hz, 1H) 4.07 (dd, J=12.13, 4.04 Hz, 1H) 4.25 (d, J=9.09 Hz, 1H) 4.40-4.68 (m, 3H) 7.09 (ddd, J=12.57, 8.15, 1.26 Hz, 1H) 7.17 (td, J=7.58, 1.26 Hz, 1H) 7.28-7.34 (m, 1H) 7.49 (td, J=8.08, 1.77 Hz, 1H)

2-(9) Synthesis of N-(((3S,4R,5S)-5-(fluoromethyl)-3-(2-fluorophenyl)-4-(hydroxymethyl)tetrahydrofuran-3-yl)carbamothioyl)benzamide ((2S,3R,4S)-4-amino-2-(fluoromethyl)-4-(2-fluorophenyl)tetrahydrofuran-3-yl)methanol (62.72 g, 257.84 mmol) was dissolved in anhydrous dichloromethane (500 mL). The solution was cooled to 0° C. Benzoyl isothiocyanate (38.16 mL, 283.62 mmol) was added as a solution in DCM (40 mL) over 30 mins. The internal temperature increases from 5° C. to 7° C. The mixture was allowed to warm up to RT and stirred at RT for 55 mins. The solvent was removed to give an orange foam. The residue was triturated with a 1:9 MeOH:EtOAc (500 mL) solution and the solid was filtered to give the first crop (10.50 g). The solvent was removed and the residue was triturated with a 9:1 MeOH:EtOAc (300 mL) solution to give the crop 2 (55.80 g). The mother liquor was evaporated and the residue was triturated with 9:1 MeOH:EtOAc (100 mL) to give crop 3 (4.32 g). Two more triturations provided crop 4 (3.88 g) and crop 5 (4.10 g). Finally the residue was purified by column chromatography on amino silica 70%-80% EtOAc in hexane to give 0.35 g of the product. Overall 78.95 g of the title compound as a white solid, 75% yield. $^1$H-NMR (400 MHz, CDCl$_3$) δ ppm 3.03 (br. s., 1H) 3.10 (td, J=8.21, 4.29 Hz, 1H) 3.92-4.26 (m, 3H) 4.42-4.74 (m, 4H) 7.04 (ddd, J=12.25, 8.21, 1.26 Hz, 1H) 7.19 (td, J=7.71, 1.26 Hz, 1H) 7.28-7.36 (m, 1H) 7.50-7.58 (m, 2H) 7.62-7.68 (m, 1H) 7.73 (td, J=8.02, 1.64 Hz, 1H) 7.87 (dd, J=8.46, 1.14 Hz, 2H) 8.89 (s, 1H) 11.82 (s, 1H)

2-(10) Synthesis of N-((4aS,5S,7aS)-5-(fluoromethyl)-7a-(2-fluorophenyl)-4a,5,7,7a-tetrahydro-4H-furo[3,4-d][1,3]thiazin-2-yl)benzamide N-(((3S,4R,5S)-5-(fluoromethyl)-3-(2-fluorophenyl)-4-(hydroxymethyl)tetrahydrofuran-3-yl)carbamothioyl)benzamide (78.70 g, 193.63 mmol) was dissolved in pyridine (391 mL, 5190.48 mmol), and the mixture cooled to 0° C. Trifluoromethanesulfonic anhydride (43.98 mL, 261.40 mmol) was added dropwise over 40 min (internal temperature increased from 4° C. to 18° C.). The reaction was stirred in an ice bath for 1 h and 25 mins. It was quenched by the slow addition of ammonium chloride (sat., aq., 260 mL) and then water (390 mL). The aqueous layer was extracted with EtOAc (3×500 mL). The combined organic extracts were dried over MgSO$_4$, concentrated in vacuo and purified by silica gel column chromatography (20% to 60% EtOAc/hex) to obtain the title compound (70.86 g, 94%). $^1$H NMR (400 MHz, CDCl$_3$) δ ppm 2.83 (dd, J=13.64, 3.79 Hz, 1H) 3.30 (dd, J=13.89, 3.54 Hz, 1H) 3.38-3.47 (m, 1H) 4.07 (dd, J=9.22, 2.65 Hz, 1H) 4.51-4.78 (m, 4H) 7.15 (ddd, J=12.44, 8.15, 1.14 Hz, 1H) 7.22 (td, J=7.58, 1.26 Hz, 1H) 7.34-7.41 (m, 1H) 7.41-7.48 (m, 3H) 7.49-7.56 (m, 1H) 8.10-8.18 (m, 2H).

2-(11) Synthesis of (4aS,5S,7aS)-5-(fluoromethyl)-7a-(2-fluorophenyl)-4a,5,7,7a-tetrahydro-4H-furo[3,4-d][1,3]thiazin-2-amine N-((4aS,5S,7aS)-5-(fluoromethyl)-7a-(2-fluorophenyl)-4a,5,7,7a-tetrahydro-4H-furo[3,4-d][1,3]thiazin-2-yl)benzamide (70.56 g, 181.65 mmol) was dissolved in methanol (420 mL), 1,8-diazabicyclo[5.4.0]undec-7-ene (55.73 mL, 372.69) was added, and the solution was heated to reflux (heating block temperature 80° C.) for 5 h. The reaction mixture was concentrated under reduced pressure, and the residue purified by silica gel column chromatography (10% to 50% EtOAc in hexanes) to afford the title compound (46.05 g, 89%). $^1$H NMR (400 MHz, CDCl$_3$) δ ppm 2.79 (dd, J=13.39, 4.04 Hz, 1H) 2.98-3.05 (m, 1H) 3.12 (dd, J=13.39, 3.54 Hz, 1H) 3.87 (dd, J=8.46, 2.65 Hz, 1H) 4.46 (br. s., 2H) 4.48-4.67 (m, 4H) 7.06 (ddd, J=12.57, 8.15, 1.26 Hz, 1H) 7.15 (td, J=7.58, 1.26 Hz, 1H) 7.24-7.31 (m, 1H) 7.44 (td, J=8.08, 2.02 Hz, 1H).

2-(12) Synthesis of (4aS,5S,7aS)-7a-(2-fluoro-5-nitrophenyl)-5-(fluoromethyl)-4a,5,7,7a-tetrahydro-4H-furo[3,4-d][1,3]thiazin-2-amine (4aS,5S,7aS)-5-(fluoromethyl)-7a-(2-fluorophenyl)-4a,5,7,7a-tetrahydro-4H-furo[3,4-d][1,3]thiazin-2-amine (45.85 g, 161.26 mmol) was dissolved in TFA (192 mL), and the solution was cooled to 0° C. Sulfuric acid (conc., 33.65 mL, 161.26 mmol) was added, followed by fuming nitric acid (7.78 mL, 185.44 mmol) dropwise over 25 mins. After stirring at 0° C. for 30 mins, the reaction mixture was poured onto ice (500 g)/CHCl$_3$ (500 mL) and basified to pH 12 with 6N NaOH (aq.). The two layers were separated and the aqueous layer was extracted with CHCl$_3$ (2×500 mL). The combined organic extracts were dried over MgSO4 and concentrated to give the product as a light orange foam (52.11 g, 98%). $^1$H NMR (400 MHz, CDCl$_3$) δ ppm 2.80 (dd, J=13.26, 3.92 Hz, 1H) 3.03 (dt, J=7.77, 3.82 Hz, 1H) 3.08 (dd, J=13.39, 3.28 Hz, 1H) 3.85 (dd, J=8.84, 2.27 Hz, 1H) 4.49-4.67 (m, 4H) 7.22 (dd, J=10.99, 8.97 Hz, 1H) 8.16-8.23 (m, 1H) 8.43 (dd, J=6.82, 2.78 Hz, 1H).

2-(13) Synthesis of tert-butyl ((4aS,5S,7aS)-7a-(2-fluoro-5-nitrophenyl)-5-(fluoromethyl)-4a,5,7,7a-tetrahydro-4H-furo[3,4-d][1,3]thiazin-2-yl)carbamate (4aS,5S,7aS)-7a-(2-fluoro-5-nitrophenyl)-5-(fluoromethyl)-4a,5,7,7a-tetrahydro-4H-furo[3,4-d][1,3]thiazin-2-amine (52.0 g, 157.90 mmol) was dissolved in THF (440 mL) at RT under nitrogen. Triethylamine (37.41 mL, 268.43 mmol) was added dropwise via syringe at RT. The solution was cooled to 0° C. Di-tert-butyl dicarbonate (51.69 g, 236.85 mmol) in THF (50 mL) was added portionwise over 15 mins (internal temperature remained 4° C.). The reaction mixture was stirred in the ice bath for 15 mins and was allowed to warm up to RT and stirred overnight. TLC indicated that the starting material remained. The reaction was cooled to 0° C. Triethylamine (22 mL, 157.90 mmol) was added followed by di-tert-butyl dicarbonate (17.23 g, 78.95 mmol) in THF (10 mL). The reaction was allowed to warm up to RT and stirred overnight under nitrogen. The THF was evaporated until ~300 mL remained. EtOAc (1 L) was added and the resulting precipitate was filtered to give 25.34 g of product as a white solid. THF (100 mL) and saturated aqueous NH$_4$Cl (0.5 L) were added to the filtrate. The two layers were separated and the aqueous layer was extracted with EtOAc (2×250 mL). The combined organic extracts were dried over MgSO$_4$ and concentrated. EtOAc (500 mL) was added to the residue and the precipitate was filtered to give the product as a white solid (36.16 g). Overall 61.50 g were obtained, 90.7% yield. $^1$H NMR (400 MHz, CDCl$_3$) δ ppm 1.53 (s, 9H) 2.73 (dd, J=13.64, 4.04 Hz, 1H) 2.98 (d, J=13.14 Hz, 1H) 3.18 (br. s., 1H) 3.84 (d, J=8.08 Hz, 1H) 4.45-4.74 (m, 4H) 7.19-7.26 (m, 1H) 7.35 (br. s., 1H) 8.16-8.26 (m, 1H) 8.27-8.36 (m, 1H)

2-(14) Synthesis of tert-butyl ((4aS,5S,7aS)-7a-(5-amino-2-fluorophenyl)-5-(fluoromethyl)-4a,5,7,7a-tetrahydro-4H-furo[3,4-d][1,3]thiazin-2-yl)carbamate tert-butyl ((4aS,5S,7aS)-7a-(2-fluoro-5-nitrophenyl)-5-(fluoromethyl)-4a,5,7,7a-tetrahydro-4H-furo[3,4-d][1,3]thiazin-2-yl)carbamate (67.99 g, 158.32 mmol) was dissolved in ethanol (500 mL). Tin chloride dihydrate (125.03 g, 554.13 mmol) was added in portions over 20 mins at RT. The internal temperature of the reaction went form 18° C. to 12° C. upon the addition of tin chloride. The resulting yellow suspension was stirred at RT. After stirring at RT for 40 mins the suspension turned into a clear solution and the internal temperature rose to 40° C. Eventually after 20 minutes of stirring the internal temperature went down to 23° C. The reaction was stirred at RT overnight (16 hours). The reaction mixture was poured slowly over 20 minutes onto a cooled solution of NaOH (2N aq., 1 L) and Celite® (~110 g) at 0° C. The resulting mixture was filtered through more Celite® and extracted with EtOAc (2 L). The two layers were separated. The combined organic extracts were washed with water (500 mL) and brine (500 mL), dried over MgSO$_4$ and evaporated to afford the title compound as a yellow solid (59.28 g, 94%). $^1$H NMR (400 MHz, CDCl$_3$) δ ppm 1.51 (s, 9H) 2.70 (dd, J=13.71, 3.60 Hz, 1H) 3.11 (d, J=12.51 Hz, 1H) 3.21 (br. s., 1H) 3.64 (br. s., 2H) 3.87 (d, J=7.45 Hz, 1H) 4.48-4.69 (m, 4H) 6.54-6.66 (m, 2H) 6.87 (dd, J=11.94, 8.53 Hz, 1H)

2-(15) Synthesis of tert-butyl ((4aS,5S,7aS)-7a-(2-fluoro-5-(5-methoxypyrazine-2-carboxamido)phenyl)-5-(fluoromethyl)-4a,5,7,7a-tetrahydro-4H-furo[3,4-d][1,3]thiazin-2-yl)carbamate To a stirred solution of tert-butyl ((4aS,5S,7aS)-7a-(5-amino-2-fluorophenyl)-5-(fluoromethyl)-4a,5,7,7a-tetrahydro-4H-furo[3,4-d][1,3]thiazin-2-yl)carbamate (4.70 g) and 5-methoxypyrazine-2-carboxylic acid (2.65 g), in DCM (60 mL) was added N,N-diisopropylethylamine (8.0 mL) and (1H-benzotriazol-1-yloxy)tripyrrolidin-1-yl)phosphonium hexafluorophosphate (9.0 g, portionwise over 10 min). The reaction mixture was stirred at RT for 18 h, concentrated under vacuum to circa 20 mL, and sodium bicarbonate (sat., aq., 100 mL) was added. The mixture was extracted with EtOAc (2×150 mL), the combined organic portions were dried over MgSO$_4$, evaporated and purified by silica gel chromatography (0% to 50% EtOAc in DCM gradient) to afford the title compound (6.71 g, approx. purity 90%) as a white solid. $^1$H NMR (400 MHz, CDCl$_3$) δ ppm 1.54 (m, 9H), 2.71-2.83 (br. s., 1H), 3.03-3.34 (br. s., 1H), 3.81-4.01 (br. s., 1H), 4.09 (m, 3H), 4.48-4.75 (m, 4H), 7.05-7.20 (m, 1H), 7.36-7.58 (m, 1H), 7.93-8.02 (m, 1H), 8.20 (d, J=1.3 Hz, 1H), 9.04 (d, J=1.3 Hz, 1H), 9.53 (br. s., 1H)

2-(16) Synthesis of N-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-5-methoxypyrazine-2-carboxamide tert-butyl ((4aS,5S,7aS)-7a-(2-fluoro-5-(5-methoxypyrazine-2-carboxamido)phenyl)-5-(fluoromethyl)-4a,5,7,7a-tetrahydro-4H-furo[3,4-d][1,3]thiazin-2-yl)carbamate, synthesized in preparation example 2-(2), (6.71 g, approx. purity 90%) was dissolved in DCM (20 mL) and TFA (10 mL) was added. After stirring at RT for 2 h, the reaction mixture was evaporated and sodium bicarbonate (sat., aq., 50 mL) was added. The mixture was extracted with EtOAc (2×100 mL), and the combined organic portions dried over MgSO$_4$, evaporated, and purified by silica gel chromatography (0% to 50% EtOAc in DCM) to afford the title compound as a white solid (3.26 g). $^1$H NMR (400 MHz, CDCl$_3$) δ ppm 2.81 (dd, J=13.4, 3.8 Hz, 1H), 3.08 (dt, J=7.7, 3.7 Hz, 1H), 3.18 (dd, J=13.4, 3.3 Hz, 1H), 3.88 (dd, J=8.6, 2.5 Hz, 1H), 4.09 (s, 3H), 4.43-4.73 (m, 6H), 7.10 (dd, J=11.9, 8.8 Hz, 1H), 7.55 (dd, J=7.1, 2.8 Hz, 1H), 7.91-8.00 (m, 1H), 8.17 (d, J=1.3 Hz, 1H), 9.04 (d, J=1.0 Hz, 1H), 9.51 (s, 1H)

EXAMPLE 3

Synthesis of N-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-5-methoxypyrazine-2-carboxamide

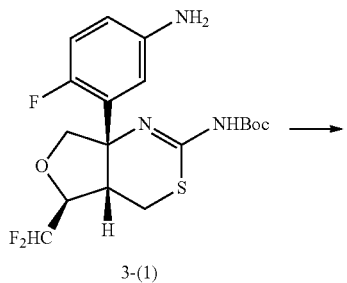

3-(1)

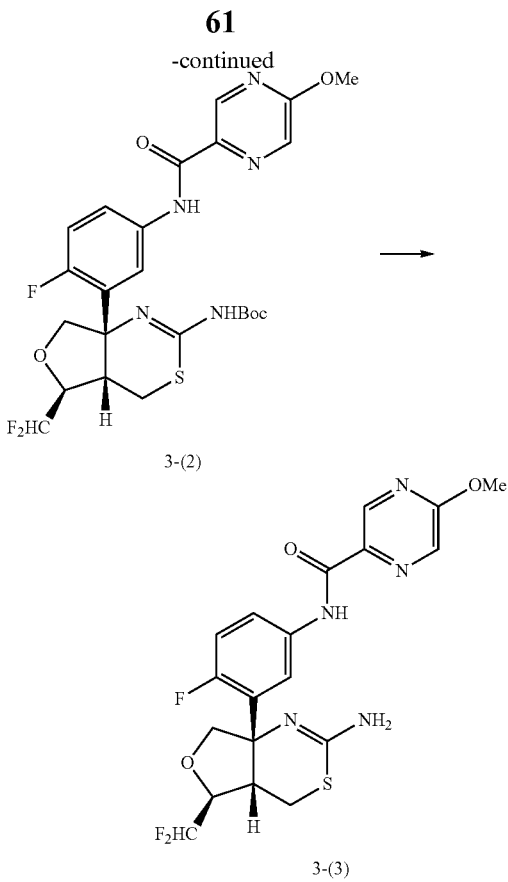

3-(2)

3-(3)

3-(2) Synthesis of tert-butyl ((4aS,5S,7aS)-5-(difluoromethyl)-7a-(2-fluoro-5-(5-methoxypyrazine-2-carboxamido)phenyl)-4a,5,7,7a-tetrahydro-4H-furo[3,4-d][1,3]thiazin-2-yl)carbamate To a stirred solution of tert-butyl ((4aS,5S,7aS)-7a-(5-amino-2-fluorophenyl)-5-(difluoromethyl)-4a,5,7,7a-tetrahydro-4H-furo[3,4-d][1,3]thiazin-2-yl)carbamate (2.70 g) and 5-methoxypyrazine-2-carboxylic acid (1.25 g, described in WO2009/091016), in DCM (30 mL) was added N,N-diisopropylethylamine (3.5 mL) and (1H-benzotriazol-1-yloxy)tripyrrolidin-1-yl)phosphonium hexafluorophosphate (4.2 g). The reaction mixture was stirred at RT for 18 h, concentrated under vacuum to circa 20 mL, and sodium bicarbonate (sat., aq., 100 mL) was added. The mixture was extracted with EtOAc (2×150 mL), the combined organic portions were dried over MgSO₄, evaporated and purified by silica gel chromatography (0% to 25% EtOAc in DCM gradient) to afford the title compound (1.74 g) as a white solid. NMR (400 MHz, CDCl₃) δ ppm 1.54 (s, 9H), 2.76-2.88 (m, 1H), 2.95-3.28 (m, 1H), 3.34-3.53 (m, 1H), 3.83-3.93 (m, 1H), 4.10 (s, 3H), 4.46-4.68 (m, 2H), 5.98 (dt, J=3.6, 56.8 Hz, 1H), 7.07-7.20 (m, 1H), 7.36-7.48 (m, 1H), 7.96-8.04 (d, J=7.8 Hz, 1H), 8.20 (d, J=1.0 Hz, 1H), 9.04 (d, J=1.3 Hz, 1H), 9.53 (br. s., 1H)

3-(3) Synthesis of N-(3-(4aS,5S,7aS)-2-amino-5-(difluoromethyl)-4a,5,7,7a-tetrahydro-4H-furo[3,4-d][1,3]thiazin-7a-yl)-4-fluorophenyl)-5-methoxypyrazine-2-carboxamide tert-butyl ((4aS,5S,7aS)-5-(difluoromethyl)-7a-(2-fluoro-5-(5-methoxypyrazine-2-carboxamido)phenyl)-4a,5,7,7a-tetrahydro-4H-furo[3,4-d][1,3]thiazin-2-yl)carbamate, synthesized in preparation example 3-(2), (1.74 g) was dissolved in DCM (20 mL) and TFA (10 mL) was added. After stirring at RT for 2 h, the reaction mixture was evaporated and sodium bicarbonate (sat., aq., 50 mL) was added. The mixture was extracted with EtOAc (2×100 mL), and the combined organic portions dried over MgSO₄ and evaporated to afford the title compound as a white solid (1.33 g). ¹H NMR (400 MHz, CDCl₃) δ ppm 2.89 (dd, J=13.6, 3.8 Hz, 1H), 3.18 (dd, J=13.3, 2.9 Hz, 1H), 3.29-3.37 (m, 1H), 3.90 (d, J=7.3 Hz, 1H), 4.09 (s, 3H), 4.41-4.70 (m, 4H), 5.96 (dt, J=4.5, 56.1 Hz, 1H), 7.12 (dd, J=11.9, 8.8 Hz, 1H), 7.50-7.62 (m, 1H), 7.97 (dt, J=8.7, 3.3 Hz, 1H), 8.17 (d, J=1.3 Hz, 1H), 9.04 (d, J=1.0 Hz, 1H), 9.52 (s, 1H)

EXAMPLE 4

N-(3-((4aS,5S,7aS)-2-amino-5-(fluoromethyl)-4a,5,7,7a-tetrahydro-4H-furo[3,4-d][1,3]thiazin-7a-yl)-4,5-difluorophenyl)-5-methoxypyrazine-2-carboxamide

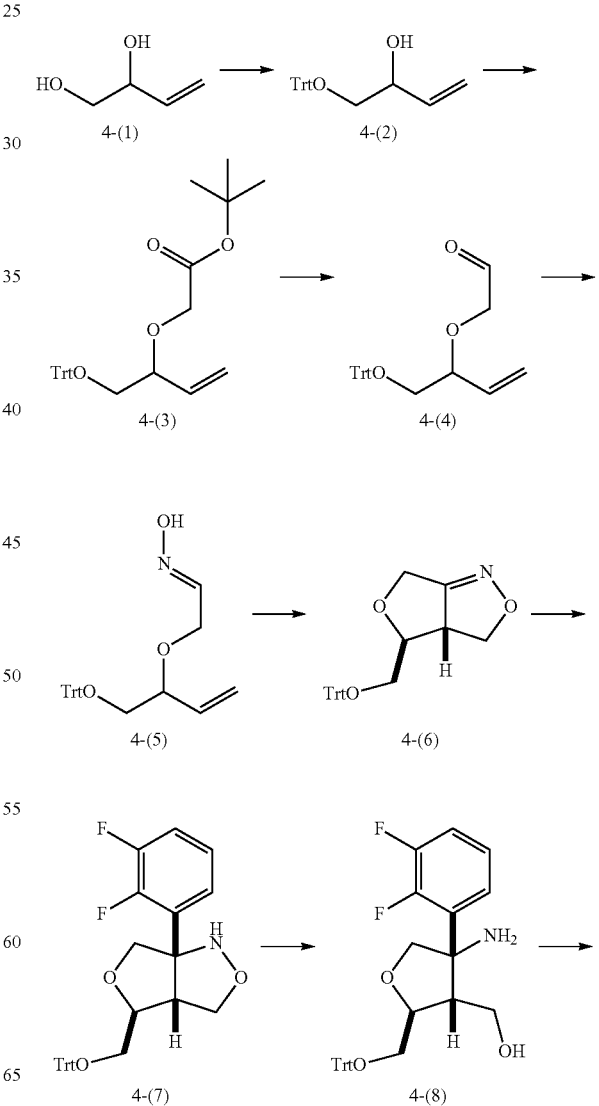

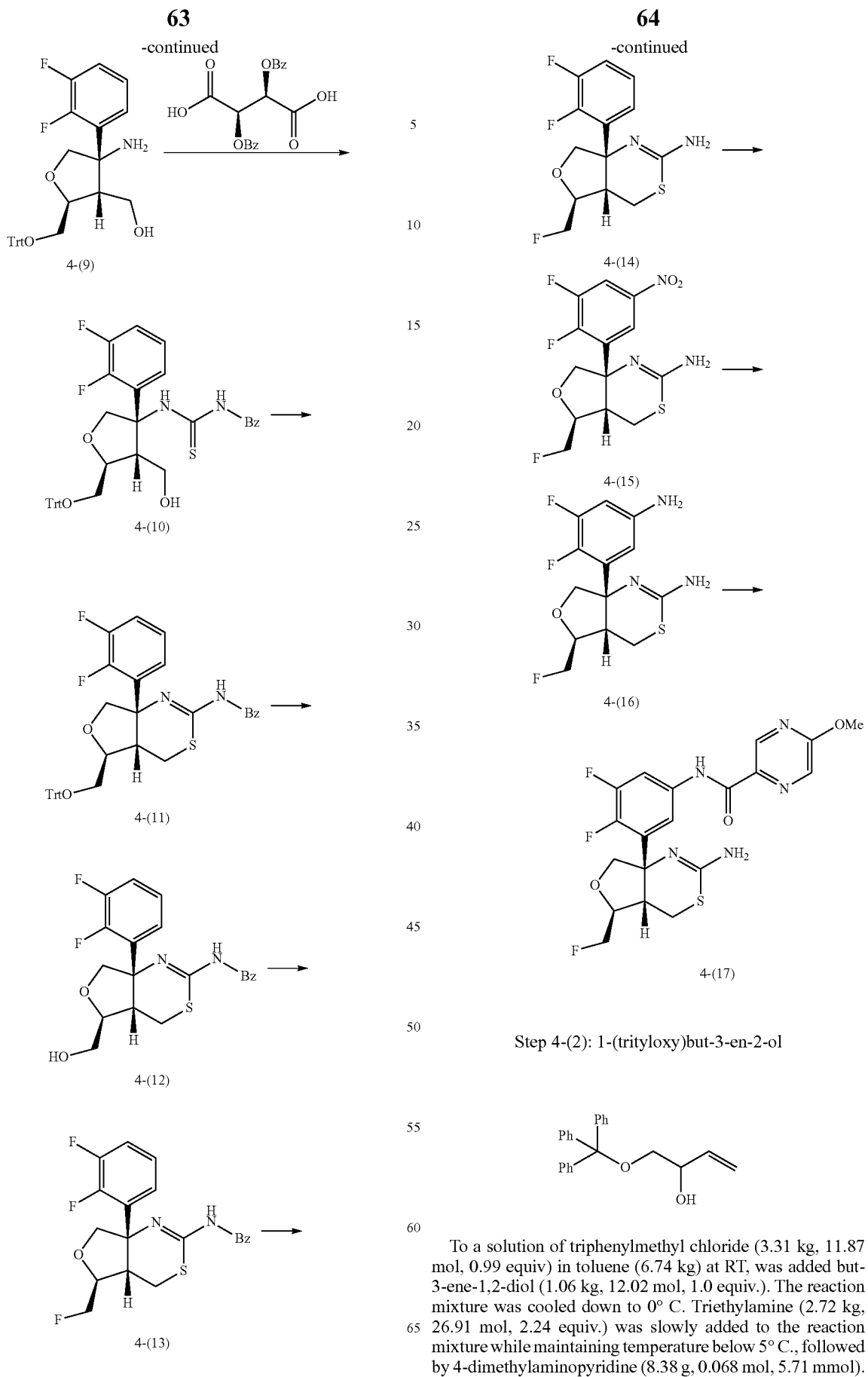
Step 4-(2): 1-(trityloxy)but-3-en-2-ol
To a solution of triphenylmethyl chloride (3.31 kg, 11.87 mol, 0.99 equiv) in toluene (6.74 kg) at RT, was added but-3-ene-1,2-diol (1.06 kg, 12.02 mol, 1.0 equiv.). The reaction mixture was cooled down to 0° C. Triethylamine (2.72 kg, 26.91 mol, 2.24 equiv.) was slowly added to the reaction mixture while maintaining temperature below 5° C., followed by 4-dimethylaminopyridine (8.38 g, 0.068 mol, 5.71 mmol).

The reaction mixture was allowed to warm up to 10° C. then heated to 40° C. The reaction mixture was stirred at 40° C. overnight. The reaction was followed by TLC (Rf 0.45 in Heptane/EtOAc 20%). The reaction mixture was cooled down to 26.5° C., filtered and the solids were rinsed with toluene (2.72 kg). The filtrate was successively washed with 28% aq. $NH_4Cl$ solution (3.38 kg) and saturated aq NaCl solution (1.26 kg). The organic phase was then concentrated under reduced pressure to afford an oil as a crude mixture 3.95 kg). $^1$H NMR (500 MHz, DMSO) δ ppm 7.42 (dd, J=8.3, 1.0 Hz, 6H), 7.33 (dd, J=10.5, 4.8 Hz, 6H), 7.30-7.19 (m, 3H), 5.94-5.83 (m, 1H), 5.25 (td, J=17.3, 1.8 Hz, 1H), 5.08 (td, J=10.9, 1.8 Hz, 1H), 2.99 (dd, J=8.9, 6.3 Hz, 1H), 2.84 (dd, J=8.9, 5.7 Hz, 1H); $^{13}$C NMR (125 MHz, DMSO) δ 144.35, 140.07, 128.78, 128.26, 127.39, 115.04, 86.25, 70.88, 68.27.

HRMS Calculated for $C_{23}H_{22}O_2$ [M+Na]$^+$ 353.1517. found 353.1543.

4-(3): tert-butyl 2-((1-(trityloxy)but-3-en-2-yl)oxy) acetate

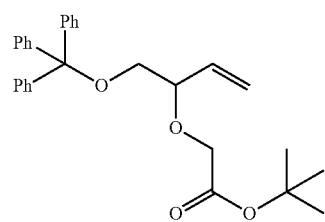 [SMILES: C=CC(COC(c1ccccc1)(c1ccccc1)c1ccccc1)OCC(=O)OC(C)(C)C]

A suspension of tetrabutylammonium hydrogen sulfate (367 g, 1.08 mol, 0.1 equiv.) in toluene (4.63 kg) under nitrogen atmosphere was prepared and cooled down to 0° C. 50% aq. NaOH solution (9.09 kg) was slowly added with the temperature kept under 50° C. Crude mixture from Step 4-(2) (3.95 kg of 1-(trityloxy)but-3-en-2-ol in toluene, total weight 6.34 kg) was slowly added with temperature kept under 15° C. The reaction mixture was stirred for 15 min. tert-Butyl bromoacetate (1.01 kg, 5.19 mol, 0.43 equiv.) was added leading to the formation of a slurry. Water (1 kg) was added then tert-butyl bromoacetate (1.55 kg, 7.95 mol, 0.66 equiv) while maintaining temperature below 30° C. The reaction was left to stir overnight. The reaction was followed by TLC (Rf 0.60 in Heptane/EtOAc 20%). Water (9.72 kg) and 2-methoxy-2-methylpropane (10.4 kg) were added then the reaction mixture was successively washed with water (3.90 kg) and with saturated aq NaCl solution (0.63 kg). The organic phase was then concentrated under reduced pressure to generate a crude mixture (4.70 kg). $^1$H NMR (500 MHz, CDCl$_3$) δ ppm 7.47 (dt, J=7.9, 3.9 Hz, 6H), 7.27-7.19 (m, 6H), 7.14 (dd, J=14.2, 6.9 Hz, 3H), 5.81-5.70 (m, 1H), 5.28 (d, J=17.2 Hz, 1H), 5.21 (d, J=9.9 Hz, 1H), 4.10-3.94 (m, 3H), 3.34 (dt, J=17.7, 8.8 Hz, 1H), 3.18 (dd, J=9.6, 5.3 Hz, 1H), 1.43 (s, 9H); $^{13}$C NMR (125 MHz, CDCl$_3$) δ 169.48, 143.95, 135.69, 128.69, 127.67, 126.86, 118.47, 86.62, 81.07, 80.74, 66.75, 66.41, 28.05.

HRMS Calculated for $C_{29}H_{22}O_4$ [M+Na]$^+$ 467.2193. found 467.2198.

4-(4): 2-((1-(trityloxy)but-3-en-2-yl)oxy)acetaldehyde

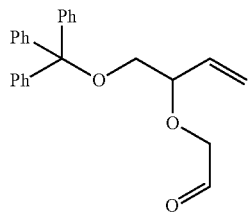 [SMILES: C=CC(COC(c1ccccc1)(c1ccccc1)c1ccccc1)OCC=O]

Crude mixture from Step 4-(3) (tert-butyl 2-((1-(trityloxy)but-3-en-2-yl)oxy)acetate 3.01 kg, 6.771 mol, 1.00 equiv.) was dissolved in $CH_2Cl_2$ (5.81 L). The reaction mixture was cooled down to −78° C. DIBAL (1.5 M in toluene, 4.14 L, 6.19 mol, 1.00 equiv.) was added in portions while maintaining temperature below −65° C. The reaction was stirred at −78° C. for additional 30 min. Aq. HCl (4.00 L, 2.0 M) was added slowly to the reaction mixture while maintaining temperature below −60° C. The reaction was then warmed up to 16.8° C. Aq. HCl (2.0 M, 3.50 L) was added slowly to the reaction mixture. The organic phase was extracted then successively washed with aq. HCl (1M, 7.50 L) and 10% aq.NaHCO$_3$ (3.75 L). The organic phase was was taken to the next step as a crude solution (11.48 kg). $^1$H NMR (500 MHz, DMSO) δ ppm 9.62 (s, 1H), 7.43 (dd, J=8.3, 0.9 Hz, 6H), 7.32 (dd, J=13.5, 5.6 Hz, 6H), 7.25 (t, J=7.3 Hz, 3H), 5.81-5.70 (m, 1H), 5.30 (dd, J=17.3, 1.0 Hz, 1H), 5.24 (dd, J=10.4, 0.8 Hz, 1H), 4.19 (q, J=18.2 Hz, 2H), 4.05 (dd, J=11.4, 6.2 Hz, 1H), 3.16 (dd, J=9.7, 6.3 Hz, 1H), 3.05 (dd, J=9.7, 4.4 Hz, 1H); $^{13}$C NMR (125 MHz, DMSO) δ ppm 201.70, 144.14, 135.92, 128.75, 128.32, 127.48, 119.01, 86.55, 80.79, 74.60, 66.57.

4-(5): 2-((1-(trityloxy)but-3-en-2-yl)oxy)acetaldehyde oxime

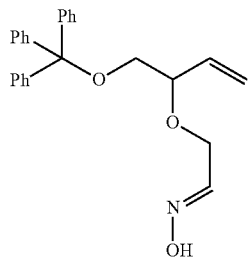 [SMILES: C=CC(COC(c1ccccc1)(c1ccccc1)c1ccccc1)OC/C=N/O]

$CH_2Cl_2$ (7.76 kg) was added to crude solution from Step 4-(4) (11.48 kg total weight). NaOAc (1.11 kg, 13.54 mol) was added and the reaction was stirred at 18.7° C. for 30 min. Hydroxylamine hydrochloride (706 g, 10.16 mol) was added and the reaction mixture was stirred at 18.9° C. for another 18 h. Water (10.1 L) was added. The biphasic mixture was stirred for 45 min. The organic phase was isolated then washed with 10% aq.NaHCO$_3$ (5.04 l). The organic phase was then concentrated under reduced pressure to produce a crude mixture (2.67 kg) as a green oil. $^1$H NMR (500 MHz, CDCl$_3$) δ ppm 7.52-7.49 (m, 0.5H), 7.48-7.43 (m, 6H), 7.29-7.21 (m, 6H), 7.20-7.13 (m, 3H), 6.96 (t, J=3.6 Hz, 0.5H), 5.73-5.64 (m, 1H), 5.24 (dd, J=17.3, 1.1 Hz, 1H), 5.18 (dd, J=10.5, 0.5 Hz, 1H), 4.43 (dd, J=16.4, 3.5 Hz, 0.51H), 4.36 (dd, J=16.4, 3.7 Hz, 0.5H), 4.17 (dd, J=12.9, 5.3 Hz, 0.5H), 4.07 (dd, J=12.9, 6.1 Hz, 0.5H), 3.93-3.81 (m, 1H), 3.32-3.25 (m, 1H), 3.15-3.08 (m, 1H); $^{13}$C NMR (125 MHz, CDCl$_3$) δ ppm 151.59, 148.71, 143.92, 135.37, 135.18, 128.67, 127.71, 126.92, 126.90, 118.43, 118.34, 86.66, 86.63, 81.09, 80.25, 66.43, 66.40, 65.63, 63.14.

Note: this compound is a mixture of isomers, which accounts for the large number of carbon peaks and the half-integer proton integrals.

HRMS Calculated for C$_{25}$H$_{25}$NO$_3$ [M+Na]$^+$ 410.1732. found 410.1748.

4-(6): (3aR*,4S*)-4-((trityloxy)methyl)-3,3a,4,6-tetrahydrofuro[3,4-c]isoxazole

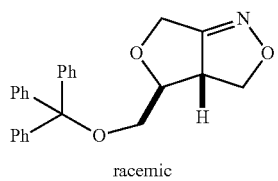

racemic

Crude mixture from Step 4-(5) (0.432 kg) was dissolved in 2-methoxy-2-methylpropane (2.16 L) then cooled to 0° C. under nitrogen atmosphere. 5% aq. NaOCl solution (4.66 kg) was added (12.5 mL/min) to the reaction mixture then the reaction was stirred at 0° C. for 3 h. The resulting white suspension was warmed up to rt and stirred overnight. The suspension was filtered and the solids rinsed with cold 2-methoxy-2-methylpropane (0.5 L). The collected solid which was dried in a vacuum oven yielding the title compound (195.1 g) as a white solid. $^1$H NMR (500 MHz, CDCl$_3$) δ ppm 7.43-7.38 (m, 6H), 7.33-7.27 (m, 6H), 7.27-7.21 (m, 3H), 4.60-4.41 (m, 3H), 4.08-3.89 (m, 3H), 3.38 (dd, J=9.8, 4.4 Hz, 1H), 3.28-3.18 (m, 1H); $^{13}$C NMR (125 MHz, CDCl$_3$) δ ppm 168.82, 143.58, 128.53, 127.93, 127.23, 86.91, 80.83, 73.00, 64.80, 61.52, 58.72

HRMS Calculated for C$_{25}$H$_{23}$NO$_3$ [M+H]$^+$ 386.1756. found 386.1786.

4-(7): (3aR*,4S*,6aS*)-6a-(2,3-difluorophenyl)-4-((trityloxy)methyl)hexahydrofuro[3,4-c]isoxazole

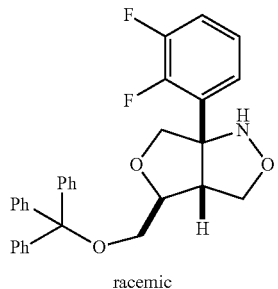

racemic

A 2.50 M solution of n-butyllithium in hexane (197 mL, 0.493 mol, 1.90 equiv.) was added dropwise to a solution containing 1-bromo-2,3-difluorobenzene (95.1 g, 0.493 mol, 1.90 equiv.) in THF/toluene (100 mL/1000 mL) under a nitrogen atmosphere at −75 to −69° C. After 10 min, boron trifluoride-diethyl etherate complex (62.5 mL, 0.493 mol) was added dropwise while maintaining temperature below −71° C. A previously prepared solution of (3aR*,4S*)-4-((trityloxy)methyl)-3,3a,4,6-tetrahydrofuro[3,4-c]isoxazole (100 g, 0.259 mol, 1.0 equiv.) in THF (400 mL) was added while maintaining the temperature below −70° C. After stirring at the −75° C. for 1.5 h, saturated aq. NH$_4$Cl (300 mL) and water (100 mL) were slowly added (over 5 min) to the reaction solution. 2-methoxy-2-methylpropane (300 mL) was added and the reaction was allowed to warm up to 0° C. The organic phase was isolated and washed with 27% aq NaCl solution (200 mL). The organic layer concentrated under reduced pressure and recrystallised from THF (200 mL)/isopropyl alcohol (700 mL). Title compound (87.5 g) was isolated. $^1$H NMR (500 MHz, DMSO) δ ppm 7.42-7.33 (m, 8H), 7.31 (t, J=7.6 Hz, 6H), 7.28-7.21 (m, 3H), 7.20-7.12 (m, 1H), 6.39 (s, 1H), 4.13 (d, J=8.2 Hz, 1H), 4.03 (s, 1H), 3.97 (s, 1H), 3.89 (d, J=9.2 Hz, 1H), 3.81-3.70 (m, 1H), 3.36-3.29 (m, 1H), 3.26 (dd, J=10.1, 6.0 Hz, 1H), 3.15 (dd, J=10.0, 3.5 Hz, 1H); $^{13}$C NMR (125 MHz, DMSO) δ ppm 150.74 (dd, J$_{CF}$=246.4, 14.4 Hz), 148.66 (dd, J$_{CF}$=248.3, 13.5 Hz), 144.09, 130.58, 128.67, 128.32, 127.48, 124.75, 124.45, 117.18 (d, J$_{CF}$=17.0 Hz), 86.57, 84.91, 78.16, 76.81, 64.82, 56.46.

HRMS Calculated for C$_{31}$H$_{27}$F$_2$NO$_3$ [M+Na]$^+$ 522.1857. found 522.1900.

4-(8): (2S*,3R*,4S*)-4-amino-4-(2,3-difluorophenyl)-2-((trityloxy)methyl)tetrahydrofuran-3-yl)methanol

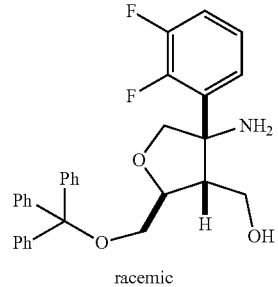 [SMILES: N[C@@]1(c2cccc(F)c2F)CO[C@H](COC(c2ccccc2)(c2ccccc2)c2ccccc2)[C@H]1CO]

racemic

To (3aR*,4S*,6aS*)-6a-(2,3-difluorophenyl)-4-((trityloxy)methyl)hexahydrofuro[3,4-c]isoxazole (87.5 g, 0.175 mol, 1.0 equiv.) was added acetic acid (385 mL). The suspension was cooled to 15° C., and zinc (88.4 g, 1.35 mol, 7.71 equiv.) was added in small portions over 2-3 min. The reaction was allowed to warm up to 18° C. over 3-4 hours and stirred for 9 h. The reaction was filtered over celite (40 g) and rinsed with toluene (210 mL). The collected filtrate was concentrated under reduced pressure with bath temperature below 35° C. and chased with three portions of toluene (3×130 mL). The resulting oil was dissolved in CH$_2$Cl$_2$ (320 mL). Water (195 mL) was added followed by 28% NH$_4$OH (43.4 mL). The organic layer was separated and the remaining aqueous phase was extracted with CH2Cl$_2$ (130 mL). The combined organic phases were washed with 27% aq. NaCl (87.5 mL). The solution was concentrated under reduced pressure, dissolved in THF (270 mL) and filtered through celite. The solids were rinsed with THF (130 mL) and the combined filtrate was concentrated under vacuum to produce title compound (69.1 g) as a foam. $^1$H NMR (500 MHz, DMSO) δ ppm 7.47 (t, J=7.5 Hz, 1H), 7.41 (d, J=7.5 Hz, 6H), 7.34-7.27 (m, 7H), 7.28-7.21 (m, 3H), 7.19-7.10 (m, 1H), 4.14 (d, J=8.7 Hz, 1H), 4.15-4.09 (m, 1H), 3.77 (dd, J=8.6, 2.6 Hz, 1H), 3.59 (dd, J=11.1, 6.4 Hz, 1H), 3.46 (dd, J=11.1, 6.6 Hz, 1H), 3.18 (dd, J=9.9, 3.0 Hz, 1H), 3.07 (dd, J=9.9, 5.8 Hz, 1H), 2.62 (dd, J=14.6, 6.6 Hz, 1H); $^{13}$C NMR (125 MHz, DMSO) δ ppm 150.68 (dd, $J_{CF}$=244.4, 13.9 Hz), 148.46 (dd, $J_{CF}$=246.7, 13.0 Hz), 144.36, 135.44 (d, $J_{CF}$=8.1 Hz), 128.76, 128.23, 127.37, 124.31, 124.23, 116.12 (d, $J_{CF}$=17.1 Hz), 86.29, 81.48, 78.92 (d, $J_{CF}$=4.3 Hz), 66.03, 63.93, 59.49, 51.27

HRMS Calculated for $C_{31}H_{29}F_2NO_3$ [M+Na]$^+$ 524.2013. found 524.2039.

4-(9): ((2S,3R,4S)-4-amino-4-(2,3-difluorophenyl)-2-((trityloxy)methyl)tetrahydrofuran-3-yl)methanol (−)dibenzoyl-L-tartaric acid

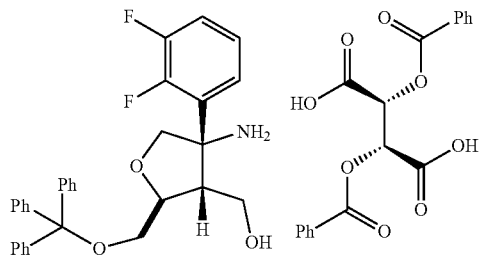

Chiral Resolution

Racemic mixture (2S*,3R*,4S*)-6a-(2,3-difluorophenyl)-4-((trityloxy)methyl)hexahydrofuro[3,4-c]isoxazole (69.1 g, 0.138 mol, 1.0 equiv.) and (−)-dibenzoyl-L-tartaric acid (49.4 g, 0.138 mol, 1.0 equiv) were dissolved in acetone (346 mL). The mixture was then heated to 61.9° C. over 15 min. Toluene (415 mL) was added. The solution was then allowed to cool to RT. Then the reaction mixture was cooled to −5° C. and stirred for another hour at this temperature. The suspension was filtered and washed with a solution of toluene/acetone (V/V 6/5, 138 mL, cooled to 0° C.). The solid was dried under reduced pressure, and the title compound (44.5 g,) was isolated. $^1$H NMR (500 MHz, DMSO) δ ppm 8.00-7.95 (m, 4H), 7.66 (t, J=7.4 Hz, 2H), 7.53 (t, J=7.8 Hz, 4H), 7.47-7.39 (m, 2H), 7.40-7.35 (m, 6H), 7.35-7.28 (m, 6H), 7.28-7.23 (m, 3H), 7.23-7.15 (m, 1H), 5.75 (s, 1H), 4.19 (d, J=9.5 Hz, 2H), 4.02 (dd, J=9.5, 2.1 Hz, 1H), 3.61 (dd, J=11.4, 6.4 Hz, 1H), 3.52 (dd, J=11.4, 6.2 Hz, 1H), 3.21-3.14 (m, 1H), 3.12-3.05 (m, 1H), 2.77 (dd, J=14.3, 6.4 Hz, 1H); $^{13}$C NMR (125 MHz, DMSO) δ ppm 168.07, 165.23, 150.68 (dd, $J_{CF}$=245.2, 13.4 Hz), 148.27 (dd, $J_{CF}$=248.0, 13.6 Hz), 144.18, 134.09, 129.75, 129.60, 129.24, 128.70, 128.28, 127.45, 124.88, 124.20, 117.40 (d, $J_{CF}$=16.8 Hz), 86.40, 80.73, 76.73, 72.22, 65.42, 64.58, 58.63, 50.51.

HRMS Calculated for $C_{31}H_{29}F_2NO_3$ [M+Na]$^+$ 524.2013. found 524.2047.

Chiral HPLC Parameters:
Equipment, Reagents, and Mobile Phase:
Equipment:

| | |
|---|---|
| HPLC column: | Chiralpak AD, 4.6 × 250 mm, 10 µm, Daicel Chemical Industries, Ltd., catalog no. 19025. |
| Solvent Delivery System: | Agilent 1100 HPLC ternary pump, low pressure mixing with an in-line degasser, or equivalent. |
| Autosampler: | Agilent 1100 autosampler, 0.1 to 100 µL range, or equivalent. |
| Detector: | Agilent 1100 variable wavelength detector or equivalent. |
| Chromatographic Software: | Agilent ChemStation software version A.09.03 or higher for HPLC, Waters Empower 2 Build 2154 or equivalent. |
| Volumetric Glassware: | Class A. |
| Volumetric pipette: | Class A. |
| Pipettor: | Calibrated Eppendorf adjustable volume, or equivalent. |
| Balance: | Analytical balance, capable of weighing ±0.1 mg. |

Reagents:

| | |
|---|---|
| Heptane: | HPLC grade, Baker (catalog no. 9177-03) or equivalent. |
| 2-Propanol: | HPLC grade, Baker (catalog no. 9095-03) or equivalent. |
| Triethylamine: | ≥99%, Sigma-Aldrich (catalog no. T0886) or equivalent. |

Mobile Phase:

Add 100 mL 2-propanol and 900 mL heptane (measured separately with a 100 mL and 1000-mL graduated cylinders) and 0.5 mL triethylamine (measured with volumetric glass pipette) to an appropriate flask and mix. Degas in-line during use.

Diluting Solution: 2-Propanol

HPLC Parameters:

| | |
|---|---|
| HPLC column: | Chiralpak AD, 4.6 × 250 mm, 10 µm, Daicel Chemical Industries, Ltd., catalog no. 19025. |
| Temperature: | 35° C. |
| Flow rate*: | 0.8 mL/min |
| Gradient: | NA |
| Injection volume: | 5 µL |
| Detection: | 260 nm UV |
| Data acquisition time: | 40 min |
| Total run time: | 40 min |
| Column Maximum Pressure: | 35 Bar |
| Needle Wash: | 2-propanol |

*Flow rate may be adjusted ±0.2 ml/min to obtain specified retention times.

Retention Times for Analytes and Impurities:

| Compound Peak | Retention Time (Relative Retention Time, RRT) |
|---|---|
| (structure shown) | 15.5 min ± 10% (RRT 1.00) |

| Compound Peak | Retention Time (Relative Retention Time, RRT) |
|---|---|
| 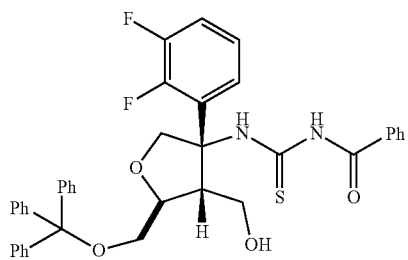 [SMILES: O=C(NC(=S)N[C@@]1(c2cccc(F)c2F)CO[C@H](COC(c2ccccc2)(c2ccccc2)c2ccccc2)[C@H]1CO)c1ccccc1] (Enantiomer) | 21.5 min (RRT 1.39) |

A Typical Chromatogram from a Chiral HPLC Isolation of Compound 4-(9) is presented in FIG. 1.

4-(10): N-(((3S,4R,5S)-3-(2,3-difluorophenyl)-4-(hydroxymethyl)-5-((trityloxy)methyl)tetrahydrofuran-3-yl)carbamothioyl)benzamide

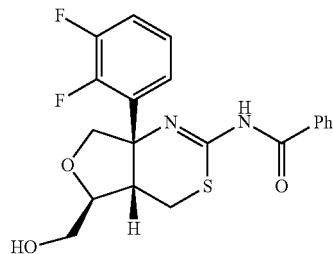 [SMILES: O=C(NC1=N[C@@]2(c3cccc(F)c3F)CO[C@H](CO)[C@H]2CS1)c1ccccc1]

A suspension of ((2S,3R,4S)-4-amino-4-(2,3-difluorophenyl)-2-((trityloxy)methyl)tetrahydrofuran-3-yl)methanol (−)dibenzoyl-L-tartaric acid (44.21 g, 0.051 mol, 1.0 equiv.) in EtOAc (133 mL) was cooled down to 1.7° C. Aq. NaOH (1.0 M, 121 mL, 0.12 mol, 2.4 equiv.) was added while maintaining temperature below 5° C. The reaction was stirred for 5 min then benzyl isothiocyanate (9.43 g, 0.058 mol, 1.12 equiv.) was added over 5 min. After 1.5 h, EtOAc (133 mL) was added. The organic phase was isolated and successively washed with saturated aq. NaHCO₃ (130 mL) and 18% aq.NaCl (44 mL). The combined aqueous phases were extracted with EtOAc (66 mL) and CH₂Cl₂ (30 mL). All the organic phase were combined, filtered and concentrated under reduced pressure. The title compound (34.2 g) was isolated as a foam after chasing the residual solvent with CH₂Cl₂ (88 mL). ¹H NMR (500 MHz, DMSO) δ ppm 11.97 (br s, 1H), 11.20 (br s, 1H), 7.94 (d, J=7.4 Hz, 2H), 7.63 (t, J=7.4 Hz, 1H), 7.51 (t, J=7.8 Hz, 2H), 7.38-7.21 (m, 17H), 7.13 (dd, J=13.4, 7.9 Hz, 1H), 5.13 (t, J=4.4 Hz, 1H), 5.07 (d, J=9.7 Hz, 1H), 4.47 (d, J=9.8 Hz, 1H), 4.24-4.16 (m, 1H), 3.68 (t, J=4.6 Hz, 2H), 3.19 (dd, J=10.1, 2.9 Hz, 1H), 3.01 (dd, J=10.1, 4.8 Hz, 1H), 2.63-2.52 (m, 1H); ¹³C NMR (125 MHz, DMSO) δ ppm 180.06, 168.14, 150.75 (dd, $J_{CF}$=244.6, 13.2 Hz), 147.93 (dd, $J_{CF}$=247.5, 13.5 Hz), 144.15, 133.46, 132.55, 131.90 (d, $J_{CF}$=6.4 Hz), 129.04, 128.86, 128.67, 128.28, 127.43, 124.41, 124.25, 116.12 (d, $J_{CF}$=17.0 Hz), 86.27, 79.75, 75.03, 68.04, 64.63, 58.16, 53.35.

HRMS Calculated for $C_{39}H_{34}F_2N_2O_4S$ [M+H]⁺ 663.2129. found 663.2200.

4-(11): N-((4aS,5S,7aS)-7a-(2,3-difluorophenyl)-5-((trityloxy)methyl)-4a,5,7,7a-tetrahydro-4H-furo[3,4-d][1,3]thiazin-2-yl)benzamide

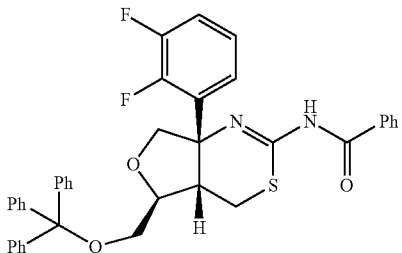 [SMILES: O=C(NC1=N[C@@]2(c3cccc(F)c3F)CO[C@H](COC(c3ccccc3)(c3ccccc3)c3ccccc3)[C@H]2CS1)c1ccccc1]

To a solution of N-(((3S,4R,5S)-3-(2,3-difluorophenyl)-4-(hydroxymethyl)-5-((trityloxy)methyl)tetrahydrofuran-3-yl)carbamothioyl)benzamide (34.0 g, 0.0511 mol, 1.0 equiv.) in CH₂Cl₂ (204 mL) at −20° C., pyridine (10.3 ml, 0.128 mol, 2.50 equiv.) was added. A solution of trifluoromethanesulfonic anhydride (9.46 mL, 0.0563 mol, 1.10 equiv.) in CH₂Cl₂ (34 mL) was then added over 12 min while maintaining temperature below −17° C. The reaction was stirred for 30 min at −20° C. then allowed to warm up slowly to 5° C. Sat aq. NH₄Cl (85 mL) and water (32 mL) were added. The aqueous layer was then extracted with CH₂Cl₂ (68 mL). The organic phase was concentrated under reduced pressure providing title compound (33.6 g) as an orange foam.

HRMS Calculated for $C_{39}H_{32}F_2N_2O_3S$ [M+H]⁺ 647.2180. found 647.2123.

4-(12): N-((4aS,5S,7aS)-7a-(2,3-difluorophenyl)-5-(hydroxymethyl)-4a,5,7,7a-tetrahydro-4H-furo[3,4-d][1,3]thiazin-2-yl)benzamide

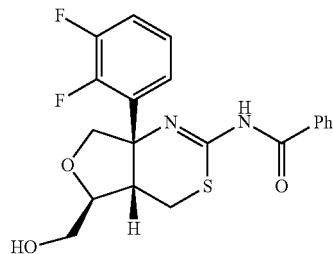 [SMILES: O=C(NC1=N[C@@]2(c3cccc(F)c3F)CO[C@H](CO)[C@H]2CS1)c1ccccc1]

Formic acid (116 mL) was added to N-((4aS,5S,7aS)-7a-(2,3-difluorophenyl)-5-((trityloxy)methyl)-4a,5,7,7a-tetrahydro-4H-furo[3,4-d][1,3]thiazin-2-yl)benzamide (33.30 g, 0.051 mol, 1.0 equiv.), the mixture was stirred at r.t for 25 min. Water (17 mL) was added dropwise then the reaction was stirred for another 30 min. The resulting suspension was filtered; the filtrate was dried by azeotropic distillation under vacuum with toluene (360 mL). Methanol (110 mL) was added followed by triethylamine (22 mL, 0.15 mol, 3.0 equiv.) and the solution was stirred for 2 h. The solvent was removed under vacuum and chased with toluene (66 mL). The residual oil was dissolved in CH₂Cl₂ (250 ml) and washed successively with aq.HCl (1M, 100 mL), sat aq.NaHCO₃ (67 mL) and 18% aq.NaCl (67 mL). The organic phase was concentrated under reduce pressure. Toluene (66 mL) and THF (67 mL) were added to the residue then the solution was filtered through celite and concentrated under reduced pressure to yield the title compound (21 g). $^1$H NMR (500 MHz, DMSO) ppm 8.11 (dd, J=16.4, 4.2 Hz, 2H), 7.70-7.58 (m, 1H), 7.57-7.44 (m, 3H), 7.43-7.34 (m, 1H), 7.34-7.26 (m, 1H), 4.43 (d, J=9.5 Hz, 1H), 4.25-4.16 (m, 1H), 4.10 (d, J=9.2 Hz, 1H), 3.59 (d, J=4.5 Hz, 2H), 3.30-3.21 (m, 1H), 3.20-3.08 (m, 2H); $^{13}$C NMR (125 MHz, DMSO) δ ppm 169.08, 150.95 (dd, $J_{CF}$=245.8, 13.1 Hz), 148.22, 148.09 (dd, $J_{CF}$=248.7, 13.2 Hz), 133.46, 129.11, 128.99, 128.62, 125.43, 124.70, 118.16 (d, $J_{CF}$=16.9 Hz), 81.36, 75.29, 66.76, 62.39, 40.77, 24.25.

HRMS Calculated for $C_{20}H_{18}F_2N_2O_3S$ [M+H]$^+$ 405.1084. found 405.1081.

4-(13): N-((4aS,5S,7aS)-7a-(2,3-difluorophenyl)-5-(fluoromethyl)-4a,5,7,7a-tetrahydro-4H-furo[3,4-d][1,3]thiazin-2-yl)benzamide

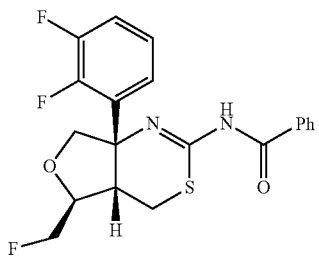 [SMILES: O=C(NC1=N[C@@]2(c3cccc(F)c3F)CO[C@H](CF)[C@H]2CS1)c1ccccc1]

N-((4aS,5S,7aS)-7a-(2,3-difluorophenyl)-5-(hydroxymethyl)-4a,5,7,7a-tetrahydro-4H-furo[3,4-d][1,3]thiazin-2-yl)benzamide (21.0 g, 0.519 mol, 1.0 equiv.) was dissolved in dry THF (105 mL) under a nitrogen atmosphere and the solution was cooled at 0° C. N,N-diisopropylethylamine (40.7 mL, 0.234 mol, 4.50 equiv.), triethylamine trihydrofluoride (14.0 mL, 0.0857 mol, 1.65 equiv.) and perfluorobutanesulfonyl fluoride (22.4 mL, 0.125 mol, 2.40 equiv.) were added while maintaining temperature under 5° C. The reaction was stirred for 3 h at 0° C. then slowly warmed to RT and stirred for 11 h. To the reaction mixture was charged sat.NH$_4$Cl (100 mL) followed by 2-methoxy-2-methylpropane (100 mL). The organic phase was isolated and washed with aq. HCl (1.0 M, 100 ml), concentrated and redissolved in 2-methoxy-2-methylpropane (301 ml). The organic phase was then washed with aq.HCl (1M, 63 mL), sat aq.NaHCO$_3$ (100 mL). The last aqueous layer was extracted with 2-methoxy-2-methylpropane. The combined organic phase was washed with 18% aq.NaCl (63 mL) and concentrated under reduced pressure to afford title compound (19.40 g) as a foam. $^1$H NMR (500 MHz, DMSO) δ ppm 8.02 (s, 2H), 7.61-7.51 (m, 1H), 7.51-7.38 (m, 3H), 7.39-7.18 (m, 2H), 4.72-4.49 (m, 2H), 4.48-4.37 (m, 1H), 4.41 (d, J=9.1 Hz, 21H), 3.04 (s, 2H); $^{13}$C NMR (125 MHz, DMSO) δ ppm 150.92 (dd, $J_{CF}$=245.5, 13.3 Hz), 148.11 (dd, $J_{CF}$=248.2, 13.4 Hz), 132.40, 128.99, 128.63, 125.16, 124.94, 117.61, 83.64 (d, $J_{CF}$=170.2 Hz), 79.51 (d, $J_{CF}$=18.4 Hz), 76.17, 66.27, 23.67.

HRMS Calculated for $C_{20}H_{17}F_3N_2O_2S$ [M+H]$^+$ 407.1041. found 407.1024.

4-(14): (4aS,5S,7aS)-7a-(2,3-difluorophenyl)-5-(fluoromethyl)-4a,5,7,7a-tetrahydro-4H-furo[3,4-d][1,3]thiazin-2-amine

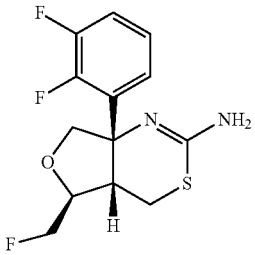

N-((4aS,5S,7aS)-7a-(2,3-difluorophenyl)-5-(fluoromethyl)-4a,5,7,7a-tetrahydro-4H-furo[3,4-d][1,3]thiazin-2-yl)benzamide (19.40 g, 0.048 mol, 1.0 equiv.) was dissolved in methanol (97 mL), under nitrogen. 1,8-diazabicyclo[5.4.0]undec-7-ene (8.92 mL, 0.060 mol, 1.25 equiv.) was added, and the solution was heated to 55-60° C. After 8 h, the reaction mixture was concentrated under reduced pressure, and the residue purified by silica gel flash column chromatography (5% to 100% EtOAc in heptane) to afford the title compound (9.01 g). $^1$H NMR (500 MHz, DMSO) δ ppm 7.38-7.28 (m, 1H), 7.26-7.14 (m, 2H), 6.12 (s, 2H), 4.66-4.41 (m, 2H), 4.37-4.27 (m, 2H), 4.29 (d, J=8.2 Hz, 1H), 3.74 (dd, J=8.2, 2.6 Hz, 1H), 3.30 (s, 1H), 3.06-2.90 (m, 2H), 2.79-2.71 (m, 1H); $^{13}$C NMR (125 MHz, DMSO) δ ppm 150.84 (dd, J=244.8, 14.0 Hz), 149.71, 148.07 (dd, $J_{CF}$=247.8, 13.4 Hz), 133.08 (d, $J_{CF}$=7.7 Hz), 125.24, 124.55 (dd, $J_{CF}$=7.2, 4.3 Hz), 116.58 (d, $J_{CF}$=17.2 Hz), 83.91 (d, $J_{CF}$=170.0 Hz), 79.12 (d, $J_{CF}$ 18.2 Hz), 77.96 (d, $J_{CF}$=4.9 Hz), 66.22, 36.41 (d, $J_{CF}$=3.3 Hz), 23.40.

HRMS Calculated for $C_{13}H_{13}F_3N_2OS$ [M+H]$^+$ 303.0779. found 303.0767.

4-(15): (4aS,5S,7aS)-7a-(2,3-difluoro-5-nitrophenyl)-5-(fluoromethyl)-4a,5,7,7a-tetrahydro-4H-furo[3,4-d][1,3]thiazin-2-amine

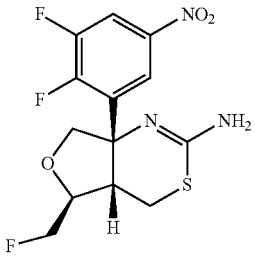 [SMILES: NC1=N[C@@]2(c3cc([N+](=O)[O-])cc(F)c3F)CO[C@H](CF)[C@H]2CS1]

(4aS,5S,7aS)-7a-(2,3-difluorophenyl)-5-(fluoromethyl)-4a,5,7,7a-tetrahydro-4H-furo[3,4-d][1,3]thiazin-2-amine (9.10 g, 0.03 mol, 1.0 equiv.) was dissolved in trifluoroacetic acid (36.4 mL), and the solution was cooled to 0° C. Sulfuric acid (conc., 12.0 mL) was added, followed by fuming nitric acid (6.9 mL) dropwise while maintaining the temperature below 5° C. After stirring at 0-5° C. for 4 h, the reaction mixture was slowly charged into a vigorously stirred solution of aq.NaOH (43.3 g in 273 mL water) while maintaining a temperature below 20° C. The mixture was extracted with CH$_2$Cl$_2$ (1×94 ml, and 2×64 mL), and the combined organic phases were washed with sat. aq. NaCl (46 mL). Celite (15.0 g) was added to the organics, and the mixture was filtered rinsing with CH$_2$Cl$_2$ (40 mL). The solvents were evaporated to afford the title compound (8.3 g) which was used in the subsequent step without purification. $^1$H NMR (500 MHz, DMSO) δ ppm 8.41-8.30 (m, 1H), 8.22-8.13 (m, 1H), 6.36 (s, 2H), 4.70-4.46 (m, 2H), 4.43-4.31 (m, 1H), 4.35 (d, J=8.7 Hz, 1H), 3.69 (dd, J=8.5, 1.6 Hz, 1H), 3.04-2.91 (m, 2H), 2.86-2.76 (m, 1H); $^{13}$C NMR (125 MHz, DMSO) δ ppm 152.36 (dd, J$_{CF}$=246.8, 12.3 Hz), 151.13, 150.32 (dd, J$_{CF}$=238.2, 12.2 Hz), 143.25 (dd, J$_{CF}$=7.9, 2.5 Hz), 134.70 (d, J$_{CF}$=9.5 Hz), 121.28, 113.02 (d, J$_{CF}$=22.3 Hz), 83.74 (d, J$_{CF}$=170.1 Hz), 79.44 (d, J$_{CF}$=18.3 Hz), 78.02 (d, J=3.9 Hz), 36.96, 23.28.

HRMS Calculated for C$_{13}$H$_{12}$F$_3$N$_3$O$_3$S [M+H]$^+$ 348.0630. found 348.0614.

4-(16): (4aS,5S,7aS)-7a-(5-amino-2,3-difluorophenyl)-5-(fluoromethyl)-4a,5,7,7a-tetrahydro-4H-furo[3,4-d][1,3]thiazin-2-amine

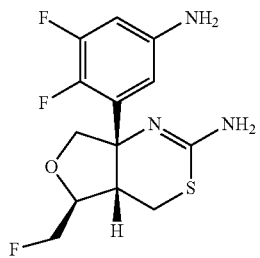 [SMILES: NC1=N[C@@]2(c3cc(N)cc(F)c3F)CO[C@H](CF)[C@H]2CS1]

To iron (8.03 g, 0.144 mol, 6.0 equiv.) was added ethanol (66.56 mL), followed by conc. HCl (62%, 1.2 mL, 0.014 mol, 0.60 equiv.). The mixture was heated to 65° C. for 2 h, and then sat NH$_4$Cl (33%, 33.3 mL) was added and the reaction temperature was maintained at 55° C. A solution of (4aS,5S,7aS)-7a-(2,3-difluoro-5-nitrophenyl)-5-(fluoromethyl)-4a,5,7,7a-tetrahydro-4H-furo[3,4-d][1,3]thiazin-2-amine (8.32 g, 0.024 mol, 1.0 equiv.) and conc. HCl (1.93 mL, 0.024 mol, 1.0 equiv.) in ethanol (41.6 mL) was added to the iron suspension. The reaction was stirred for 30 min at 55° C., then ethanol (50 mL) was added and the suspension was allowed to cool down to 20° C., filtered through celite (8.3 g) and rinsed with ethanol (125 mL). The filtrate was concentrated under reduced pressure then water (66 mL) was added, followed by 3.0 M aq.NaOH (24 mL, 0.0179 mol, 3.0 equiv.). The resulting mixture was extracted with CH$_2$Cl$_2$ (2×83 mL). The organics phases were combined and filtered over celite and concentrated under reduce pressure to give the title compound (7.60 g). $^1$H NMR (500 MHz, DMSO) δ ppm 6.42-6.35 (m, 2H), 6.02 (brs, 2H), 4.66-4.41 (m, 2H), 4.37-4.25 (m, 1H), 4.21 (d, J=8.0 Hz, 1H), 3.69 (dd, J=7.8, 2.2 Hz, 1H), 2.97 (qd, J=13.5, 3.4 Hz, 3H), 2.74-2.64 (m, 1H); $^{13}$C NMR (125 MHz, DMSO) δ ppm 151.08 (dd, J$_{CF}$=240.1, 14.8 Hz), 148.88, 145.40 (d, J$_{CF}$=10.7 Hz), 139.33 (dd, J$_{CF}$=233.5, 13.8 Hz), 132.53 (d, J$_{CF}$=8.1 Hz), 109.90, 100.70 (d, J$_{CF}$=20.0 Hz), 83.99 (d, J$_{CF}$=169.9 Hz), 78.79 (d, J$_{CF}$=18.3 Hz), 77.99 (d, J$_{CF}$=5.5 Hz), 66.22, 36.24, 23.14.

HRMS Calculated for C$_{13}$H$_{14}$F$_3$N$_3$OS [M+H]$^+$ 318.0888. found 318.0874.

4-(17): N-(3-((4aS,5S,7aS)-2-amino-5-(fluoromethyl)-4a,5,7,7a-tetrahydro-4H-furo[3,4-d][1,3]thiazin-7a-yl)-4,5-difluorophenyl)-5-methoxypyrazine-2-carboxamide

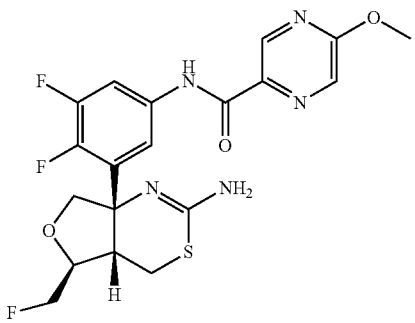 [SMILES: COc1cnc(C(=O)Nc2cc(F)c(F)c([C@]34CO[C@H](CF)[C@H]3CSC(N)=N4)c2)cn1]

A suspension of 5-methoxypyrazine-2-carboxylic acid (4.01 g, 0.026 mol, 1.10 equiv.) in N,N'-dimethylimidazoline-2-one (22.5 mL) was stirred at ambient temperature for 15 min, then cooled to 0° C. Thionyl chloride (2.24 mL, 0.031 mol, 1.3 equiv.) was added while maintaining temperature under 10° C. The resulting suspension was stirred at 0-10° C. for 2 h while it transitioned to a clear solution. In another vessel, (4aS,5S,7aS)-7a-(5-amino-2,3-difluorophenyl)-5-(fluoromethyl)-4a,5,7,7a-tetrahydro-4H-furo[3,4-d][1,3]thiazin-2-amine (7.60 g, 0.024 mol, 1.0 equiv.) was dissolved into N,N'-dimethylimidazoline-2-one (22.5 mL). The resolution solution was added to the solution of acyl chloride while maintaining temperature below 10° C. The reaction mixture was stirred for 30 min. Water (112 mL) was charged while maintaining temperature below 30° C. The resolution mixture was stirred for 30 min., and then EtOAc (112 mL) was added. To this mixture was added, 50% aq. NaOH (10.0 g) until the pH of the aqueous layer reached 11. The aq. layer was extracted with EtOAc (75 mL). The organics were combined, washed with sat. aq. NaCl (38 mL) and water (38 mL). The organics were filtered over a pad of silica gel (15 g) and rinsed with EtOAc (37.5 mL). The organics were concentrated under vacuum to afford a solid. To the solid was added 1-propanol (112 mL), and the suspension was heated to 100° C. The mixture was cooled to −10° C. and held for 1 h. The solid was filtered, rinsed with cold 1-propanol (15 mL) and dried under vacuum (35° C.) until constant weight to afford the title compound (8.18 g). $^1$H NMR (500 MHz, DMSO) δ ppm 10.73 (s, 1H), 8.88 (d, =0.8 Hz, 1H), 8.39 (d, J=0.9 Hz, 1H), 8.11-7.87 (m, 1H), 7.73 (d, J=5.0 Hz, 1H), 6.07 (s, 2H), 4.68-4.44 (m, 2H), 4.41-4.28 (m, 1H), 4.23 (d, J=8.3 Hz, 1H), 4.01 (s, 3H), 3.82 (dd, J=8.1, 2.4 Hz, 1H), 3.18 (dd, J=13.5, 3.5 Hz, 1H), 3.01 (dd, J=13.5, 3.8 Hz, 1H), 2.77-2.69 (m, 1H); $^{13}$C NMR (125 MHz, DMSO) δ ppm 162.24, 162.20, 150.05 (dd, J$_{CF}$=242.1, 14.4 Hz), 149.37, 144.42 (dd, J$_{CF}$=245.5, 13.7 Hz), 142.18, 138.09, 134.73 (dd, J$_{CF}$=10.3, 2.7 Hz), 134.03, 133.22 (d, J$_{CF}$=9.1 Hz), 116.6, 108.42 (d, J$_{CF}$=22.4 Hz), 83.98 (d, J$_{CF}$=169.9 Hz), 79.21 (d, J$_{CF}$=18.2 Hz), 77.96 (d, J$_{CF}$=5.2 Hz), 66.26, 54.78, 36.23, 23.64.

HRMS Calculated for C$_{19}$H$_{18}$F$_3$N$_5$O$_3$S [M+H]$^+$ 454.1161. found 454.1149.

Specific optical rotation [α]$_D$+115.3 (c 0.584, MeOH)

Specific Optical Rotation Parameters:

Equipment:
- Polarimeter: Perkin Elmer, model 341 or equivalent.
- Cell: Microglass cell, 100 mm pathlength, 1.0 mL capacity, Perkin-Elmer Cat. # B001-7047.
- Balance: Calibrated analytical balance capable of weighing ±0.1 mg
- Water Bath: NESLAB RTE 1121 Chiller or equivalent.
- Volumetric glassware: Class A.
- Quartz Standard ID number 098799, or equivalent.
- Polarimeter: Perkin Elmer, model 341 or equivalent.

Reagents:
- Methanol: HPLC grade, Baker (catalog no. 9093-03) or equivalent.

Instrument Parameters:
- Lamp: Na/Hal, Perkin-Elmer Cat. # B000-8754.
- Cell: Microcell (100 mm), Perkin-Elmer Cat. #B004-1693.
- Cell Path: 100 mm (1 decimeter)
- Mode: OROT
- Wavelength: 589 nm
- Cell Temperature: 20° C.
- Integration time: 2 seconds
- Aperture: MICRO
- Water bath temperature: 20±1° C.

Alternative synthesis 4-(7) of 4-(6) (3aR*,4S*, 6aS*)-6a-(2,3-difluorophenyl)-4-((trityloxy)methyl)hexahydrofuro[3,4-c]isoxazole

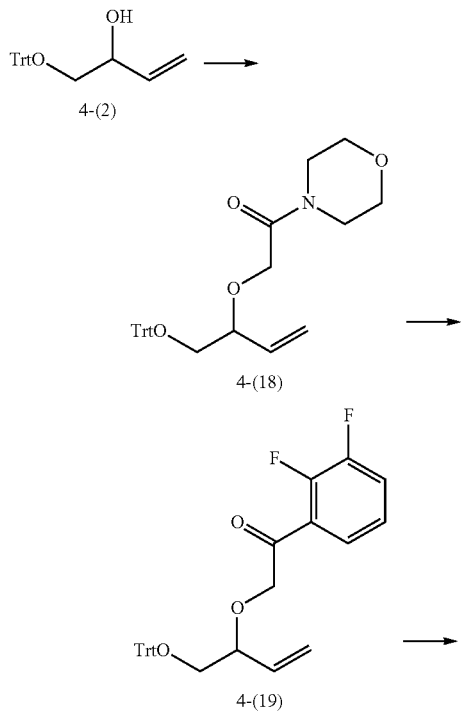

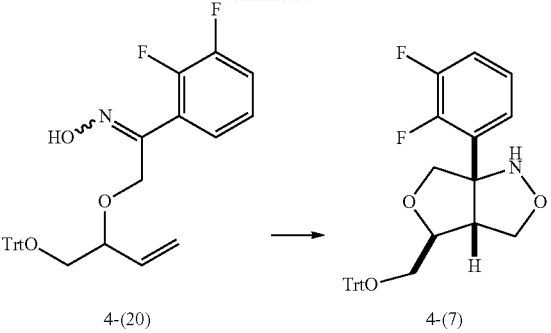

4-(18): 1-Morpholino-2-(1-(trityloxy)but-3-en-2-yloxy)ethanone

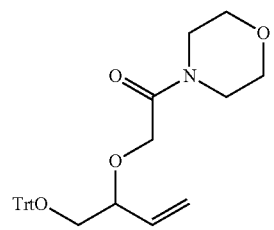

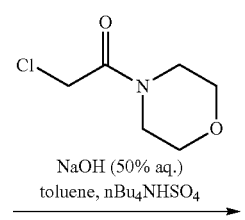

To a reactor with 1-(trityloxy)but-3-en-2-ol (41.6 g, 0.111 mol, 1.0 equiv.) was charged toluene (146 mL). The resulting solution was cooled to 0-5° C. and tetra-n-butylammonium hydrogen sulfate (7.52 g, 0.0222 mol, 0.20 equiv.) was charged. 4-(Chloroacetyl)morpholine (18.1 g, 0.111 mol, 1.00 equiv.) was added at 0-5° C. Sodium hydroxide (50% wt. in water; 88.6 g, 1.10 mol, 10 equiv.) was cooled to 15° C. and charged to the reaction mixture with T<10° C. The reaction mixture was stirred for 1 hr at T<15° C. and monitored for consumption of 1-(trityloxy)but-3-en-2-ol (target>99%). To the reaction mixture was charged 2-methoxy-2-methylpropane (146 mL) and water (146 mL) with T<20° C. The organics were washed with 18% aq. NaCl (73 mL) and sat. aq NH$_4$Cl (21 mL). The organics were filtered over Celite (10.4 g) to remove particulates and rinsed with 2-methoxy-2-methylpropane (83 mL). The solvents were evaporated under vacuum T<30° C. to afford a white solid on standing (55.0 g, 98.7% yield accounting for residual solvents). $^1$H NMR (500 MHz, CDCl$_3$) δ ppm 7.46-7.41 (m, 6H), 7.32-7.25 (m, 6H), 7.25-7.18 (m, 3H), 5.79-5.68 (m, 1H), 5.28 (d, J=17.0 Hz, 1H), 5.26 (d, J=10.1 Hz, 1H), 4.20 (d, J=12.7 Hz, 1H), 4.10 (d, J=12.7 Hz, 1H), 3.97-3.88 (m, 1H), 3.69-3.47 (m, 8H), 3.25 (dd, J=9.9, 6.5 Hz, 1H), 3.17 (dd, J=9.9, 4.3 Hz, 1H); $^{13}$C NMR (125 MHz, CDCl$_3$) δ ppm 167.84, 143.84, 134.84, 128.67, 127.78, 127.04, 119.06, 86.73, 81.07, 68.78, 66.78, 66.34, 45.94, 42.16.

4-(19): 1-(2,3-Difluorophenyl)-2-(1-(trityloxy)but-3-en-2-yloxy)ethanone

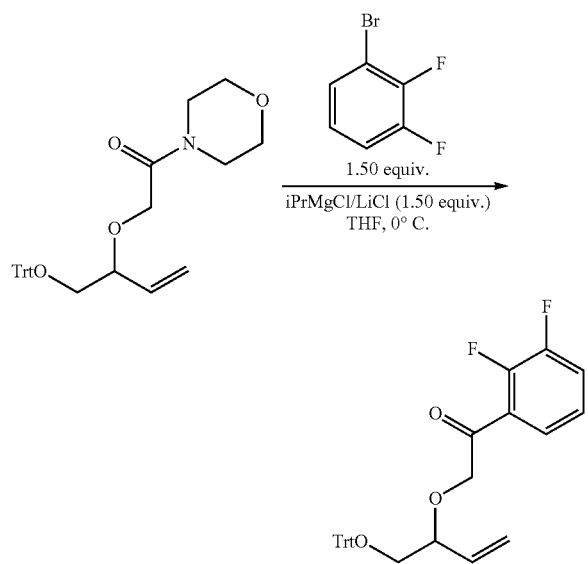

Isopropylmagnesiumchloride-LiCl complex (1.30 M in THF, 155.0 mL, 0.0715 mol) under nitrogen was cooled to 0-5° C., and 2,3-difluorobromobenzene (13.8 g, 0.0715 mol, 1.50 equiv.) was added while T<10° C. After 1 h at 0-5° C., a solution of 1-morpholino-2-(1-(trityloxy)but-3-en-2-yloxy) ethanone (21.8 g, 0.048 mol, 1.0 equiv.) in THF (2.0 vols) was added while T<10° C. The reaction mixture was stirred for 2.5 h and monitored for consumption of 1-morpholino-2-(1-(trityloxy)but-3-en-2-yloxy)ethanone (target>97%). The reaction mixture was quenched by charging into cold sat. aq. NH$_4$Cl (110 mL) and water (33 mL) while T<20° C. 2-Methoxy-2-methylpropane (218 mL) was added and the layers were separated. The organics were washed with sat. aq. NH$_4$Cl (65 mL) and 18% aq. NaCl (44 mL). The organics were concentrated under vacuum T<25° C. to a light yellow oil (21.6 g). $^1$H NMR (500 MHz, CDCl$_3$) δ ppm 7.70-7.64 (m, 1H), 7.47-7.42 (m, 6H), 7.37-7.30 (m, 1H), 7.30-7.25 (m, 6H), 7.24-7.19 (m, 3H), 7.19-7.13 (m, 1H), 5.84-5.71 (m, 1H), 5.30 (d, J=17.3 Hz, 1H), 5.25 (d, J=10.4 Hz, 1H), 4.78 (dd, J=17.7, 3.1 Hz, 1H), 4.70 (dd, J=17.7, 3.1 Hz, 1H), 4.03 (dd, J=11.8, 6.5 Hz, 1H), 3.35 (dd, 1=9.8, 6.4 Hz, 1H), 3.18 (dd, J=9.8, 4.6 Hz, 1H); $^{13}$C NMR (125 MHz, CDCl$_3$) δ ppm 194.15 (dd, J$_{CF}$=4.9, 2.4 Hz), 150.77 (dd, J$_{CF}$=250.3, 14.1 Hz), 150.29 (dd, J$_{CF}$=256.4, 13.9 Hz), 143.98, 135.34, 128.75, 127.76, 126.95, 125.70 (d, J$_{CF}$=12.0 Hz), 125.16 (d, J$_{CF}$=3.5 Hz), 124.55 (dd, J$_{CF}$=6.4, 4.2 Hz), 121.62 (d, J$_{CF}$=17.6 Hz), 118.83, 86.78, 81.35, 74.98 (d, J$_{CF}$=9.5 Hz), 66.71.

4-(20): 1-(2,3-Difluorophenyl)-2-(1-(trityloxy)but-3-en-2-yloxy)ethanone oxime

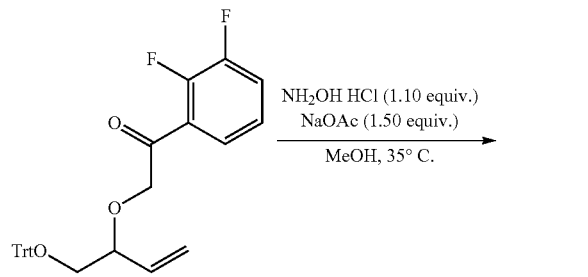

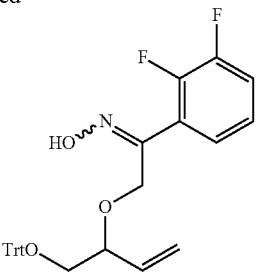

To a solution of 1-(2,3-difluorophenyl)-2-(1-(trityloxy) but-3-en-2-yloxy)ethanone (21.1 g, 0.0435 mol, 1.0 equiv.) in MeOH (106 mL) was added NaOAc (5.36 g, 0.0653 mol, 1.50 equiv.) at ambient temperature. After 5 min., NH$_2$OH HCl (3.33 g, 0.048 mol, 1.10 equiv.) was added in portions. The suspension was warmed to 35° C. and stirred for 1 h. The reaction mixture was cooled to 17.8° C. and stirred for 15 mins, then filtered and rinsed with EtOAc (84 mL). The filtrates were concentrated under vacuum (T<30° C.). To the resulting residue was charged 2-methoxy-2-methylpropane (169 mL) and water (21.1 mL). The organics were washed with sat. aq. NaHCO$_3$ (53 mL) and 18% aq. NaCl (21 mL). The organics were concentrated under vacuum to afford the title compound as an oil (21.0 g). $^1$H NMR (500 MHz, CDCl$_3$) δ ppm 7.42-7.32 (m, 6H), 7.30-7.15 (m, 10H), 7.16-7.06 (m, 1H), 7.03-6.95 (m, 1H), 5.72-5.58 (m, 1H), 5.24-5.13 (m, 2H), 4.80 (d, J=14.6 Hz, 1H), 4.73 (d, J=14.6 Hz, 1H), 4.45 (d, J=12.4 Hz, 0.3H), 4.35 (d, J=12.4 Hz, 0.3H), 3.99-3.91 (m, 0.3H), 3.91-3.83 (m, 1H), 3.20 (dd, J=9.9, 6.8 Hz, 0.3H), 3.09 (dd, J=9.8, 6.6 Hz, 1H), 3.02 (dd, J=9.9, 4.2 Hz, 0.3H), 2.95 (dd, J=9.8, 4.0 Hz, 1H); $^{13}$C NMR (125 MHz, CDCl$_3$) δ ppm 155.40, 150.59 (dd, J$_{CF}$=248.1, 13.0 Hz), 148.86 (dd, J$_{CF}$=252.6, 13.5 Hz), 143.96, 135.10, 128.73, 128.69, 127.72, 127.68, 126.92, 126.85, 124.96, 124.56 (d, J$_{CF}$=10.6 Hz), 124.03-123.86 (m), 118.64 (d, J$_{CF}$=15.1 Hz), 117.92 (d, J$_{CF}$=17.2 Hz), 86.66, 86.50, 81.30, 80.32, 69.20, 66.54, 66.48, 62.57.

4-(7): (3aR*,4S*,6aS*)-6a-(2,3-Difluorophenyl)-4-((trityloxy)methyl)hexahydrofuro[3,4-c]isoxazole

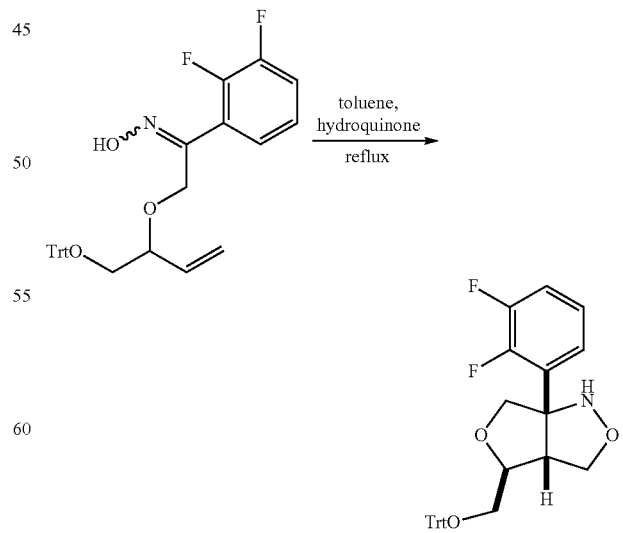

To a solution of 1-(2,3-Difluorophenyl)-2-(1-(trityloxy) but-3-en-2-yloxy)ethanone oxime (20.0 g, 0.0400 mol, 1.0 equiv.) in toluene (140 mL) was charged hydroquinone (0.0882 g, 0.008 mol, 0.2 equiv.). The reaction mixture was heated to reflux (110-115° C.) and held for 13 h. The reaction mixture was cooled to 20-25° C. and then concentrated under vacuum (T<45° C.). The solvents were chased with 2-propanol (100 mL). To the crude residue was charged isopropanol (140 mL) and the mixture was heated to 65-70° C. until a clear solution is formed. The solution was cooled to 0° C. at 10° C./hr and then held for 1 h. The resulting suspension was filtered and the solid was rinsed with cold 2-propanol (40.0). After drying the title compound was obtained as a powder (13.2 g). $^1$H NMR (500 MHz, DMSO) δ ppm 7.42-7.33 (m, 8H), 7.31 (t, J=7.6 Hz, 6H), 7.28-7.21 (m, 3H), 7.20-7.12 (m, 1H), 6.39 (s, 1H), 4.13 (d, J=8.2 Hz, 1H), 4.03 (s, 1H), 3.97 (s, 1H), 3.89 (d, J=9.2 Hz, 1H), 3.81-3.70 (m, 1H), 3.36-3.29 (m, 1H), 3.26 (dd, J=10.1, 6.0 Hz, 1H), 3.15 (dd, J=10.0, 3.5 Hz, 1H); $^{13}$C NMR (125 MHz, DMSO) δ ppm 150.74 (dd, $J_{CF}$=246.4, 14.4 Hz), 148.66 (dd, $J_{CF}$=248.3, 13.5 Hz), 144.09, 130.58, 128.67, 128.32, 127.48, 124.75, 124.45, 117.18 (d, $J_{CF}$=17.0 Hz), 86.57, 84.91, 78.16, 76.81, 64.82, 56.46.

Synthesis of 5-Methoxypyrazine-2-carboxylic acid

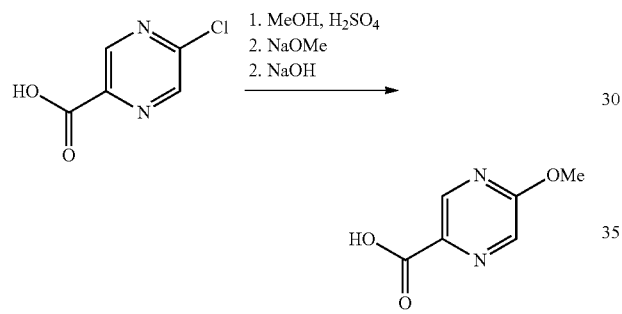

5-Chloropyrazine-2-carboxylic acid (5.0 g, 0.032 mol) was charged to a round-bottom flask equipped with a thermocouple, overhead stirrer and reflux condenser. Methanol (37.5 mL, 0.926 mol) was charged followed by conc. sulfuric acid (0.2 mL, 0.004 mol). The 3-neck flask was equipped with a heating mantle, and then the reaction mixture was heated to ca. 65.0° C. (T internal). The reaction mixture continued to stir at ca. 65.0° C. (T internal) for ca. 4 h. The reaction mixture cooled to ca. 25.8° C. (T internal). Methanol (12 mL, 0.31 mol; EMD; Lot 50197) was charged and the slurry continued to stir at ca. 22.3° C. (T internal) for ca. 15 mins then cooled to ca. 10.0° C. (T internal) under an atmosphere of nitrogen. 25% Sodium methoxide in methanol (1:3, Sodium methoxide:Methanol, 7.7 mL) was charged to flask while temperature remained below 30.0° C. (T internal). The reaction mixture was adjusted to 20.4° C. (T internal). After 30 min., sodium hydroxide (2.0 g, 0.04 mol) and water (37.5 mL, 2.08 mol) were combined to form a solution, and then the solution was charged to the reaction mixture. Water (50.0 mL, 2.78 mol) was charged and then the reaction mixture was heated to 40.0° C. (T internal) for ca. 60 mins. The heating mantle was removed, and then the reaction mixture cooled to ca. 25.4° C. (T internal). 38% aq. HCl Solution (38:62, hydrogen chloride:water, 4.0 mL) was at a rate (ca. 5 min.) such that the temperature remained below 30.0° C. (T internal). The thick slurry was stirred for 1 h at ca. 21.4° C. (T internal), and then filtered over a scintered funnel. The solids were rinsed with water (10.0 mL, 0.555 mol) and dried under vacuum overnight to afford 5-methoxypyrazine-2-carboxylic acid (3.59 g). $^1$H NMR (500 MHz, DMSO) δ ppm 13.24 (1H, br s), 8.79 (1H, d, J=1.2 Hz), 8.37 (1H, d, J=1.2 Hz), 3.98 (s, 3H); $^{13}$C NMR (125 MHz, DMSO) δ ppm 165.36, 161.88, 143.88, 136.82, 135.55, 54.69.

EXAMPLE 4

Alternative Synthesis of N-(3-((4aS,5S,7aS)-2-amino-5-((S)-fluoromethyl)-4a,5-dihydro-4H-furo[3,4-d][1,3]thiazin-7a-yl]-4,5-difluorophenyl}-5-Methoxypyrazine-2-carbamide

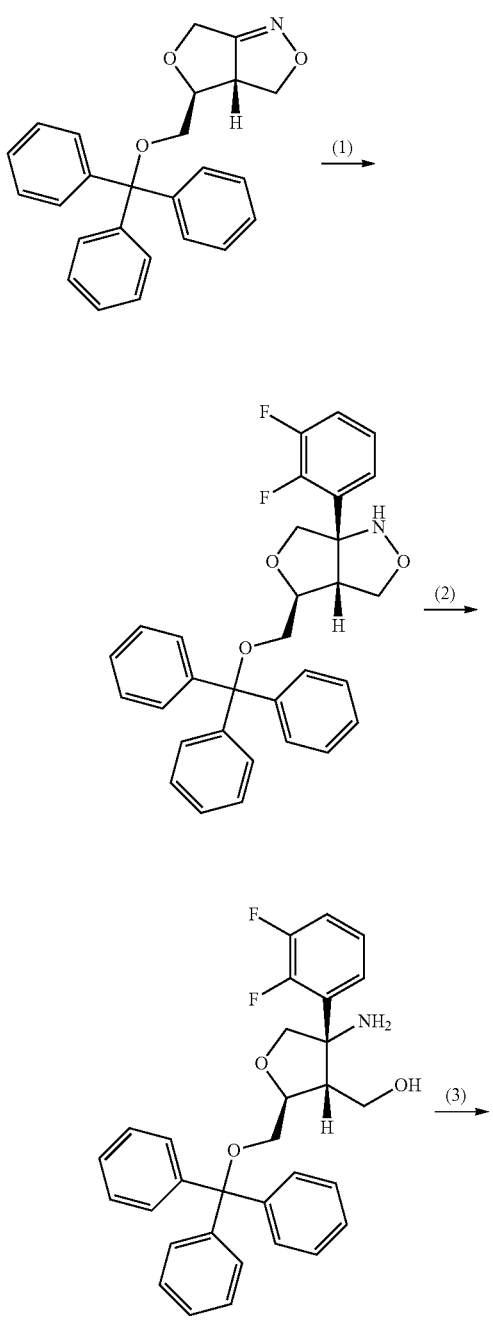

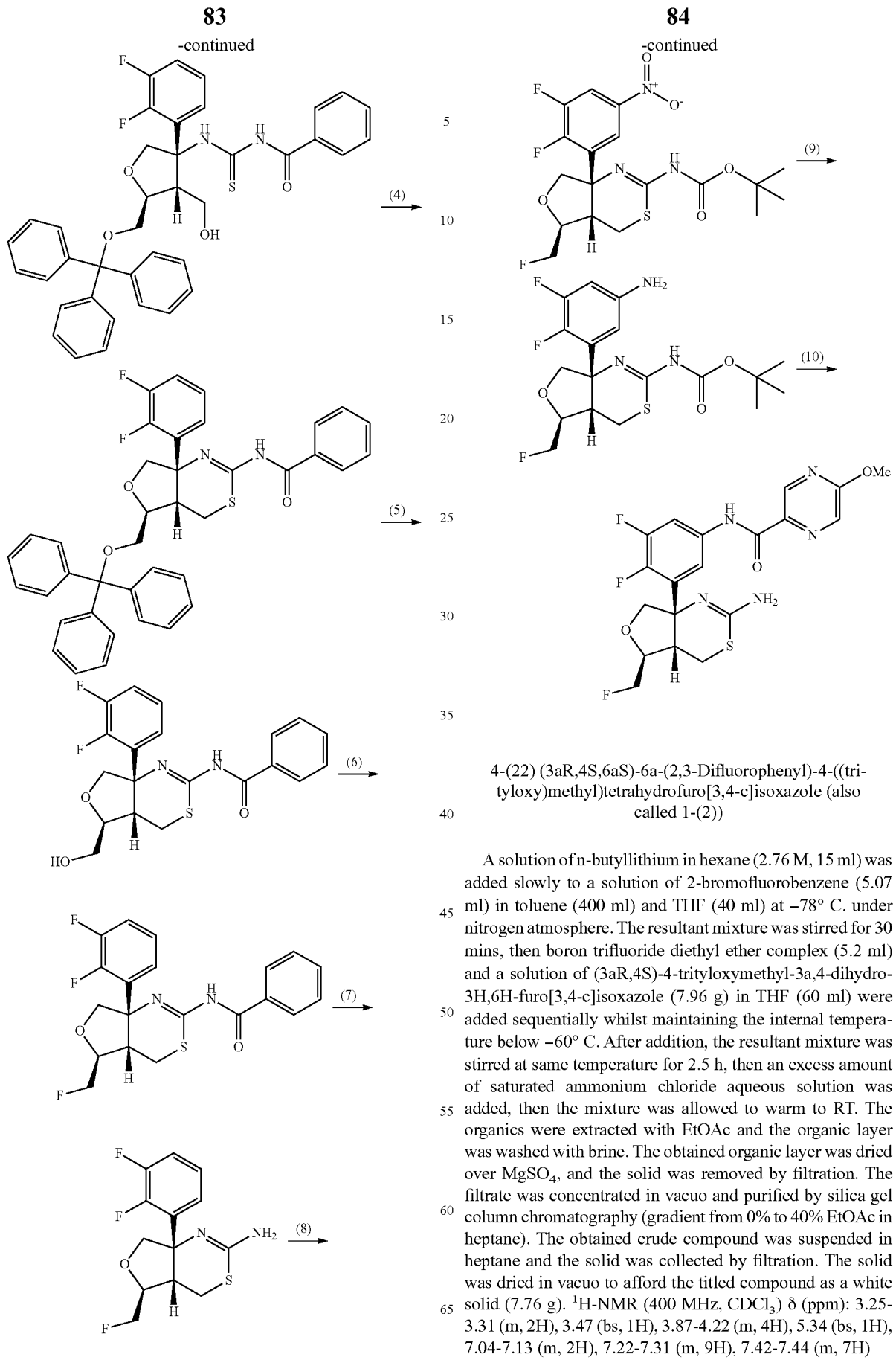

4-(22) (3aR,4S,6aS)-6a-(2,3-Difluorophenyl)-4-((tri-tyloxy)methyl)tetrahydrofuro[3,4-c]isoxazole (also called 1-(2))

A solution of n-butyllithium in hexane (2.76 M, 15 ml) was added slowly to a solution of 2-bromofluorobenzene (5.07 ml) in toluene (400 ml) and THF (40 ml) at −78° C. under nitrogen atmosphere. The resultant mixture was stirred for 30 mins, then boron trifluoride diethyl ether complex (5.2 ml) and a solution of (3aR,4S)-4-trityloxymethyl-3a,4-dihydro-3H,6H-furo[3,4-c]isoxazole (7.96 g) in THF (60 ml) were added sequentially whilst maintaining the internal temperature below −60° C. After addition, the resultant mixture was stirred at same temperature for 2.5 h, then an excess amount of saturated ammonium chloride aqueous solution was added, then the mixture was allowed to warm to RT. The organics were extracted with EtOAc and the organic layer was washed with brine. The obtained organic layer was dried over MgSO$_4$, and the solid was removed by filtration. The filtrate was concentrated in vacuo and purified by silica gel column chromatography (gradient from 0% to 40% EtOAc in heptane). The obtained crude compound was suspended in heptane and the solid was collected by filtration. The solid was dried in vacuo to afford the titled compound as a white solid (7.76 g). $^1$H-NMR (400 MHz, CDCl$_3$) δ (ppm): 3.25-3.31 (m, 2H), 3.47 (bs, 1H), 3.87-4.22 (m, 4H), 5.34 (bs, 1H), 7.04-7.13 (m, 2H), 7.22-7.31 (m, 9H), 7.42-7.44 (m, 7H)

4-(23) ((2S,3R,4S)-4-Amino-4-(2,3-difluorophenyl)-2-trityloxymethyltetrahydrofuran-3-yl)methanol (also called 1-(3))

Zinc powder (10.1 g) was added to a suspension of (3aR,4S,6aS)-6a-(2,3-Difluorophenyl)-4-((trityloxy)methyl)tetrahydrofuro[3,4-c]isoxazole, obtained in Preparation Example 4-(22), (7.76 g) in acetic acid (75 ml) at RT. The mixture was stirred for 11.5 h at RT then the solid was removed by filtration through celite. The filtrate was concentrated in vacuo, then the residue was dissolved with EtOAc. 28% ammonia aqueous solution was added slowly, and the organic layer was separated, washed with brine, and dried over $MgSO_4$. The solid was removed by filtration and the filtrate was concentrated under reduced pressure. Zinc powder (10.1 g) was added to the suspension of the residue in acetic acid (75 ml) at RT. After the mixture was stirred for 11.5 h at same temperature, the solid was removed by filtration through celite. The filtrate was concentrated in vacuo, then the residue was dissolved with EtOAc. 28% ammonia aqueous solution was added slowly, and the organic layer was separated, washed with brine, and dried over $MgSO_4$. The solid was removed by filtration, and the filtrate was concentrated under reduced pressure. The crude mixture was purified by amino silica gel column chromatography (gradient from 50% to 100% EtOAc in heptane) to afford the titled compound (7.04 g) as a white solid. $^1$H-NMR (400 MHz, $CDCl_3$) δ (ppm): 2.60-2.64 (m, 1H), 3.27 (d, J=4.8 Hz, 2H), 3.61-3.65 (m, 1H), 3.89-3.94 (m, 2H), 4.30 (d, J=9.2 Hz, 1H), 4.33-4.37 (m, 1H), 7.04-7.16 (m, 2H), 7.20-7.30 (m, 10H), 7.40-7.43 (m, 6H)

4-(24) N-(((3S,4R,5S)-3-(2,3-difluorophenyl)-4-(hydroxymethyl)-5-((trityloxy)methyl)tetrahydrofuran-3-yl)carbamothioyl)benzamide (also called 1-(4))

Benzoyl isothiocyanate (2.1 ml) was added to a solution of [(2S,3R,4S)-4-amino-4-(2,3-difluorophenyl)-2-((trityloxy)methyl)tetrahydrofuran-3-yl]methanol, obtained in Preparation Example 4-(23), (7.04 g) in DCM (26 ml) at 0° C. After stirring for 10 h and 50 mins at same temperature, the mixture was directly purified by silica gel column chromatography (gradient from 20% to 50% EtOAc in heptane) to afford the titled compound (9.47 g) as a pale yellow solid.

4-(25) N-((4aS,5S,7aS)-7a-(2,3-Difluorophenyl)-5-((trityloxy)methyl)-4a,5,7,7a-tetrahydro-4H-furo[3,4-d][1,3]thiazin-2-yl)benzamide (also called 1-(5) and 4-(11))

Trifluoromethanesulfonic anhydride (3 ml) was added to a solution of N-(((3S,4R,5S)-3-(2,3-difluorophenyl)-4-(hydroxymethyl)-5-((trityloxy)methyl)tetrahydrofuran-3-yl)carbamothioyl)benzamide, obtained in Preparation Example 4-(24), (9.47 g) in pyridine (35 ml) at 0° C. under nitrogen atmosphere. After stirring for 1 h and 40 mins at the same temperature, the mixture was poured into saturated aqueous sodium bicarbonate and EtOAc was added. The organic layer was separated and washed with water and brine, then dried over $MgSO_4$. The solid was removed by filtration, and the filtrate was concentrated in vacuo. The residue was purified by silica gel column chromatography (gradient from 30% to 70% EtOAc in heptane). The obtained crude compound was purified again by silica gel column chromatography (gradient from 10% to 35% EtOAc in heptane) to afford the titled compound (8.34 g) as a pale yellow solid. $^1$H-NMR (400 MHz, $CDCl_3$) δ (ppm): 2.68 (dd, J=13.6, 3.2 Hz, 1H), 3.11-3.14 (m, 1H), 3.32-3.36 (m, 2H), 3.42-3.46 (m, 1H), 4.04 (d, J=9.2 Hz, 1H), 4.54-4.60 (m, 2H), 7.13-7.33 (m, 11H), 7.37-7.53 (m, 10H), 8.11-8.13 (m, 2H)

4-(26) N-((4aS,5S,7aS)-7a-(2,3-Difluorophenyl)-5-(hydroxymethyl)-4a,5,7,7a-tetrahydro-4H-furo[3,4-d][1,3]thiazin-2-yl)benzamide (also called 1-(6) and 4-(12))

Formic acid (35 ml) was added to a solution of N-(4aS,5S,7aS)-7a-(2,3-difluorophenyl)-5-((trityloxy)methyl)-4a,5,7,7a-tetrahydro-4H-furo[3,4-d][1,3]thiazin-2-yl)benzamide, obtained in Preparation Example 4-(25), (8.79 g) in ether (35 ml) at RT. After stirring for 15.25 h at RT, the mixture was concentrated in vacuo to approximately half of the original volume. Formic acid (15 ml) was added to the residue at RT. After stirring for 4 h at RT, the mixture was concentrated in vacuo. Methanol (450 ml) and TEA (9 ml) were added to the residue and the mixture stirred for 1 h at reflux. Further TEA (9 ml) was added and the mixture stirred for 3 h at reflux. The resultant mixture was concentrated in vacuo, and saturated ammonium chloride aqueous solution was added. The mixture was extracted with EtOAc and washed with saturated ammonium chloride solution and brine. The obtained organic layer was dried over $MgSO_4$, and the solid was removed by filtration. The filtrate was concentrated in vacuo and purified by silica gel column chromatography (gradient from 50% to 100% EtOAc in heptane) to afford the targeted compound (5.5 g) as a pale yellow solid. $^1$H-NMR (400 MHz, $CDCl_3$) δ (ppm): 2.80-2.84 (m, 1H), 3.20-3.24 (m, 1H), 3.35-3.38 (m, 1H), 3.73-3.77 (m, 1H), 3.94-3.97 (m, 1H), 4.05-4.08 (m, 1H), 4.51-4.56 (m, 2H), 7.12-7.24 (m, 3H), 7.43-7.47 (m, 2H), 7.51-7.55 (m, 1H), 8.10-8.12 (m, 2H)

4-(27) N-((4aS,5S,7aS)-7a-(2,3-Difluorophenyl)-5-(fluoromethyl)-4a,5,7,7a-tetrahydro-4H-furo[3,4-d][1,3]thiazin-2-yl)benzamide (also called 4-(13)

TEA (14.9 ml), triethylamine trihydrofluoride complex (5.83 ml), and perfluorobutanesulfonyl fluoride (6.17 ml) were added sequentially to a solution of N-((4aS,5S,7aS)-7a-(2,3-Difluorophenyl)-5-(hydroxymethyl)-4a,5,7,7a-tetrahydro-4H-furo[3,4-d][1,3]thiazin-2-yl)benzamide, obtained in Preparation Example 4-(26), (3.83 g) in THF (60 ml) at 0° C. After stirring for 2 h at the same temperature, the mixture was allowed to warm to RT then stirred for 1 h and 20 mins again at RT. Further triethylamine trihydrofluoride complex (4.37 ml) was added then the mixture was stirred for 1 h and 10 mins again at RT. Further TEA (7.49 ml) and perfluorobutanesulfonyl fluoride (3.09 ml) were added and the mixture stirred at RT for 1 h. The resultant mixture was poured into saturated aqueous sodium bicarbonate solution and extracted with EtOAc. The organic layer was dried over $MgSO_4$, and the solid was removed by filtration. The filtrate was concentrated in vacuo, and purified by silica gel column chromatography (gradient from 30% to 100% EtOAc in heptane) to afford targeted compound (2.11 g) as a white solid. $^1$H-NMR (400 MHz, $CDCl_3$) 6 (ppm): 2.83 (dd, J=13.6, 3.6 Hz, 1H), 3.24 (d, J=13.6 Hz, 1H), 3.36 (bs, 1H), 4.03 (d, J=8.8 Hz, 1H), 4.45-4.75 (m, 4H), 7.12-7.24 (m, 3H), 7.46 (t, J=7.6 Hz, 2H), 7.54 (t, J=7.2 Hz, 1H), 8.08 (d, J=4.8 Hz, 2H)

4-(28) (4aS,5S,7aS)-7a-(2,3-difluorophenyl)-5-(fluoromethyl)-4a,5,7,7a-tetrahydro-4H-furo[3,4-d][1,3]thiazin-2-amine (also called 4-(14))

DBU (1.47 ml) was added to a solution of N-04aS,5S,7aS)-7a-(2,3-Difluorophenyl)-5-(fluoromethyl)-4a,5,7,7a-tetrahydro-4H-furo[3,4-d][1,3]thiazin-2-yl)benzamide, obtained in Preparation Example 4-(27), (2.114 g) in MeOH (20 ml). The mixture was heated to reflux and stirred for 4 h and 15 mins then cooled to RT and concentrated in vacuo. The residue was purified by column chromatography on amino silica gel (gradient from 20% to 80% EtOAc in heptane) to afford the targeted compound as colorless gum. $^1$H-NMR (400 MHz, CDCl$_3$) δ (ppm): 2.78-2.82 (m, 1H), 2.98 (quin, J=4.0 Hz, 1H), 3.10-3.14 (m, 1H), 3.87 (dd, J=8.4, 2.4 Hz, 1H), 4.46-4.63 (m, 6H), 7.04-7.15 (m, 2H), 7.17-7.21 (m, 1H)

4-(29) tert-butyl ((4aS,5S,7aS)-7a-(2,3-difluoro-5-nitrophenyl)-5-(fluoromethyl)-4a,5,7,7a-tetrahydro-4H-furo[3,4-d][1,3]thiazin-2-yl)carbamate Fuming nitric acid (475 µl) was added to a solution of (4aS,5S,7aS)-7a-(2,3-difluorophenyl)-5-(fluoromethyl)-4a,5,7,7a-tetrahydro-4H-furo[3,4-d][1,3]thiazin-2-amine, obtained in Preparation Example 4-(28), (1.45 g) in TFA (12 ml) and sulfuric acid (917 µl) at 0° C. and then the mixture was stirred for 90 min at the same temperature. Further sulfuric acid (917 µl) and fuming nitric acid (4750) were added sequentially and the mixture stirred for 150 min at the same temperature, then the reaction mixture was poured onto crushed ice and sodium hydroxide solution (50%, 8.1 ml), and the reaction vessel was washed with chloroform. Sodium hydroxide solution (50%) was added to the mixture until the pH was greater than 13, then extracted with chloroform (3 times). The combined organic extracts were dried over MgSO$_4$, and the solid was removed by filtration. The filtrate was concentrated in vacuo. The residue was dissolved in THF (12 ml) and TEA (4.58 ml) and Boc$_2$O (1.92 g) were added at RT. After stirring for 19 h at RT, the resultant mixture was poured onto saturated aqueous ammonium chloride and extracted with EtOAc. The organic layer was washed sequentially with saturated aqueous ammonium chloride, water and brine. The organic layer was dried over MgSO$_4$, and the solid was removed by filtration. The filtrate was concentrated in vacuo, and then the crude compound was purified by silica gel column chromatography (gradient from 20% to 50% EtOAc in heptane) to afford the targeted compound (1.17 g) as a white solid. $^1$H-NMR (400 MHz, CDCl$_3$) δ (ppm): 1.53 (s, 9H), 2.71-2.76 (m, 1H), 2.96-3.00 (m, 1H), 3.13-3.20 (m, 1H), 3.84 (d, J=8.8 Hz, 1H), 4.47 (dd, J=8.8, 1.2 Hz, 1H), 4.50-4.72 (m, 3H), 7.29-7.31 (m, 1H), 8.04-8.09 (m, 1H), 8.11-8.14 (m, 1H)

4-(30) tert-butyl ((4aS,5S,7aS)-7a-(5-amino-2,3-difluorophenyl)-5-(fluoromethyl)-4a,5,7,7a-tetrahydro-4H-furo[3,4-d][1,3]thiazin-2-yl)carbamate Tin(II) chloride dihydrate (2.06 g) was added to a suspension of tert-butyl ((4aS,5S,7aS)-7a-(2,3-difluoro-5-nitrophenyl)-5-(fluoromethyl)-4a,5,7,7a-tetrahydro-4H-furo[3,4-d][1,3]thiazin-2-yl)carbamate, obtained in Preparation Example 2-(29), (1.17 g) in ethanol (20 ml) at RT. The mixture was stirred for 16 h at the same temperature (the solid gradually dissolved and the reaction color became yellow). The resultant mixture was poured into 2N sodium hydroxide solution and the organic was extracted with EtOAc. The organic layer was washed sequentially with water and brine, then dried over MgSO$_4$. The solid was removed by filtration, and the filtrate was concentrated in vacuo. The crude mixture was purified by silica gel column chromatography (gradient from 20% to 60% EtOAc in heptane) acetate to afford the targeted compound (1.09 g) as a pale yellow solid. $^1$H-NMR (400 MHz, CDCl$_3$) δ (ppm): 1.51 (s, 9H), 2.69-2.73 (m, 1H), 3.07-3.15 (m, 2H), 3.69 (bs, 2H), 3.84-3.85 (m, 1H), 4.49-4.67 (m, 4H), 6.34-6.36 (m, 1H), 6.44 (ddd, J=11.2, 6.4, 2.8 Hz, 1H)

4-(31) N-(3-((4aS,5S,7aS)-2-amino-5-(fluoromethyl)-4a,5,7,7a-tetrahydro-4H-furo[3,4-d][1,3]thiazin-7a-yl)-4,5-difluorophenyl)-5-methoxypyrazine-2-carboxamide (also called 4-(17))

Methoxypyrazine-2-carboxylic acid (159 mg), PyBOP (898 mg), and diisopropylethylamine (754 µl) were added to a mixture of tert-butyl ((4aS,5S,7aS)-7a-(5-amino-2,3-difluorophenyl)-5-(fluoromethyl)-4a,5,7,7a-tetrahydro-4H-furo[3,4-d][1,3]thiazin-2-yl)carbamate, obtained in Preparation Example 4-(30), (359 mg) in DCM (14 ml) at RT. The mixture was stirred for 3 h at the same temperature. The resultant mixture was purified directly by silica gel column chromatography (gradient from 15% to 70% EtOAc in heptane). After evaporation, TFA (7 ml) was added to the mixture of the obtained compound in DCM (7 ml) at RT. After stirring for 75 mins at the same temperature, the resultant mixture was concentrated in vacuo. Chloroform and saturated aqueous sodium bicarbonate were added to the residue and the organic was extracted with chloroform (3 times). The combined organic layers were dried over MgSO$_4$ and the solid was removed by filtration. The crude mixture was purified by amino silica gel column chromatography (gradient from 30% to 100% EtOAc in heptane) to afford the targeted compound (320 mg) as a white solid. $^1$H-NMR (400 MHz, CDCl$_3$) δ (ppm): 2.81 (dd, J=13.6, 4.0 Hz, 1H), 3.02-3.06 (m, 1H), 3.15 (dd, J=13.6, 3.6 Hz, 1H), 3.86 (dd, J=8.8, 2.4 Hz, 1H), 4.07 (s, 3H), 4.50-4.59 (m, 5H), 4.64-4.65 (m, 1H), 7.18-7.20 (m, 1H), 8.06 (ddd, J=11.6, 6.8, 2.8 Hz, 1H), 8.16 (d, J=1.2 Hz, 1H), 9.01 (d, J=1.2 Hz, 1H), 9.52 (bs, 1H)

In Vitro Cellular Assay:
Quantification of Aβ Peptide in Culture of Neurons from Rat Fetus Brain
(1) Rat Primary Neuronal Culture Primary neuronal cultures were prepared from the cerebral cortex of embryonic day 18 Wistar rats (Charles River, UK). Specifically, the embryos were aseptically removed from pregnant rats under ether anesthesia. The brain was isolated from the embryo and immersed in HBSS (Sigma Aldrich #H9269) containing 10 mM HEPES (Gibco #15630-056). The cerebral cortex was collected from the isolated brain under a stereoscopic microscope. The cerebral cortex fragments collected were enzymatically treated in an enzyme solution containing 0.05% trypsin-EDTA solution (GIBCO, #25300) at 37° C. for 20 minutes to disperse the cells. The cells were then washed twice and then gently resuspended in Neurobasal medium (Gibco #21103) supplemented with 2% B27 supplement (GIBCO #17504-044), 0.5 mM L-glutamine (GIBCO #25030), 1×N2 (GIBCO #17502-048), 100 µg/ml Pen/Strep (GIBCO 15140-122) and 5% heat inactivated FCS (PAA #A15-701). The cell dispersion was filtered through a 40-µm nylon mesh (BD Falcon #352340) to remove the remaining cell mass, and thus a neuronal cell suspension was obtained. The neuronal cell suspension was diluted with the medium above and then plated in a volume of 100 µL/well at an initial cell density of 3.25×10$^5$ cells/ml in poly-D-lysine coated 96-well culture plate (Greiner #655940). The plated cells were cultured in the culture plate at 37° C. in 5% CO$_2$-95% air for 24 hrs. The total amount of the medium was replaced with 'assay Neurobasal medium' (as above excluding heat inactivated FCS), and then the cells were cultured for a further five days.

(2) Addition of Compound

The drug was added to the culture plate on Day 6 of culture as follows. 8 point compound serial dilutions were generated in DMSO at a concentration of ×1000 that of the final assay concentration (FAC). Compound solutions were then prepared by adding 999 ul of 'Assay Neurobasal media' (as described in above section) to 1 ul of DMSO compound stock. The total amount of the medium was removed from each of the cell plate wells, and 140 μL/well of 'Assay Neurobasal media' was added followed by 60 ul of compound solution. The final DMSO concentration was 0.1%.

(3) Sampling

The cells were cultured for either 1 or 3 days after addition of the compound for ABx-40 and ABx-42 assays respectively. 150 μl of sample medium was collected and used as the ELISA sample.

(4) Evaluation of Cell Survival

Cell survival was evaluated using an Alamar assay according to the following procedure. After collecting the sample to be used in the ELISA assay, 50 μl of 20% Alamar blue solution (Invitrogen #DAL1100) in assay Neurobasal media, was added to 50 μl of remaining sample within each well. Cells were then incubated at 37° C. in 5% $CO_2$-95% air for 1 hr.

Measurement of fluorescence intensity for each well was the carried out at 540/590 nm using a Pherastar plus plate reader (BMG labtech). Upon measurement, wells having no cells plated and containing only the medium and Alamar solution were set as background (bkg).

(5) Aβ ELISA

Human/Rat β Amyloid (42) ELISA Kit Wako (#290-62601) and Human/Rat P Amyloid (40) ELISA Kit Wako (#294-62501) from Wako Pure Chemical Industries, Ltd. were used for Aβ ELISA. Aβ ELISA was carried out according to the protocols recommended by the manufacturers, described in the documents accompanying the kits. The results were shown as percentage of the control groups and IC50 values for each compound were determined using four parameter logistic fit model using the XLFIT5 software package (IDBS).

The compounds of the present invention have an Aβ42 production reducing effect.

The compound of the general formula (I) or pharmaceutically acceptable salt thereof according to the present invention has an Aβ42 production reducing effect. Thus, the present invention can particularly provide a prophylactic or therapeutic agent for a neurodegenerative disease caused by Aβ such as Alzheimer-type dementia or Down's syndrome.

As measured by the above in vitro assay, compound Examples 1 to 4 showed the $IC_{50}$ values in Table 7:

TABLE 7

| Example | $IC_{50}$ (uM) |
|---------|----------------|
| 1 | 0.007 |
| 2 | 0.004 |
| 3 | 0.004 |
| 4 | 0.012 |

The invention claimed is:

1. A compound of formula (I):

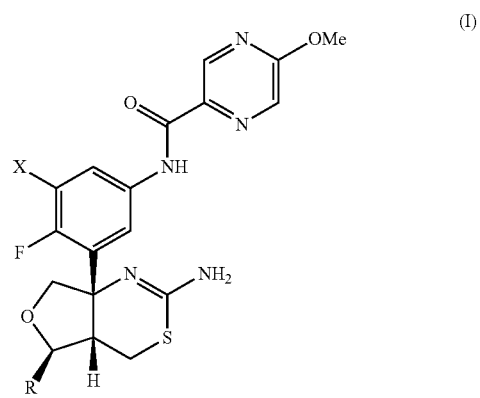

or a pharmaceutically acceptable salt thereof,
wherein
X is hydrogen or fluorine;
R is monofluoromethyl or difluoromethyl.

2. The compound or pharmaceutically acceptable salt thereof according to claim 1, wherein X is hydrogen.

3. The compound or pharmaceutically acceptable salt thereof according to claim 1, wherein R is monofluoromethyl.

4. The compound or pharmaceutically acceptable salt thereof according to claim 1, wherein the compound or pharmaceutically acceptable salt thereof is selected from the group consisting of:
N-(3-((4aS,5S,7aS)-2-amino-5-(difluoromethyl)-4a,5,7,7a-tetrahydro-4H-furo[3,4-d][1,3]thiazin-7a-yl)-4,5-difluorophenyl)-5-methoxypyrazine-2-carboxamide;
N-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-5-methoxypyrazine-2-carboxamide;
N-(3-((4aS,5S,7aS)-2-amino-5-(difluoromethyl)-4a,5,7,7a-tetrahydro-4H-furo[3,4-d][1,3]thiazin-7a-yl)-4-fluorophenyl)-5-methoxypyrazine-2-carboxamide; and
N-(3-((4aS,5S,7aS)-2-amino-5-(fluoromethyl)-4a,5,7,7a-tetrahydro-4H-furo[3,4-d][1,3]thiazin-7a-yl)-4,5-difluorophenyl)-5-methoxypyrazine-2-carboxamide;
or a pharmaceutically acceptable salt thereof.

5. The compound or pharmaceutically acceptable salt thereof according to claim 1, which is N-(3-((4aS,5S,7aS)-2-amino-5-(fluoromethyl)-4a,5,7,7a-tetrahydro-4H-furo[3,4-d][1,3]thiazin-7a-yl)-4-fluorophenyl)-5-methoxypyrazine-2-carboxamide, or a pharmaceutically acceptable salt thereof.

6. The compound or pharmaceutically acceptable salt thereof according to claim 1, which is N-(3-((4aS,5S,7aS)-2-amino-5-(fluoromethyl)-4a,5,7,7a-tetrahydro-4H-furo[3,4-d][1,3]thiazin-7a-yl)-4,5-difluorophenyl)-5-methoxypyrazine-2-carboxamide, or a pharmaceutically acceptable salt thereof.

7. A method for treating type 2 diabetes, comprising administering to a human subject suffering from type 2 diabetes an effective amount of the compound or pharmaceutically acceptable salt thereof according to claim 1.

8. A pharmaceutical composition comprising the compound or pharmaceutically acceptable salt thereof according to claim 1 as an active ingredient in association with a pharmaceutically acceptable carrier.

* * * * *